(12) United States Patent
Won et al.

(10) Patent No.: US 12,075,694 B2
(45) Date of Patent: Aug. 27, 2024

(54) COMPOSITION, ORGANIC OPTOELECTRONIC DEVICE AND DISPLAY DEVICE

(71) Applicants: SAMSUNG SDI CO., LTD., Yongin-si (KR); Samsung Electronics Co., Ltd., Suwon-si (KR)

(72) Inventors: Jongwoo Won, Suwon-si (KR); Dong Min Kang, Suwon-si (KR); Jun Seok Kim, Suwon-si (KR); Jinhyun Lui, Suwon-si (KR); Byoungkwan Lee, Suwon-si (KR); Sangshin Lee, Suwon-si (KR); Hyungyu Lee, Suwon-si (KR); Sung-Hyun Jung, Suwon-si (KR); Ho Kuk Jung, Suwon-si (KR); Kyunghee Hyung, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 845 days.

(21) Appl. No.: 17/047,445

(22) PCT Filed: Mar. 25, 2019

(86) PCT No.: PCT/KR2019/003444
§ 371 (c)(1),
(2) Date: Oct. 14, 2020

(87) PCT Pub. No.: WO2019/208937
PCT Pub. Date: Oct. 31, 2019

(65) Prior Publication Data
US 2021/0119136 A1 Apr. 22, 2021

(30) Foreign Application Priority Data
Apr. 23, 2018 (KR) .................. 10-2018-0046910

(51) Int. Cl.
*H01L 51/50* (2006.01)
*C07D 209/80* (2006.01)
*C07D 403/10* (2006.01)
*C07D 405/12* (2006.01)
(Continued)

(52) U.S. Cl.
CPC ......... *H10K 85/636* (2023.02); *C07D 209/80* (2013.01); *C07D 403/10* (2013.01);
(Continued)

(58) Field of Classification Search
None
See application file for complete search history.

(56) References Cited

U.S. PATENT DOCUMENTS

2019/0165281 A1   5/2019   Jang et al.

FOREIGN PATENT DOCUMENTS

| JP | H 11-144866 A | 5/1999 |
|----|---------------|--------|
| KR | 10-1074193 B1 | 10/2011 |

(Continued)

OTHER PUBLICATIONS

International Search Report dated Jun. 24, 2019 for PCT/KR2019/003444.
Chinese Office action dated Jun. 26, 2024.

*Primary Examiner* — Gregory D Clark
(74) *Attorney, Agent, or Firm* — Lee IP Law, P.C.

(57) ABSTRACT

A composition including a first compound represented by a combination of Chemical Formula 1 and Chemical Formula 2 and a second compound represented by Chemical Formula 3, an organic optoelectronic device, and a display device are disclosed.
Definitions of Chemical Formula 1 to Chemical Formula 3 are the same as described in the specification.

17 Claims, 1 Drawing Sheet

(51) Int. Cl.
    *C07D 405/14*      (2006.01)
    *H10K 85/60*       (2023.01)
    *H10K 50/11*       (2023.01)
    *H10K 101/10*     (2023.01)

(52) U.S. Cl.
    CPC ......... *C07D 405/12* (2013.01); *C07D 405/14* (2013.01); *H10K 85/654* (2023.02); *H10K 85/6572* (2023.02); *H10K 85/6574* (2023.02); *H10K 50/11* (2023.02); *H10K 2101/10* (2023.02)

(56) References Cited

FOREIGN PATENT DOCUMENTS

| | | | | |
|---|---|---|---|---|
| KR | 10-2015-0004099 A | 1/2015 | | |
| KR | 10-2016-0029721 A | 3/2016 | | |
| KR | 10-2017-0096767 A | 8/2017 | | |
| KR | 10-2017-0101577 A | 9/2017 | | |
| KR | 10-2017-0117775 A | 10/2017 | | |
| KR | 2017-117775 | * 10/2017 | ............. | H01L 51/50 |
| KR | 20170117775 A | † 10/2017 | | |
| KR | 10-2017-0123955 A | 11/2017 | | |
| KR | 20170123955 A | † 11/2017 | | |
| KR | 10-1804630 B1 | 12/2017 | | |
| KR | 10-2018-0032496 A | 3/2018 | | |
| TW | 201229202 A1 | 7/2012 | | |
| WO | WO 2010/021524 A2 | 2/2010 | | |
| WO | WO 2017/179875 A1 | 10/2017 | | |
| WO | 2017188597 A1 | 11/2017 | | |
| WO | 2018004095 A1 | 1/2018 | | |

\* cited by examiner
† cited by third party

【Figure 1】
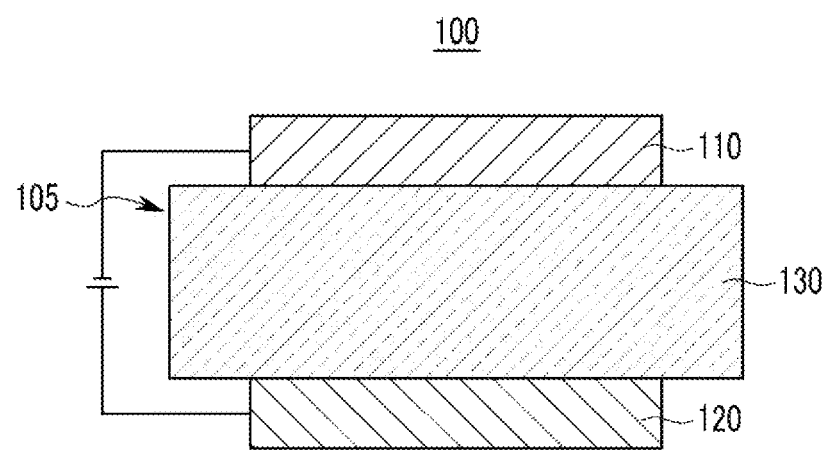
【Figure 2】
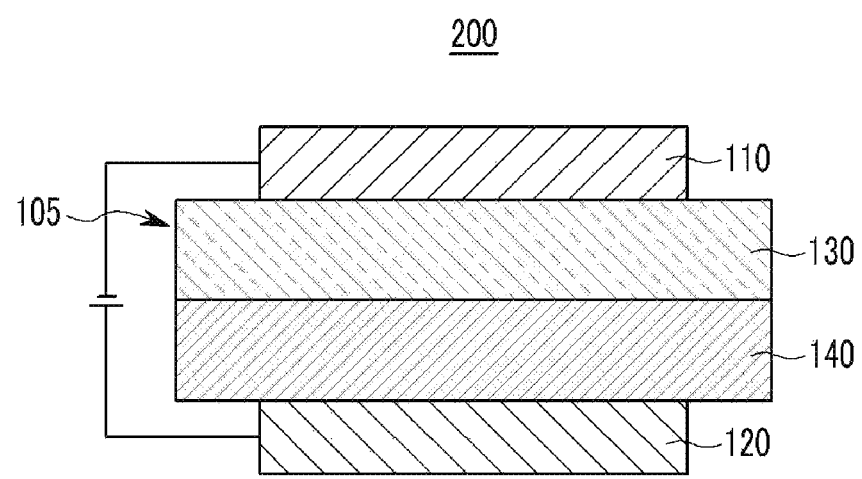

COMPOSITION, ORGANIC OPTOELECTRONIC DEVICE AND DISPLAY DEVICE

CROSS REFERENCE TO RELATED APPLICATIONS

This is the U.S. national phase application based on PCT Application No. PCT/KR2019/003444, filed Mar. 25, 2019, which is based on Korean Patent Application No. 10-2018-0046910, filed Apr. 23, 2018, the entire contents of all of which are hereby incorporated by reference.

TECHNICAL FIELD

A composition, an organic optoelectronic device, and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and Performance of an organic light emitting diode may be affected by organic materials disposed between electrodes.

DISCLOSURE

Technical Problem

An embodiment provides a composition capable of realizing an organic optoelectronic device having high efficiency and a long life-span.

Another embodiment provides an organic optoelectronic device including the composition.

Yet another embodiment provides a display device including the organic optoelectronic device.

Technical Solution

According to an embodiment, a composition includes a first compound represented by a combination of Chemical Formula 1 and Chemical Formula 2 and a second compound represented by Chemical Formula 3.

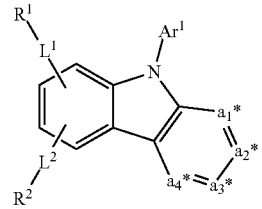

[Chemical Formula 1]

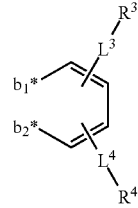

[Chemical Formula 2]

In Chemical Formula 1 and Chemical Formula 2,
$Ar^1$ is a substituted or unsubstituted C6 to C30 aryl group, a substituted or unsubstituted C2 to C30 heterocyclic group, or a combination thereof,
adjacent two of $a_1^*$ to $a_4^*$ are linked with $b_1^*$ and $b_2^*$, respectively,
remaining two of $a_1^*$ to $a_4^*$ not being linked with $b_1^*$ and $b_2^*$ are independently $C-L^a-R^a$,
$L^a$ and $L^1$ to $L^4$ are independently a single bond, a substituted or unsubstituted C6 to C20 arylene group, a substituted or unsubstituted C2 to C20 heterocyclic group, or a combination thereof,
$R^a$ and $R^1$ to $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and
at least one of $R^a$ and $R^1$ to $R^4$ is a group represented by Chemical Formula A,

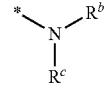

[Chemical Formula A]

wherein, in Chemical Formula A,
$R^b$ and $R^c$ are independently a substituted or unsubstituted C6 to C30 aryl group, a substituted or unsubstituted C2 to C30 heterocyclic group, or a combination thereof, and
* is a linking point with $L^a$ and $L^1$ to $L^4$;

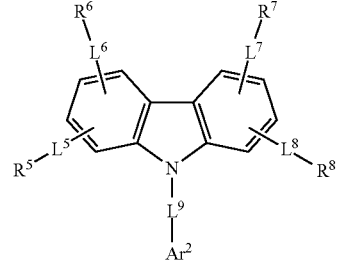

[Chemical Formula 3]

wherein, in Chemical Formula 3, $L^5$ to $L^9$ are independently a single bond, a substituted or unsubstituted C6 to C20 arylene group, a substituted or unsubstituted C2 to C20 heterocyclic group, or a combination thereof, $Ar^2$ is a substituted or unsubstituted C6 to C30 aryl group, a substituted or unsubstituted C2 to C30 heterocyclic group, or a combination thereof, $R^5$ to $R^8$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^5$ to $R^8$ are independently present or adjacent groups thereof are linked with each other to form a substituted or unsubstituted aromatic monocyclic or polycyclic ring, and at least one of $Ar^2$ and $R^5$ to $R^8$ is a group represented by Chemical Formula B,

[Chemical Formula B]

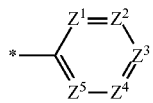

wherein, in Chemical Formula B, $Z^1$ to $Z^5$ are independently N or $C-L^b-R^d$, at least one of $Z^1$ to $Z^5$ is N, wherein $L^b$ is independently a single bond, a substituted or unsubstituted C6 to C20 arylene group, a substituted or unsubstituted C2 to C20 heterocyclic group, or a combination thereof, $R^d$ is independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^d$ is independently present or adjacent groups thereof are linked with each other to form a substituted or unsubstituted aromatic monocyclic or polycyclic ring, or a substituted or unsubstituted aromatic monocyclic or polycyclic heteroring, and

* is a linking point with $L^5$ to $L^9$.

According to another embodiment, an organic optoelectronic device includes an anode and a cathode facing each other, and at least one organic layer disposed between the anode and the cathode, wherein the organic layer includes the composition.

According to another embodiment, a display device including the organic optoelectronic device is provided.

An organic optoelectronic device having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS 100, 200: organic light emitting diode
105: organic layer
110: cathode
120: anode
130: light emitting layer
140: hole auxiliary layer

BEST MODE

Hereinafter, embodiments of the present invention are described in detail. However, these embodiments are exemplary, the present invention is not limited thereto and the present invention is defined by the scope of claims.

In the present specification when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In examples of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, the "substituted" refers to replacement of at least one hydrogen of a substituent or a compound by deuterium, a C1 to C20 alkyl group, a C6 to C30 aryl group, or a C2 to C30 heteroaryl group. In addition, specific examples of the present invention, the "substituted" refers to replacement of at least one hydrogen of a substituent or a compound by deuterium, a C1 to C5 alkyl group, a C6 to C18 aryl group, a pyridinyl group, quinolinyl group, an isoquinolinyl group, a dibenzofuranyl group, a dibenzothiophenyl group, or a carbazolyl group. In addition, specific examples of the present invention, the "substituted" refers to replacement of at least one hydrogen of a substituent or a compound by deuterium, a C1 to C5 alkyl group, a C6 to C18 aryl group, a dibenzofuranyl group, or a dibenzothiophenyl group. In addition, specific examples of the present invention, the "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenylene group, a dibenzofuranyl group, or a dibenzothiophenyl group.

In the present specification when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quaterphenyl group, and the like, and two or more hydrocarbon aromatic moieties are fused directly or indirectly to provide a non-aromatic fused ring, for example a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, or a combination thereof, but is not limited thereto.

More specifically, the substituted or unsubstituted C2 to C30 heterocyclic group may be a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzothiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, a composition for an organic optoelectronic device according to an embodiment is described.

A composition for an organic optoelectronic device according to an embodiment includes a first compound having hole characteristics and a second compound having electron characteristics.

The first compound is represented by a combination of Chemical Formula 1 and Chemical Formula 2.

[Chemical Formula 1]

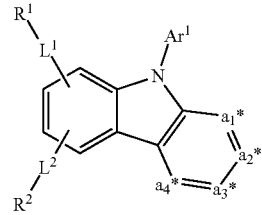

[Chemical Formula 2]

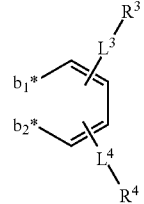

In Chemical Formula 1 and Chemical Formula 2, $Ar^1$ is a substituted or unsubstituted C6 to C30 aryl group, a substituted or unsubstituted C2 to C30 heterocyclic group, or a combination thereof, adjacent two of $a_1^*$ to $a_4^*$ are linked with $b_1^*$ and $b_2^*$, respectively, remaining two of $a_1^*$ to $a_4^*$ not being linked with $b_1^*$ and $b_2^*$ are independently $C-L^a-R^a$, $L^a$ and $L^1$ to $L^4$ are independently a single bond, a substituted or unsubstituted C6 to C20 arylene group, a substituted or unsubstituted C2 to C20 heterocyclic group, or a combination thereof, $R^a$ and $R^1$ to $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^4$ is a group represented by Chemical Formula A,

[Chemical Formula A]

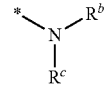

wherein, in Chemical Formula A, $R^b$ and $R^c$ are independently a substituted or unsubstituted C6 to C30 aryl group, a substituted or unsubstituted C2 to C30 heterocyclic group, or a combination thereof, and

* is a linking point with $L^a$ and $L^1$ to $L^4$;

The first compound has a structure where benzocarbazole is substituted with amine, thereby a HOMO electron cloud is expanded from amine into the benzocarbazole, and thus hole injection and transport characteristics may be improved due to high HOMO energy.

In addition, since the benzocarbazole has relatively high HOMO energy compared with bicarbazole and indolocarbazole, a device having a low driving voltage may be realized due to the structure where benzocarbazole is substituted with amine.

In addition, the bicarbazole and the indolocarbazole are not appropriate as a red host due to high T1 energy, but the structure where benzocarbazole is substituted with amine has a desirable T1 energy as a red host. Accordingly, a device including the compound according to the present invention may realize high efficiency/long life-span characteristics.

Meanwhile, it may be included with the second compound to balance holes and electrons and thereby a driving voltage including the same may be lowered.

For example, $R^b$ and $R^c$ may independently be a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

For example, $R^b$ and $R^c$ may independently be a substituted or unsubstituted, phenyl group, a substituted or unsubstituted p-biphenyl group, or a substituted or unsubstituted fluorenyl group, wherein the substituent may be a phenyl group, a naphthyl group, an anthracenyl group, a phenanthrenyl group, triphenylene group, a carbazolyl group, a dibenzofuranyl group, or a dibenzothiophenyl group.

For example, $Ar^1$ may independently be a substituted or unsubstituted C6 to C20 aryl group or a substituted or unsubstituted C2 to C20 heterocyclic group.

For example, $Ar^1$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof.

For example, $Ar^1$ may be a substituted or unsubstituted phenyl group, a substituted or unsubstituted biphenyl group, a substituted or unsubstituted naphthyl group, a substituted or unsubstituted dibenzofuranyl group, a substituted or unsubstituted dibenzothiophenyl group, or a substituted or unsubstituted carbazolyl group, but is not limited thereto.

For example, $L^a$ and $L^1$ to $L^4$ may independently be a single bond or a substituted or unsubstituted C6 to C20 arylene group.

For example, $L^a$ and $L^1$ to $L^4$ may independently be a single bond, a substituted or unsubstituted phenylene group, a substituted or unsubstituted biphenylene group, a substituted or unsubstituted terphenylene group, or a substituted or unsubstituted naphthylene group.

For example, $L^a$ and $L^1$ to $L^4$ may independently be a single bond, a substituted or unsubstituted m-phenylene group, a substituted or unsubstituted p-phenylene group, a substituted or unsubstituted o-phenylene group, a substituted or unsubstituted m-biphenylene group, a substituted or unsubstituted p-biphenylene group, a substituted or unsubstituted o-biphenylene group, a substituted or unsubstituted m-terphenylene group, a substituted or unsubstituted p-terphenylene group, or a substituted or unsubstituted o-terphenylene group. Herein, substituted may refer to for example replacement of at least one hydrogen by deuterium, a C1 to C20 alkyl group, a C6 to C20 aryl group, a halogen, a cyano group, or a combination thereof, but is not limited thereto.

For example, $R^a$ and $R^1$ to $R^4$ may independently be hydrogen, deuterium, a cyano group, a substituted or unsubstituted C1 to C10 alkyl group, a substituted or unsubstituted C6 to C20 aryl group, a substituted or unsubstituted C2 to C20 heterocyclic group, or the group represented by Chemical Formula A.

For example, $R^a$ and $R^1$ to $R^4$ may independently be hydrogen or the group represented by Chemical Formula A, but is not limited thereto.

For example, the first compound may be for example represented by one of Chemical Formula 1A to Chemical Formula 1C according to a fusion position of Chemical Formula 1 and Chemical Formula 2.

[Chemical Formula 1A]

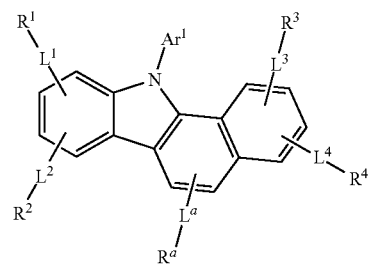

[Chemical Formula 1B]

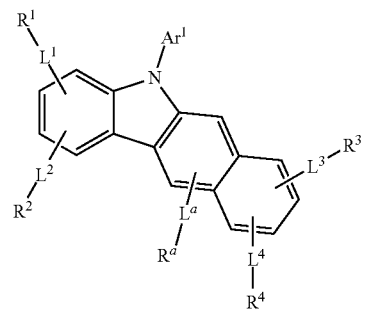

-continued

[Chemical Formula 1C]

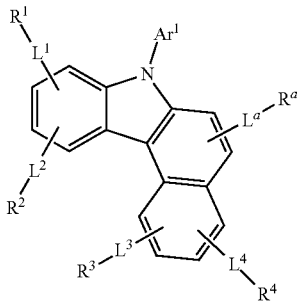

In Chemical Formula 1A to Chemical Formula 1C, $Ar^1$, $L^a$ and $L^1$ to $L^4$, and $R^a$ and $R^1$ to $R^4$ are the same as described above.

For example, Chemical Formula 1A may be represented by one of Chemical Formula 1A-1 to Chemical Formula 1A-3 according to a substitution position of the group represented by Chemical Formula A.

[Chemical Formula 1A-1]

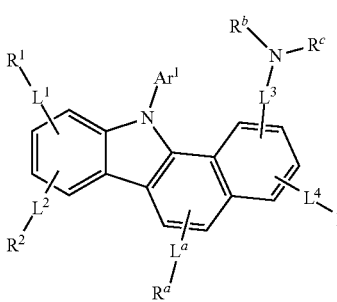

[Chemical Formula 1A-2]

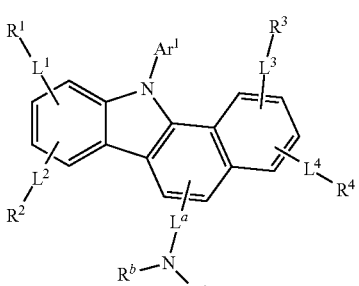

[Chemical Formula 1A-3]

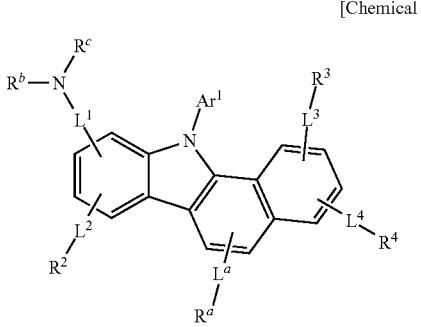

In Chemical Formula 1A-1 to Chemical Formula 1A-3, $Ar^1$, $L^a$, $L^1$ to $L^4$, $R^a$, $R^1$ to $R^4$, $R^b$, and $R^c$ are the same as described above.

For example, Chemical Formula 1A-1 may be represented by one of Chemical Formula 1A-1-a to Chemical Formula 1A-1-d according to a specific substitution position of the group represented by Chemical Formula A.

[Chemical Formula 1A-1-a]

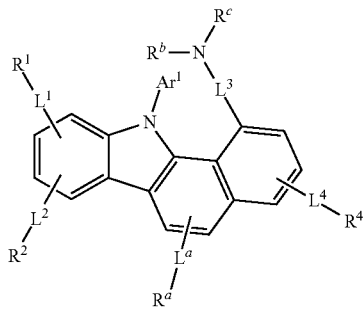

[Chemical Formula 1A-1-b]

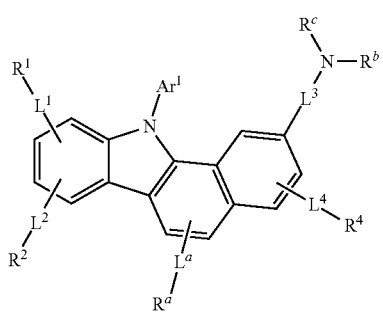

[Chemical Formula 1A-1-c]

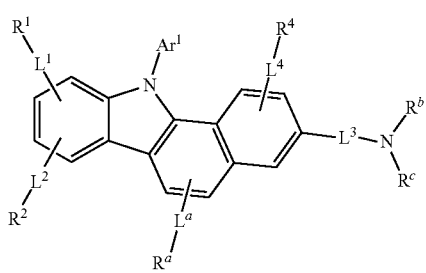

[Chemical Formula 1A-1-d]

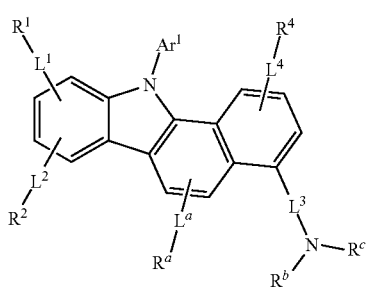

In Chemical Formula 1A-1-a to Chemical Formula 1A-1-d, $Ar^1$, $L^a$, $L^1$ to $L^4$, $R^a$, $R^1$ to $R^4$, $R^b$, and $R^c$ are the same as described above.

In an example embodiment, Chemical Formula 1A-1 may be represented by Chemical Formula 1A-1-b or Chemical Formula 1A-1-c.

For example, Chemical Formula 1A-2 may be represented by Chemical Formula 1A-2-a or Chemical Formula 1A-2-b according to a specific substitution position of the group represented by Chemical Formula A.

[Chemical Formula 1A-2-a]

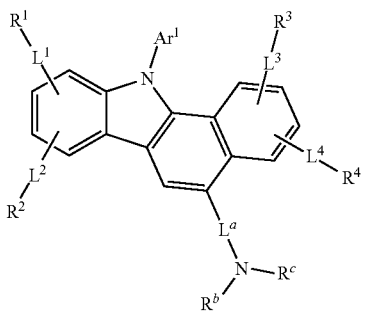

[Chemical Formula 1A-2-b]

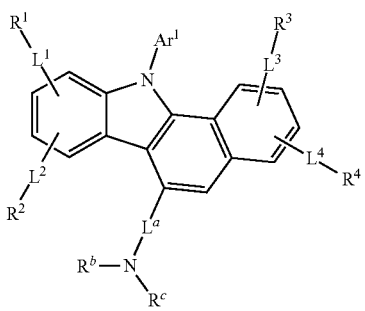

In Chemical Formula 1A-2-a and Chemical Formula 1A-2-b, $Ar^1$, $L^a$ and $L^1$ to $L^4$ and $R^1$ to $R^4$ and $R^b$ and $R^c$ are the same as described above.

In an example embodiment, Chemical Formula 1A-2 may be represented by Chemical Formula 1A-2-a.

For example, Chemical Formula 1A-3 may be represented by one of Chemical Formula 1A-3-a to Chemical Formula 1A-3-d according to a specific substitution position of the group represented by Chemical Formula A.

[Chemical Formula 1A-3-a]

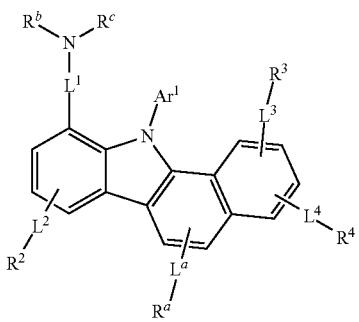

[Chemical Formula 1A-3-b]

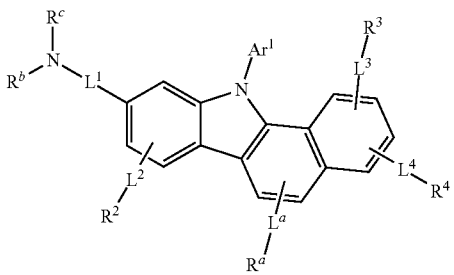

[Chemical Formula 1A-3-c]

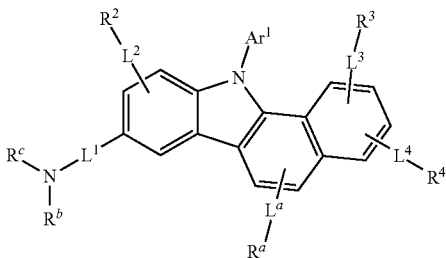

[Chemical Formula 1A-3-d]

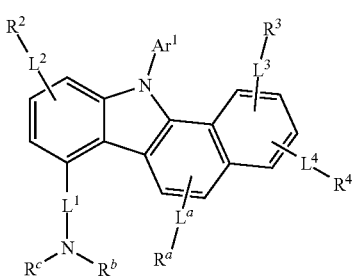

In Chemical Formula 1A-3-a to Chemical Formula 1A-3-d, $Ar^1$, $L^a$, $L^1$ to $L^4$, $R^a$, $R^1$ to $R^4$, $R^b$, and $R^c$ are the same as described above.

In an example embodiment, Chemical Formula 1A-3 may be represented by Chemical Formula 1A-3-b or Chemical Formula 1A-3-c.

For example, Chemical Formula 1B may be represented by one of Chemical Formula 1B-1 to Chemical Formula 1B-3 according to a substitution position of the group represented by Chemical Formula A.

[Chemical Formula 1B-1]

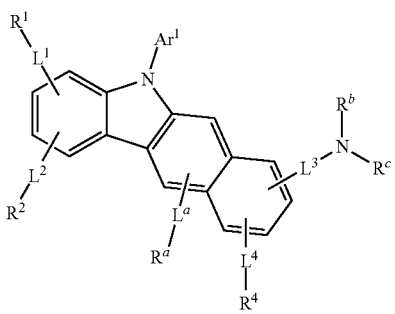

[Chemical Formula 1B-2]

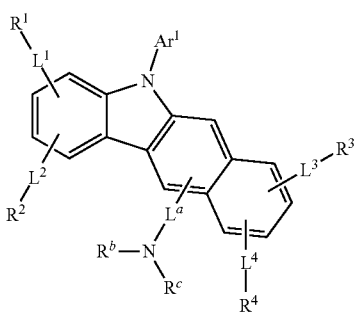

[Chemical Formula 1B-3]

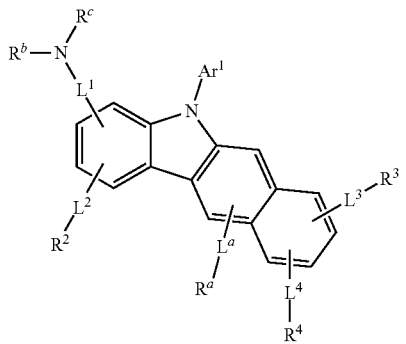

In Chemical Formula 1B-1 to Chemical Formula 1B-3, $Ar^1$, $L^a$, $L^1$ to $L^4$, $R^a$, $R^1$ to $R^4$, $R^b$, and $R^c$ are the same as described above.

For example, Chemical Formula 1B-1 may be represented by one of Chemical Formula 1B-1-a to Chemical Formula 1B-1-d according to a specific substitution position of the group represented by Chemical Formula A.

[Chemical Formula 1B-1-a]

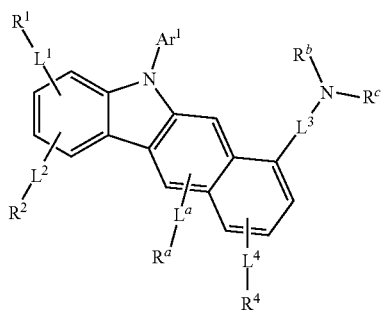

[Chemical Formula 1B-1-b]

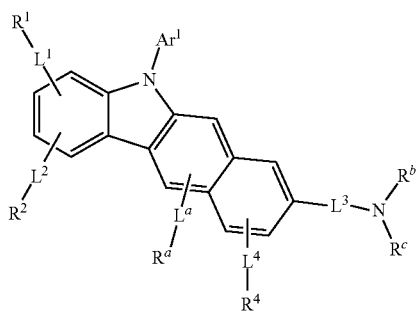

[Chemical Formula 1B-1-c]

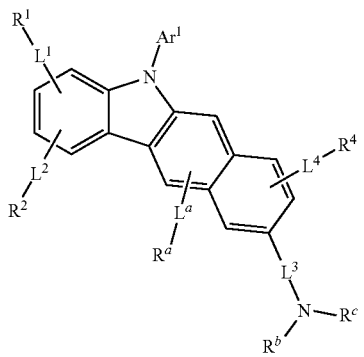

[Chemical Formula 1B-1-d]

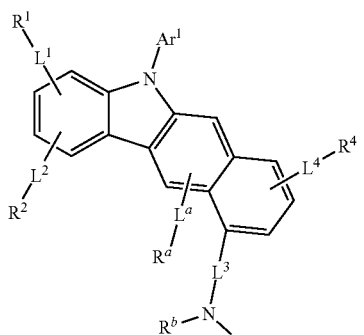

In Chemical Formula 1B-1-a to Chemical Formula 1B-1-d, $Ar^1$, $L^a$, $L$ to $L^4$, $R^a$, $R^1$ to $R^4$, $R^b$, and $R^c$ are the same as described above.

For example, Chemical Formula 1B-2 may be represented by Chemical Formula 1B-2-a or Chemical Formula 1B-2-b according to a specific substitution position of the group represented by Chemical Formula A.

[Chemical Formula 1B-2-a]

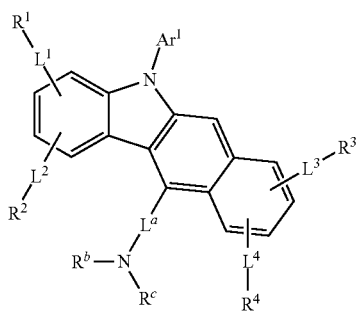

[Chemical Formula 1B-2-b]

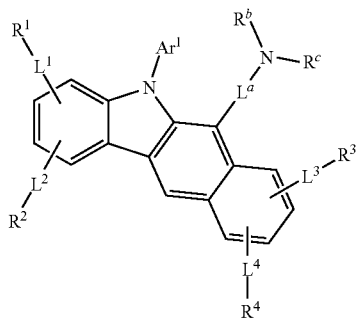

[Chemical Formula 1B-3-d]

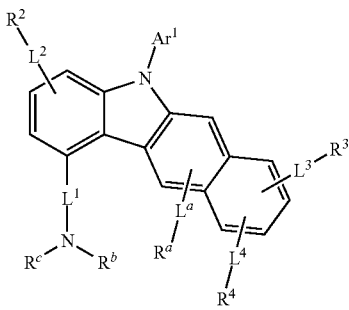

In Chemical Formula 1B-2-a and Chemical Formula 1B-2-b, $Ar^1$, $L^a$, $L^1$ to $L^4$, $R^1$ to $R^4$, $R^b$, and $R^c$ are the same as described above.

For example, Chemical Formula 1B-3 may be represented by one of Chemical Formula 1B-3-a to Chemical Formula 1B-3-d according to a specific substitution position of the group represented by Chemical Formula A.

In Chemical Formula 1B-3-a to Chemical Formula 1B-3-d, $Ar^1$, $L^a$, $L^1$ to $L^4$, $R^a$, $R^1$ to $R^4$, $R^b$, and $R^c$ are the same as described above.

In an embodiment, Chemical Formula 1B-3 may be represented by Chemical Formula 1B-3-b.

For example, Chemical Formula 1C may be represented by one of Chemical Formula 1C-1 to Chemical Formula 1C-3 according to a substitution position of the group represented by Chemical Formula A.

[Chemical Formula 1B-3-a]

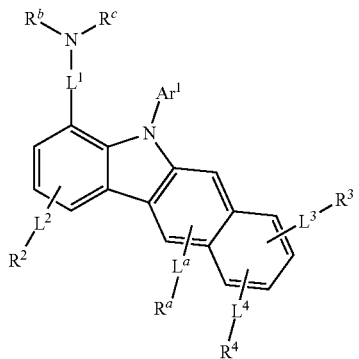

[Chemical Formula 1C-1]

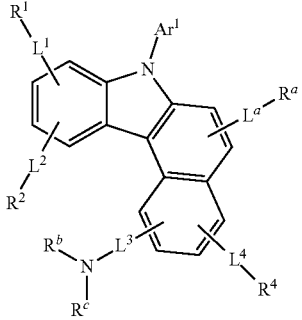

[Chemical Formula 1B-3-b]

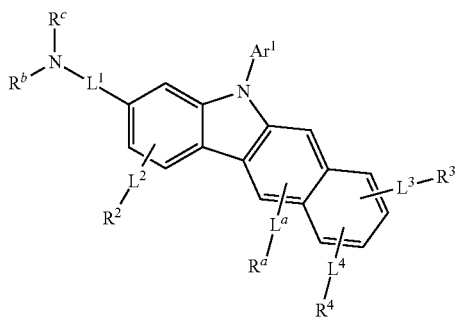

[Chemical Formula 1B-3-c]

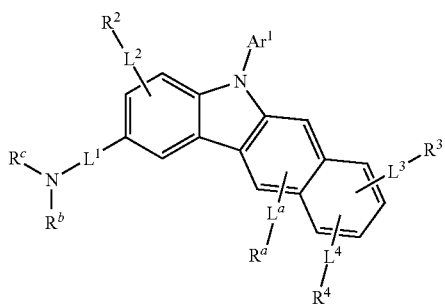

[Chemical Formula 1C-2]

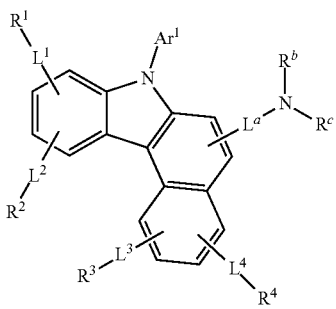

[Chemical Formula 1C-3]

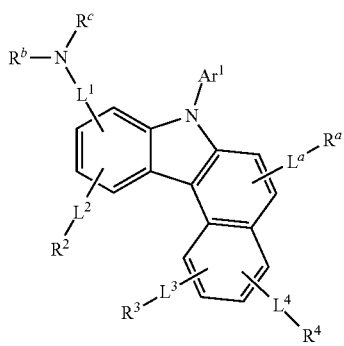

In Chemical Formula 1C-1 to Chemical Formula 1C-3, $Ar^1$, $L^a$, $L^1$ to $L^4$, $R^a$, $R^1$ to $R^4$, $R^b$, and $R^c$ are the same as described above.

For example, Chemical Formula 1C-1 may be represented by one of Chemical Formula 1C-1-a to Chemical Formula 1C-1-d according to a specific substitution position of the group represented by Chemical Formula A.

[Chemical Formula 1C-1-a]

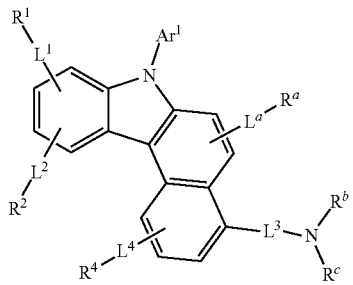

[Chemical Formula 1C-1-b]

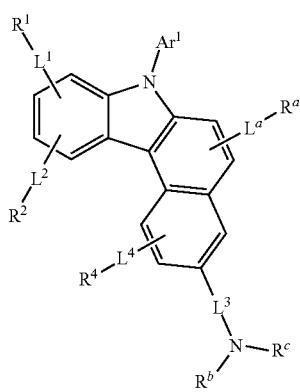

[Chemical Formula 1C-1-c]

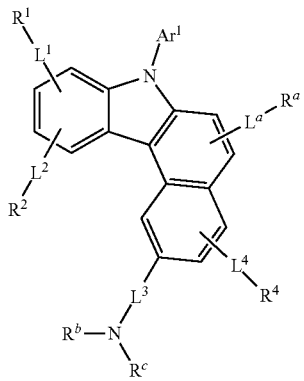

[Chemical Formula 1C-1-d]

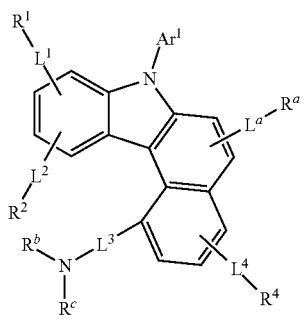

In Chemical Formula 1C-1-a to Chemical Formula 1C-1-d, $Ar^1$, $L^a$, L to $L^4$, $R^a$, $R^1$ to $R^4$, $R^b$, and $R^c$ are the same as described above.

In an embodiment, Chemical Formula 1C-1 may be represented by Chemical Formula 1C-1-b.

For example, Chemical Formula 1C-2 may be represented by one of Chemical Formula 1C-2-a or Chemical Formula 1C-2-b according to a specific substitution position of the group represented by Chemical Formula A.

[Chemical Formula 1C-2-a]

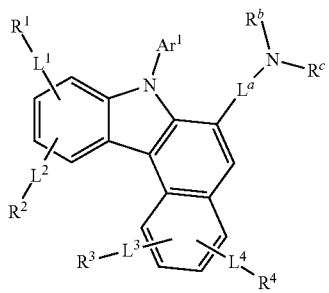

[Chemical Formula 1C-2-b]

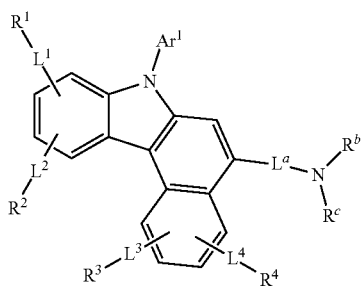

In Chemical Formula 1C-2-a and Chemical Formula 1C-2-b, $Ar^1$, $L^a$, $L^1$ to $L^4$, $R^1$ to $R^4$, $R^b$, and $R^c$ are the same as described above.

For example, Chemical Formula 1C-3 be represented by one of Chemical Formula 1C-3-a to Chemical Formula 1C-3-d according to a specific substitution position of the group represented by Chemical Formula A.

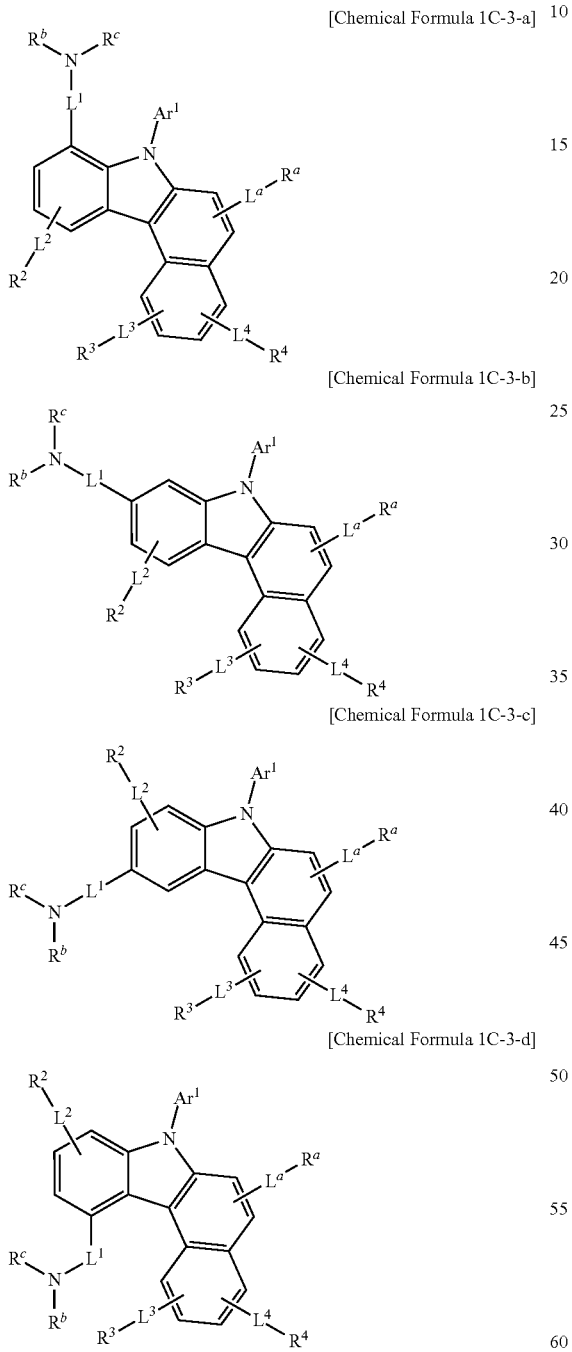

[Chemical Formula 1C-3-a]

[Chemical Formula 1C-3-b]

[Chemical Formula 1C-3-c]

[Chemical Formula 1C-3-d]

In Chemical Formula 1C-3-a to Chemical Formula 1C-3-d, $Ar^1$, $L^a$, $L^1$ to $L^4$, $R^a$, $R^1$ to $R^4$, $R^b$, and $R^c$ are the same as described above.

In an embodiment, Chemical Formula 1C-3 may be represented by Chemical Formula 1C-3-b.

In a specific embodiment of the present invention, the first compound may be represented by Chemical Formula 1A, and specifically Chemical Formula 1A-1, for example Chemical Formula 1A-1-b.

The first compound may be for example one of compounds of Group 1, but is not limited thereto.

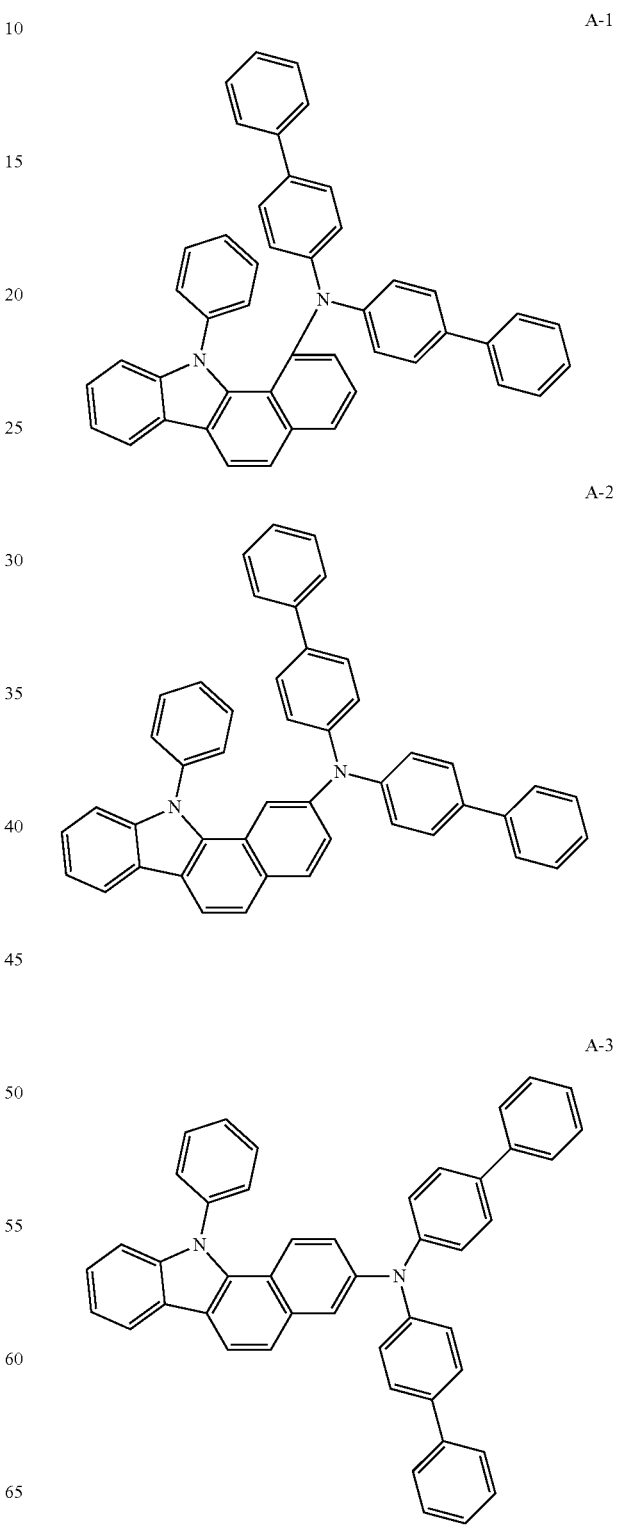

A-1

A-2

A-3

A-4
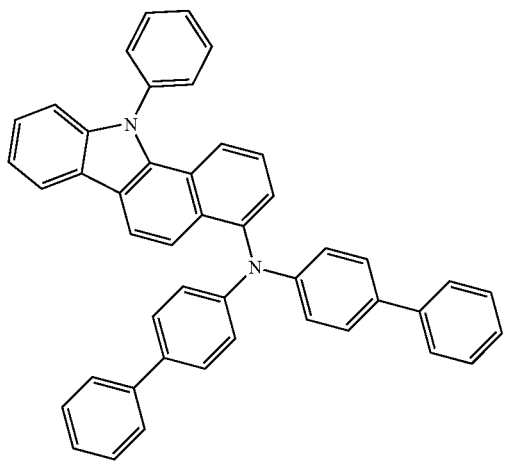
A-7
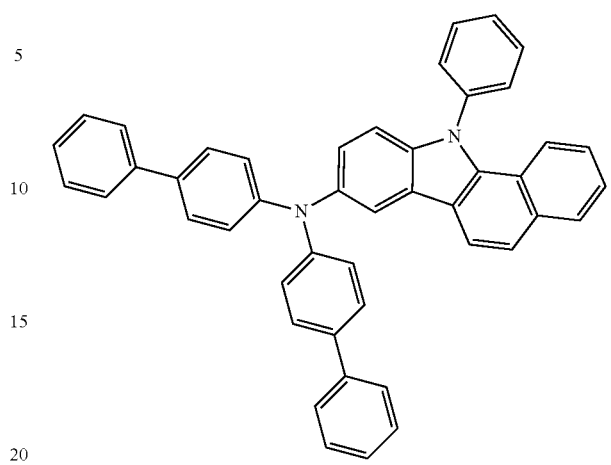
A-5
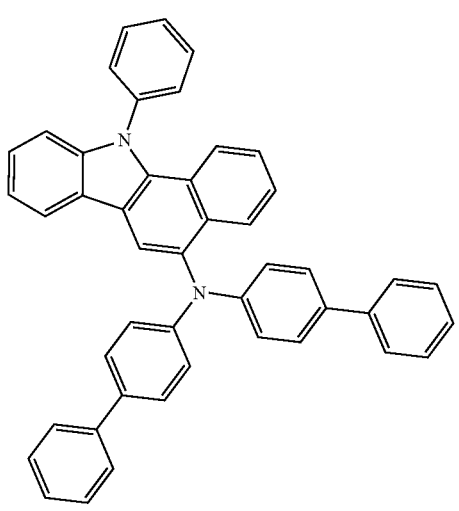
A-8
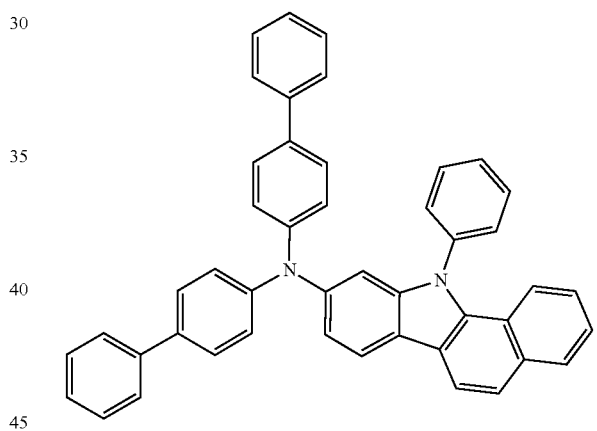
A-6
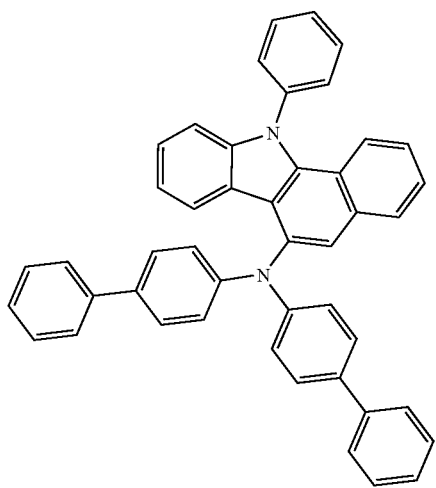
A-9
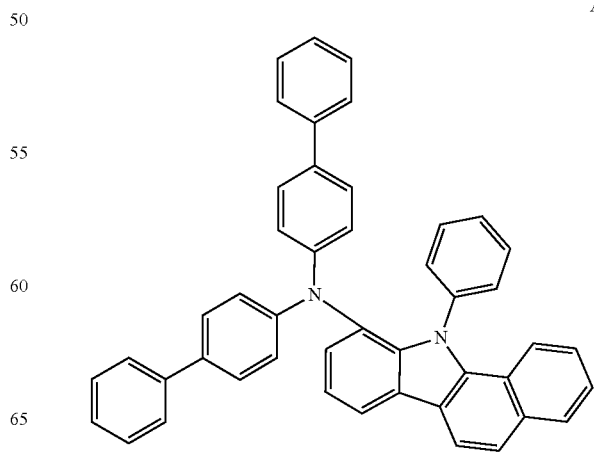

A-10
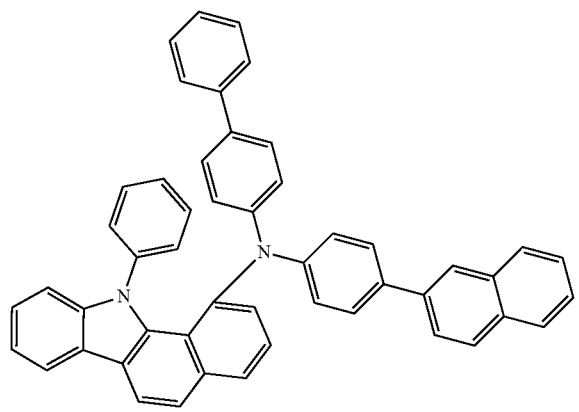
A-13
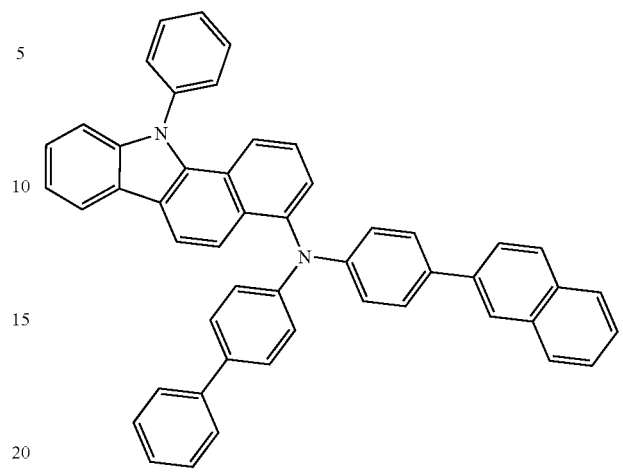
A-11
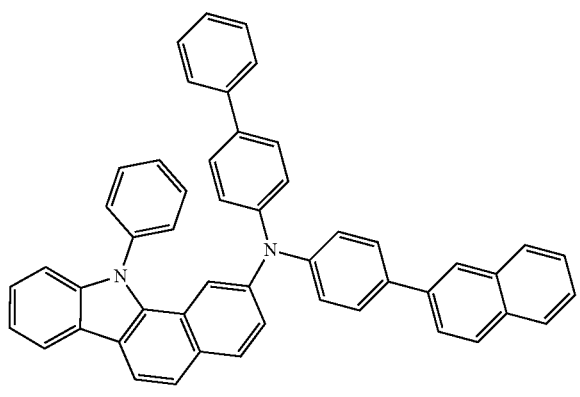
A-14
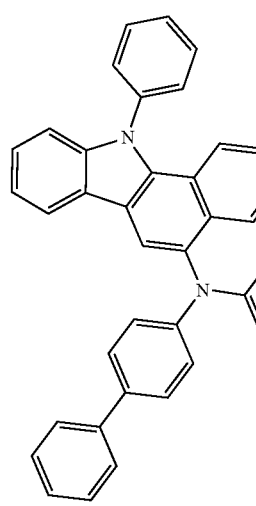
A-12
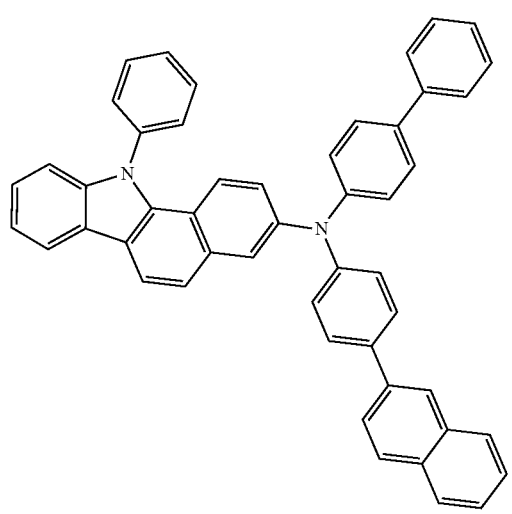
A-15
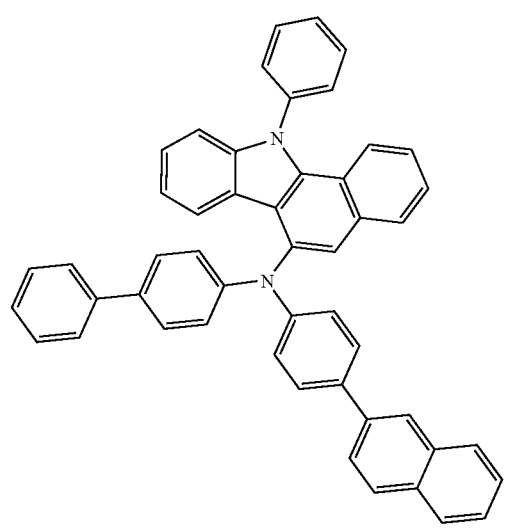

A-16
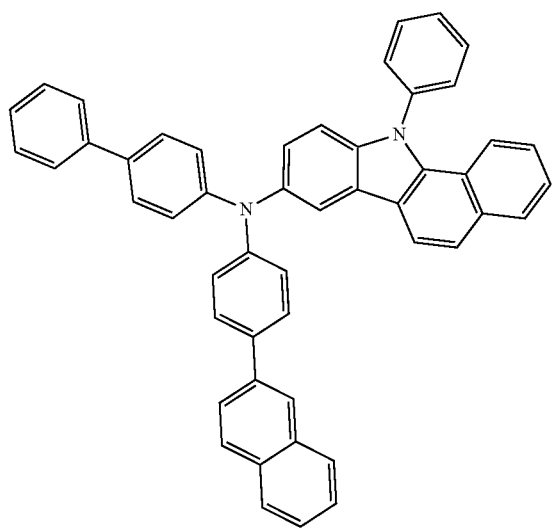
A-17
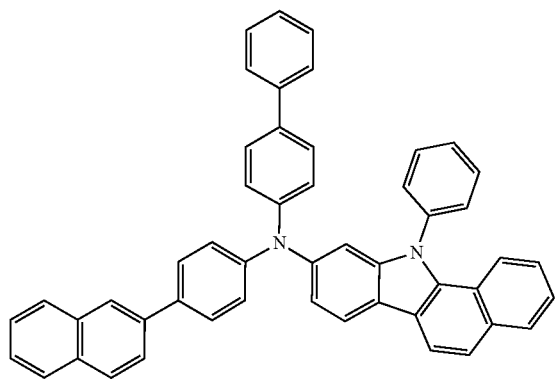
A-18
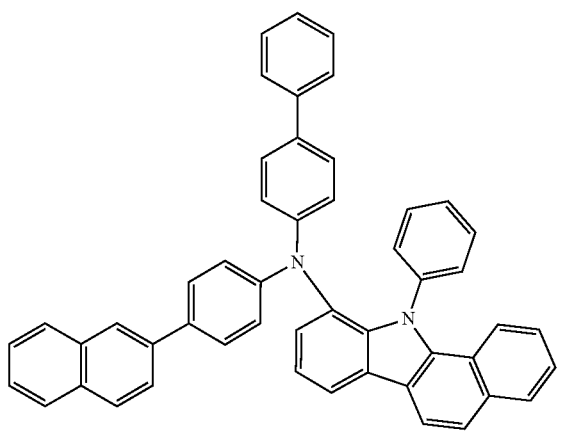
A-19
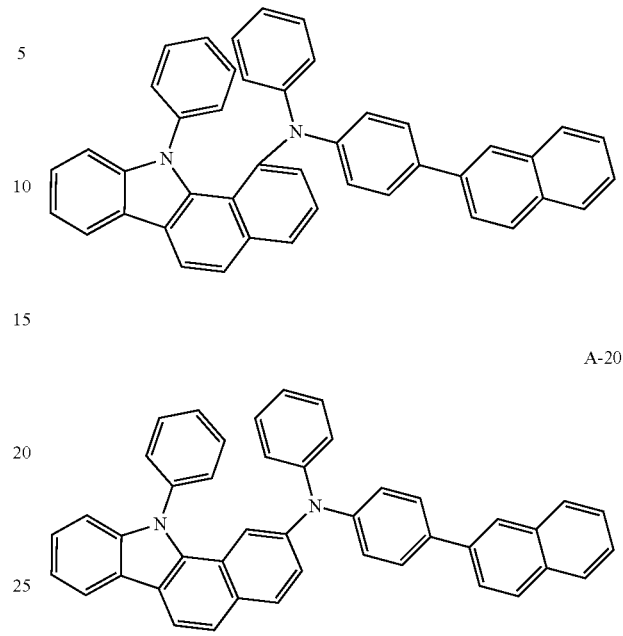
A-20
A-21
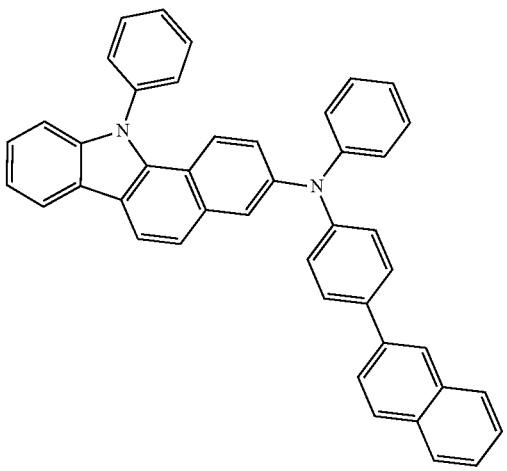
A-22
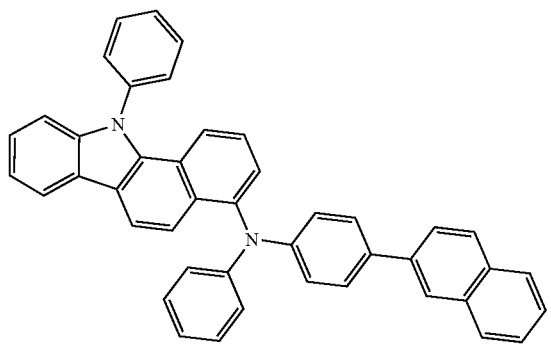

A-23
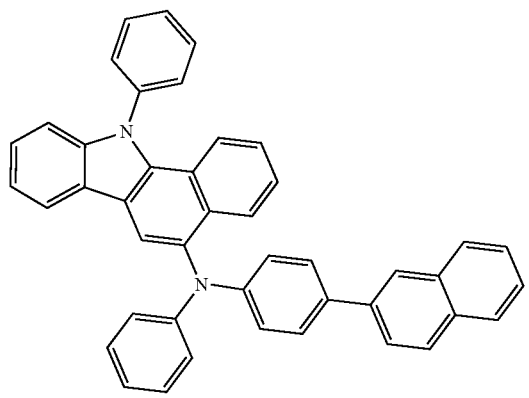
A-24
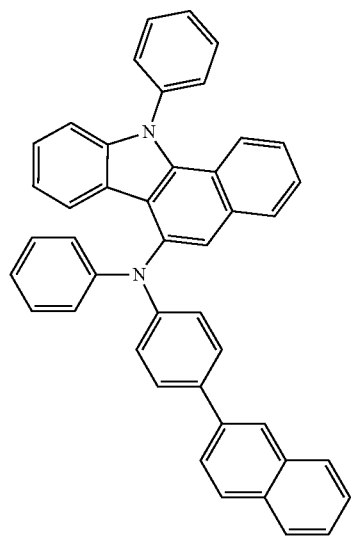
A-25
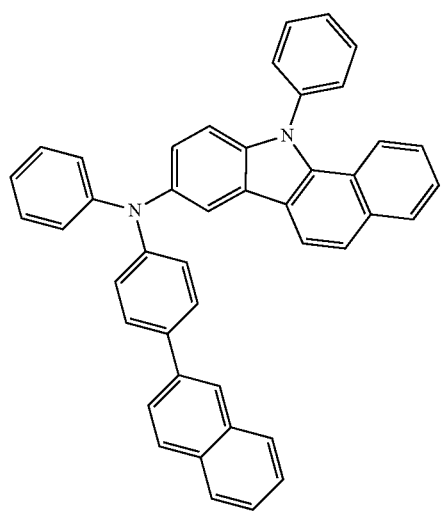
A-26
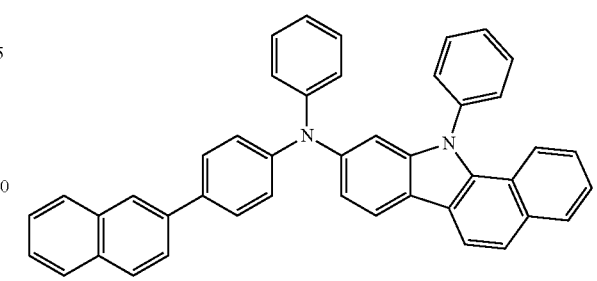
A-27
A-28
A-29
A-30
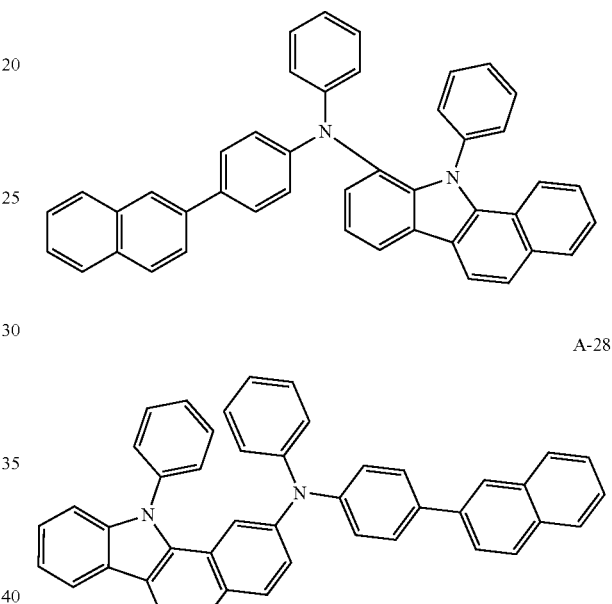
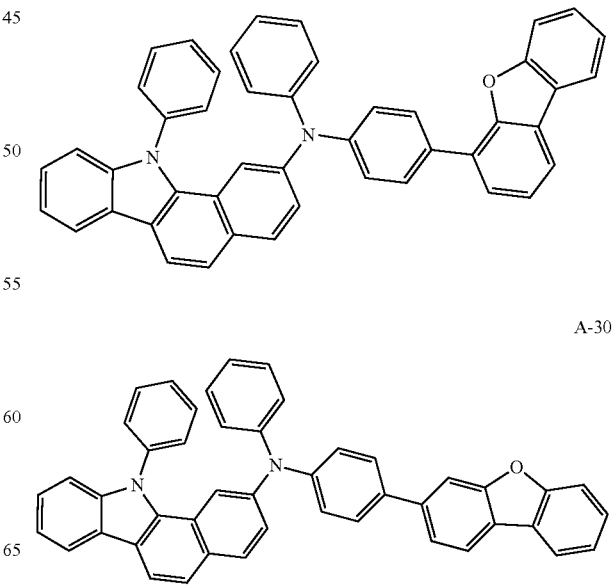

A-31
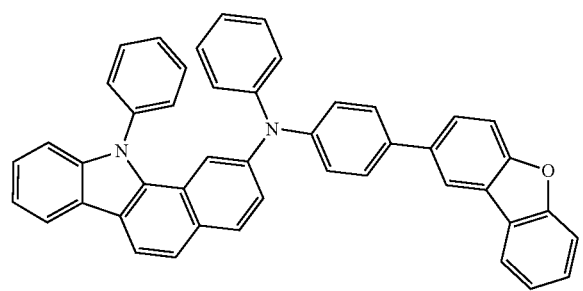
A-32
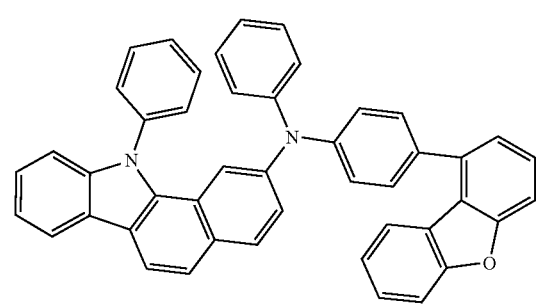
A-33
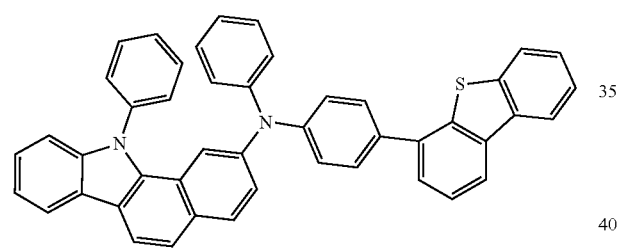
A-34
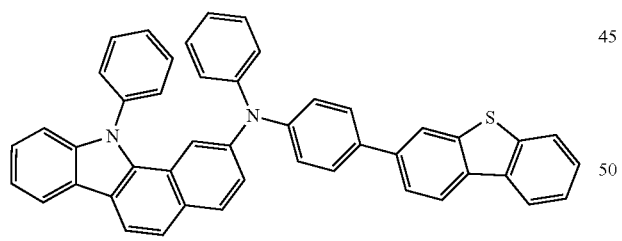
A-35
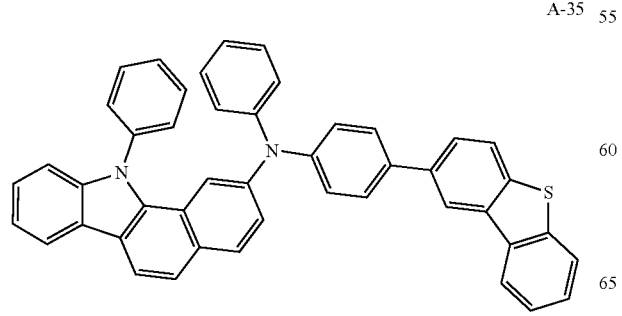
A-36
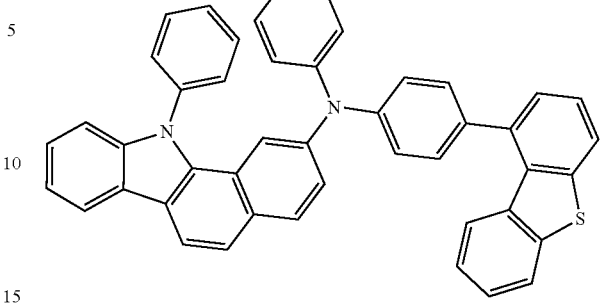
A-37
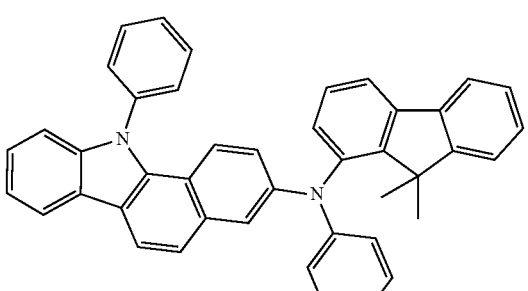
A-38
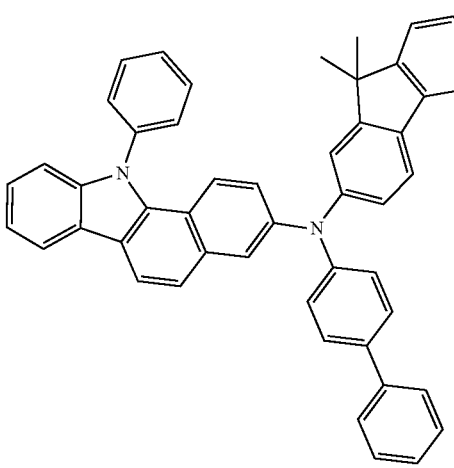

A-39
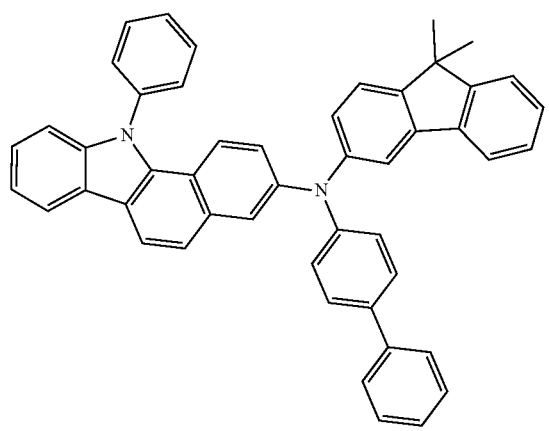
A-42
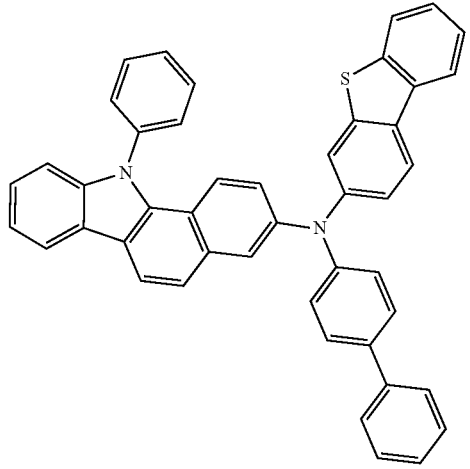
A-40
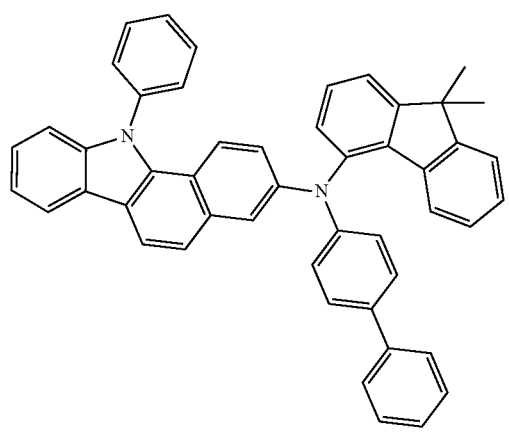
A-43
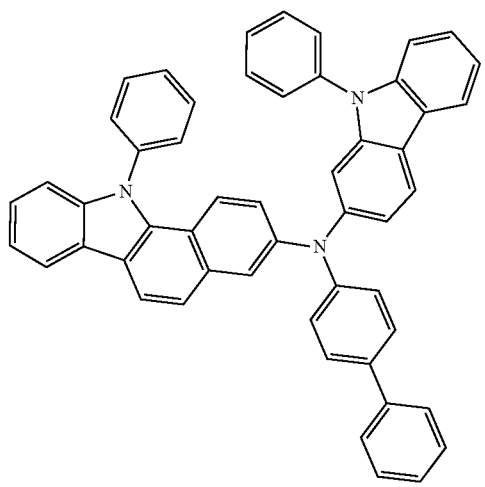
A-41
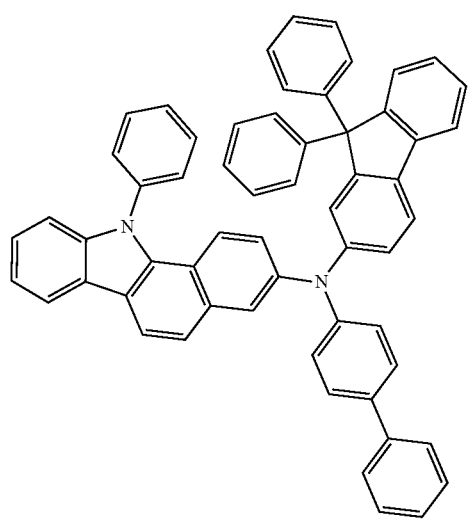
A-44
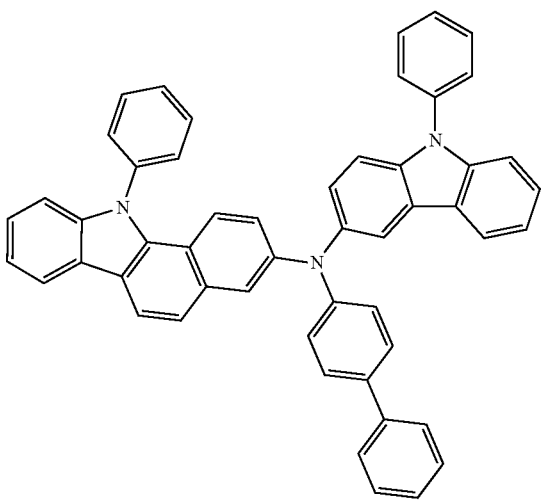

A-45
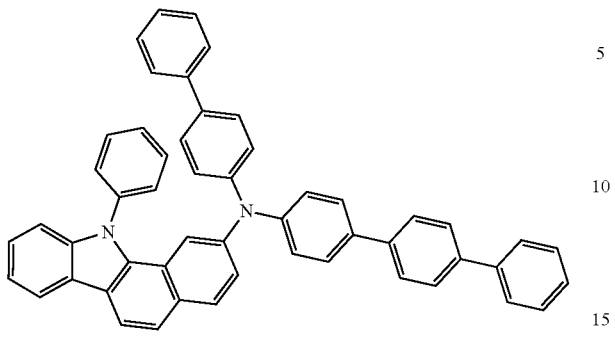
A-46
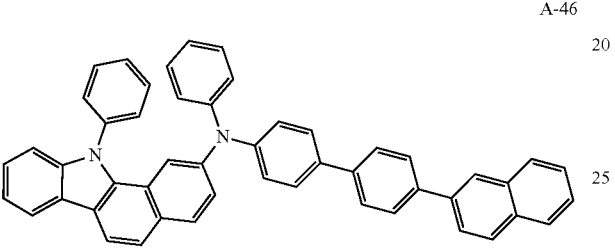
A-47
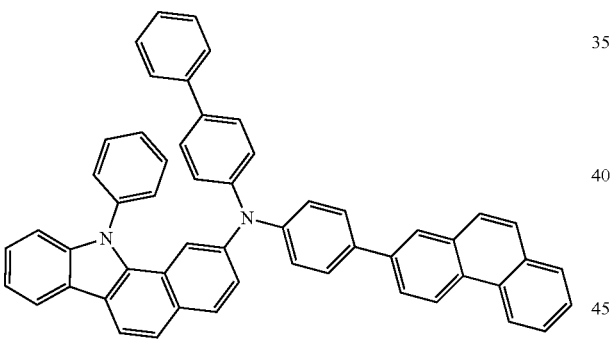
A-48
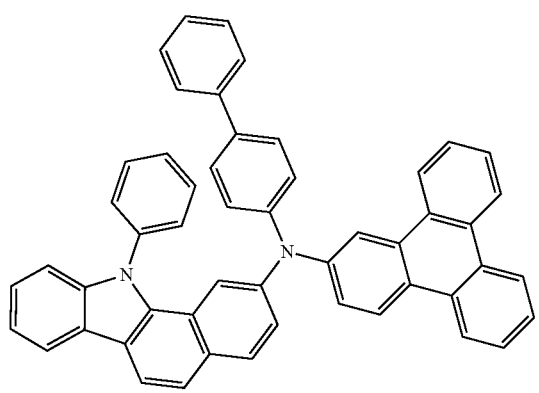
A-49
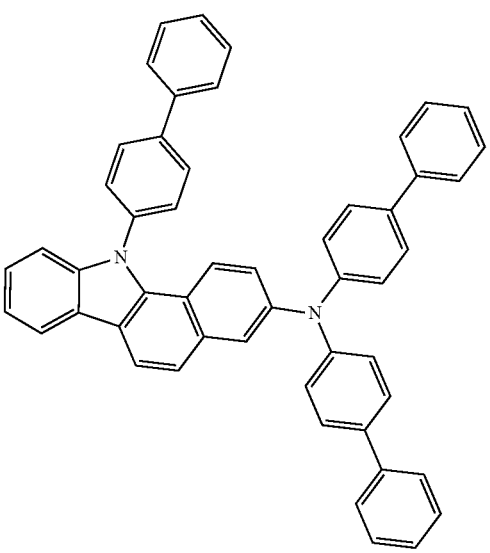
A-50
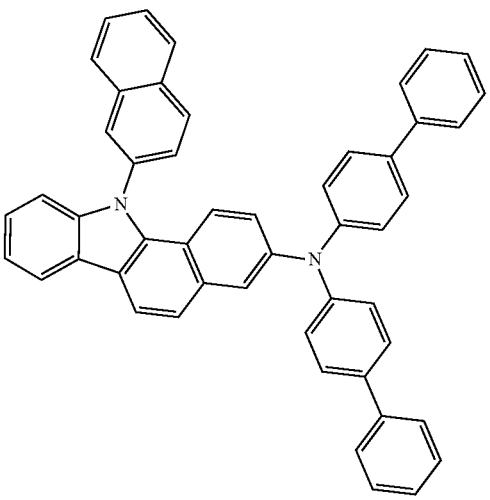
A-51
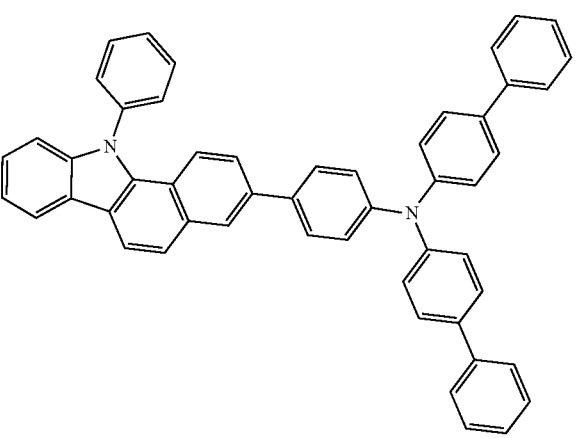

A-52
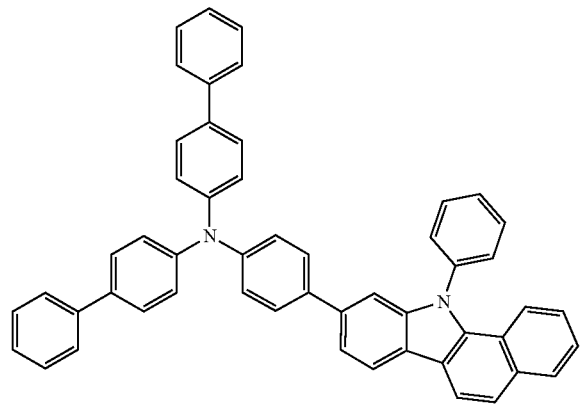
A-53
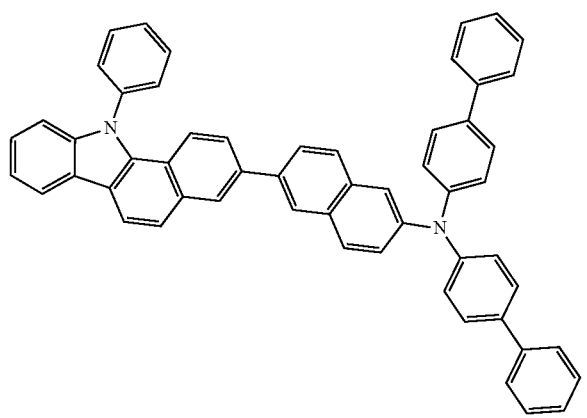
A-54
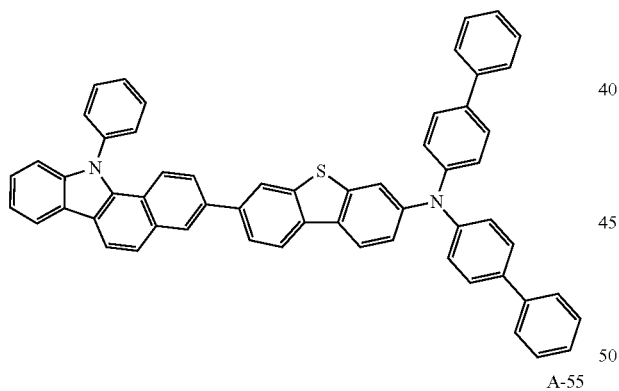
A-55
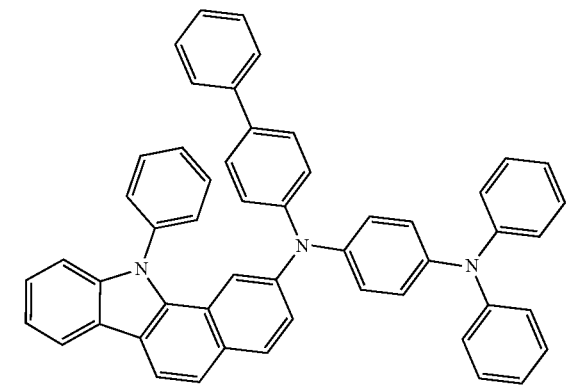
A-56
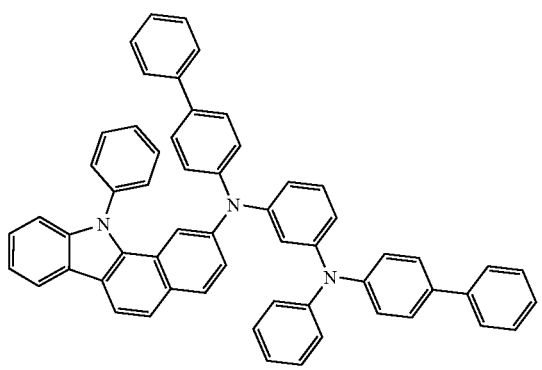
A-57
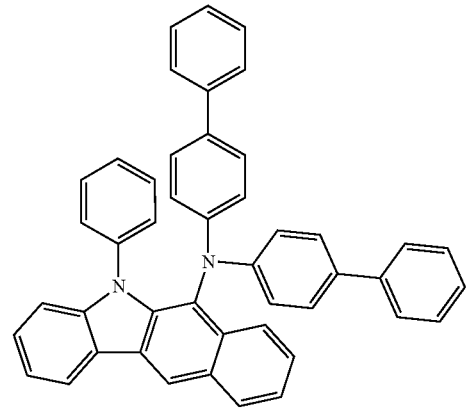
A-58
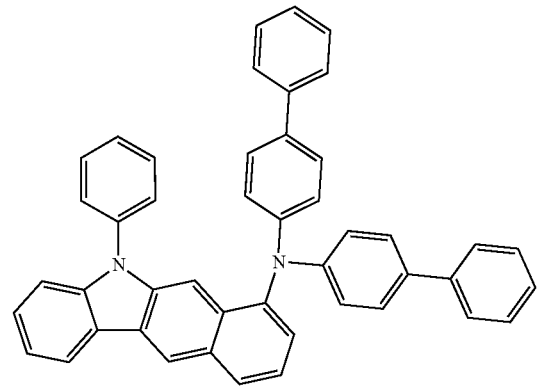
A-59
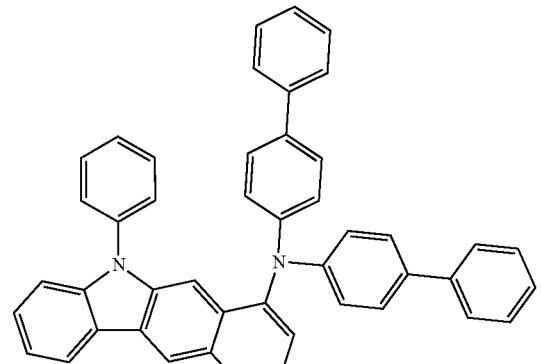

A-60
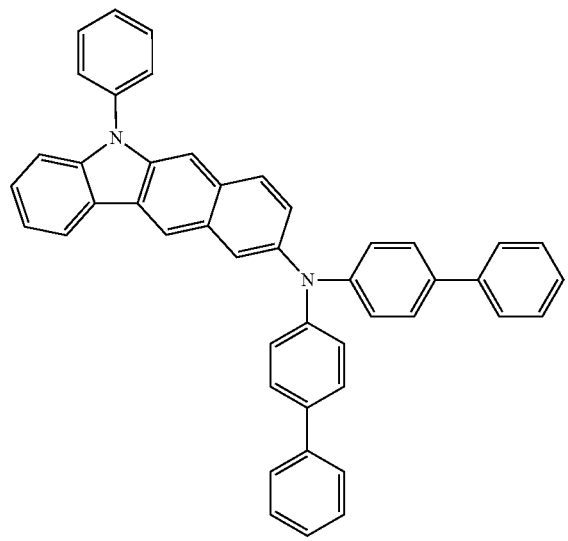
A-61
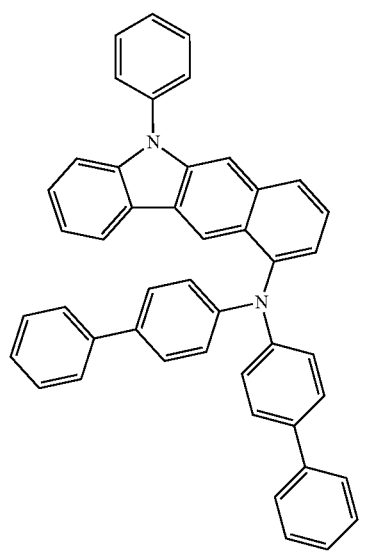
A-62
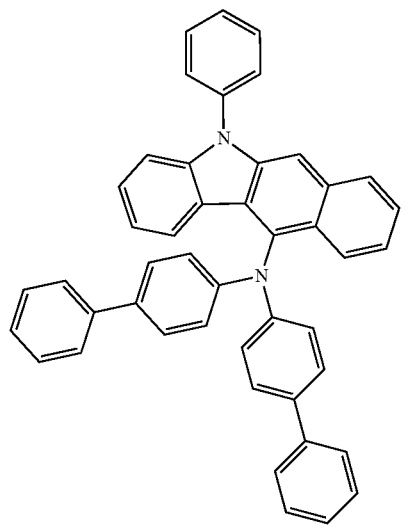
A-63
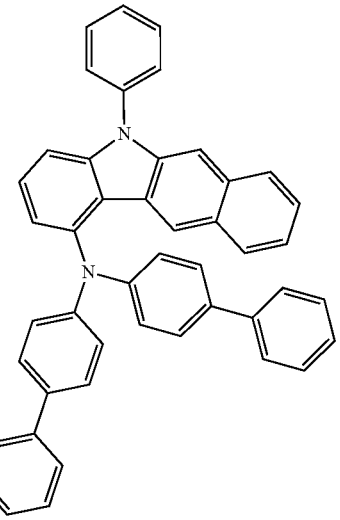
A-64
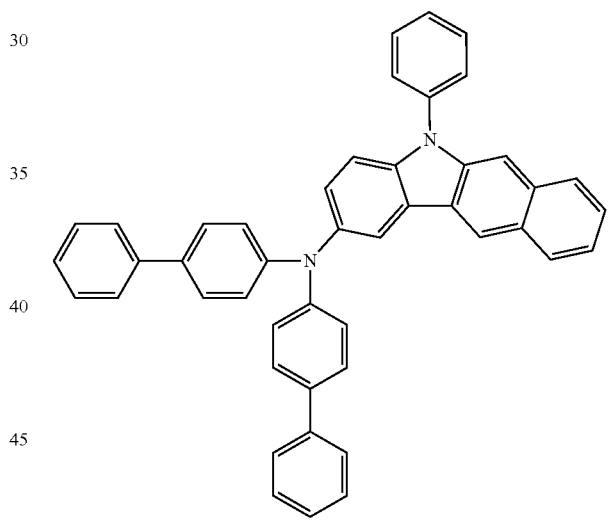
A-65
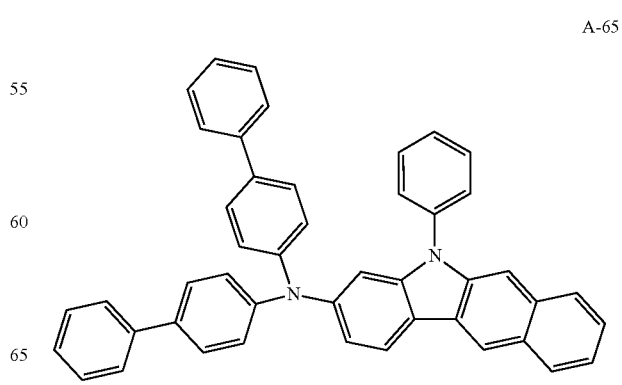

A-66
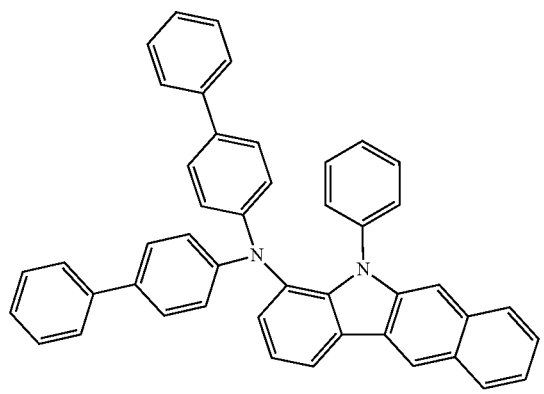
A-67
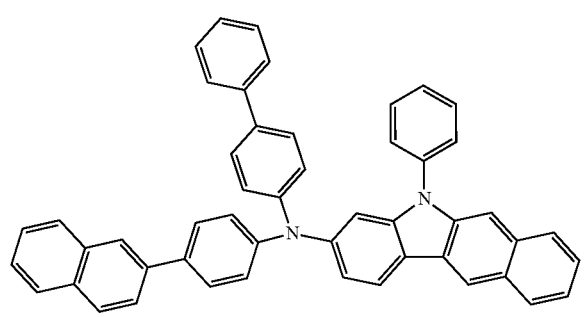
A-68
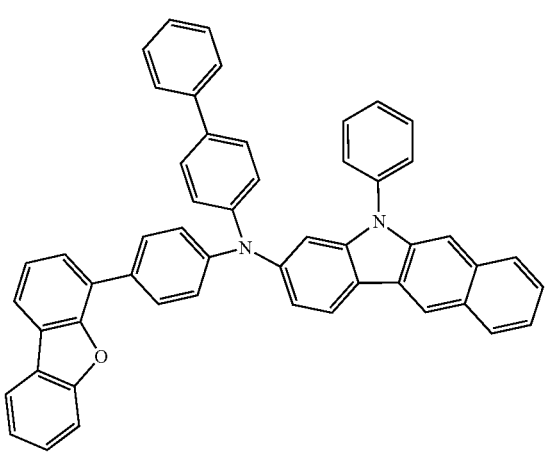
A-69
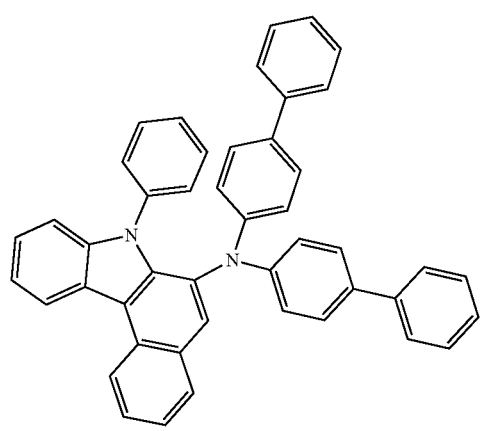
A-70
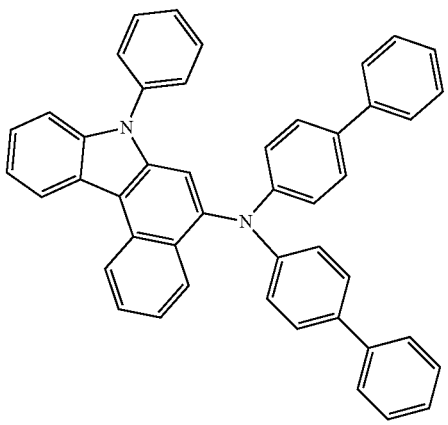
A-71
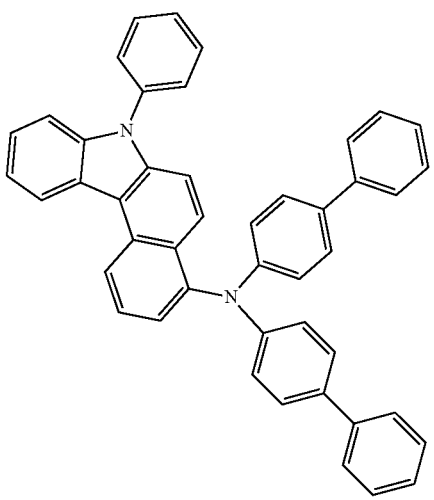
A-72
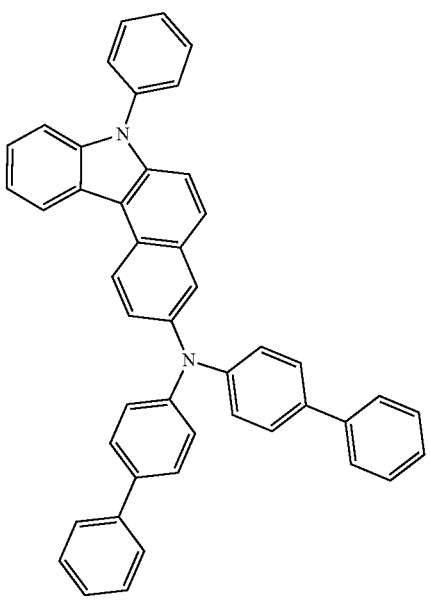

A-73
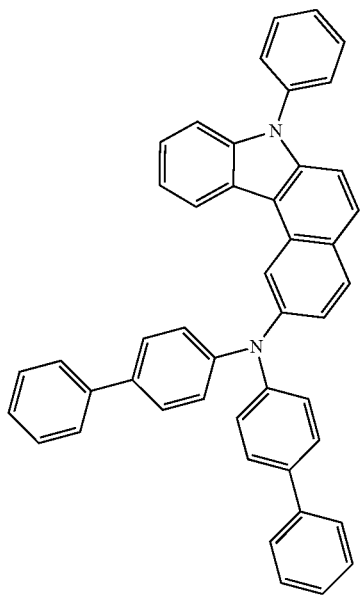
A-74
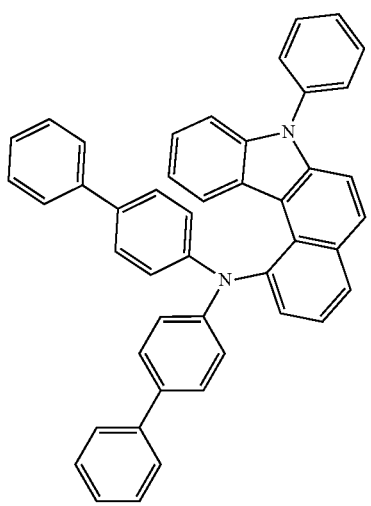
A-75
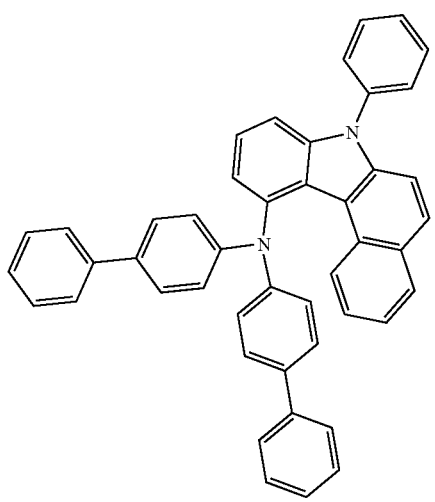
A-76
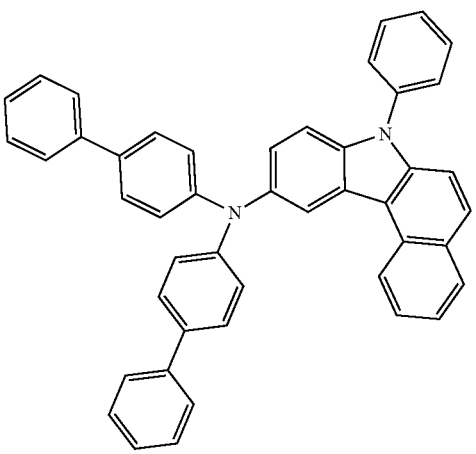
A-77
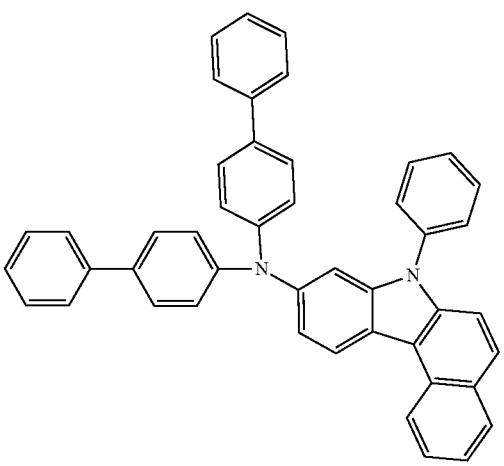
A-78
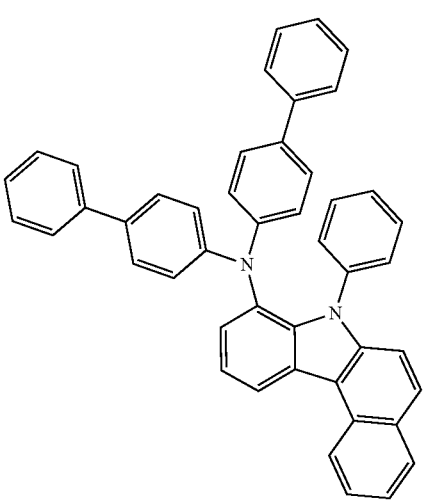

-continued
A-79
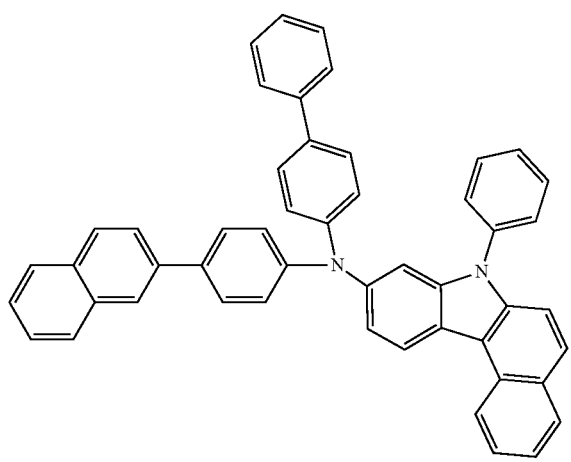
A-80
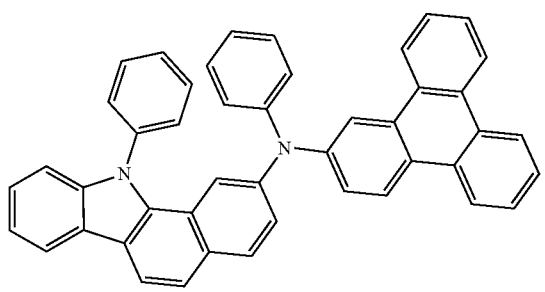
A-81
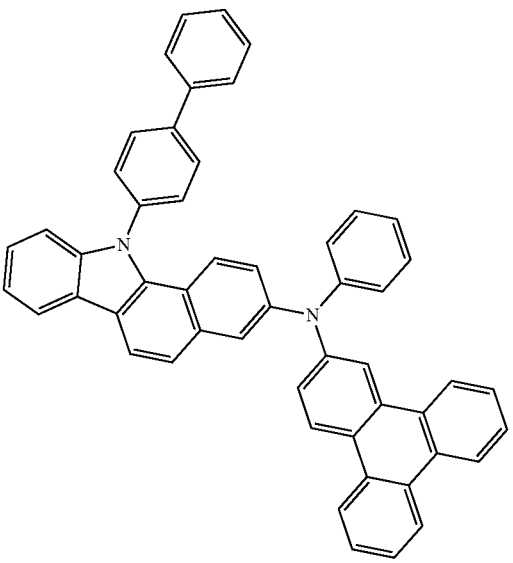
-continued
A-82
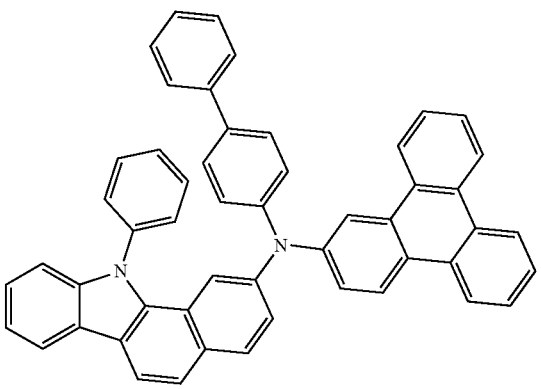
A-83
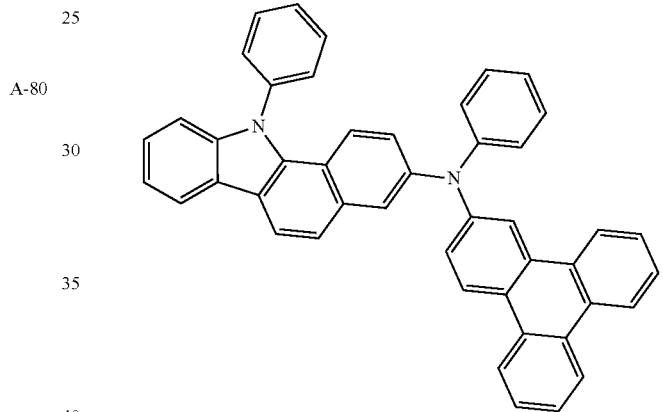
A-84

A-85

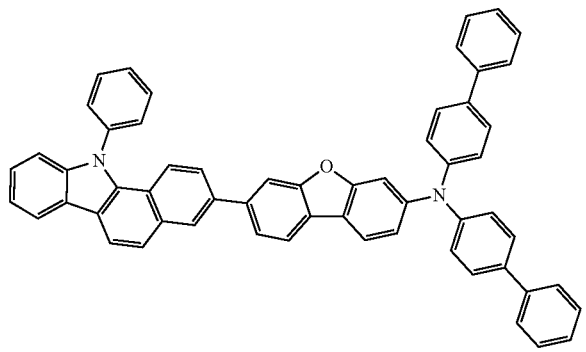

A-86

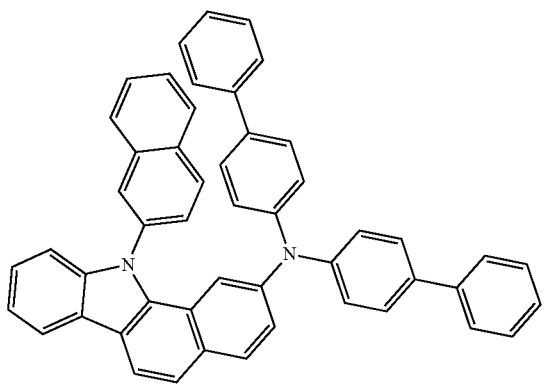

A-87

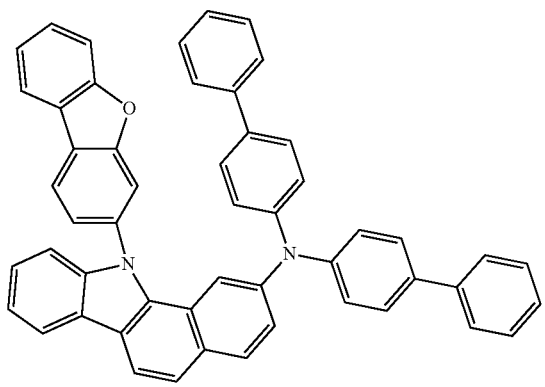

A-88

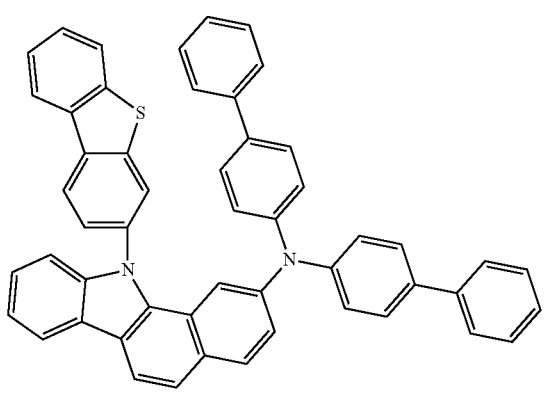

A-89

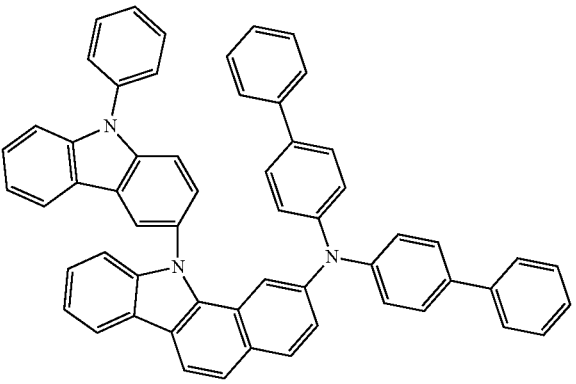

The second compound is represented by Chemical Formula 3.

[Chemical Formula 3]

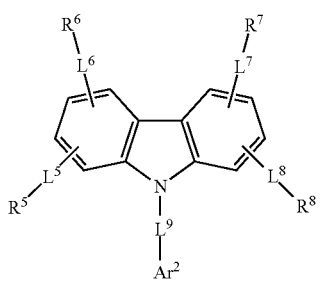

In Chemical Formula 3,

L⁵ to L⁹ are independently a single bond, a substituted or unsubstituted C6 to C20 arylene group, a substituted or unsubstituted C2 to C20 heterocyclic group, or a combination thereof, Ar² is a substituted or unsubstituted C6 to C30 aryl group, a substituted or unsubstituted C2 to C30 heterocyclic group, or a combination thereof, R⁵ to R$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, R⁵ to R⁸ are independently present or adjacent groups thereof are linked with each other to form a substituted or unsubstituted aromatic monocyclic or polycyclic ring, at least one of Ar² and R⁵ to R⁸ is a group represented by Chemical Formula B,

[Chemical Formula B]

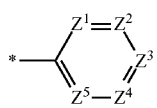

wherein, in Chemical Formula B, $Z^1$ to $Z^5$ are independently N or $C-L^b-R^d$, at least one of $Z^1$ to $Z^5$ is N, wherein $L^b$ is independently a single bond, a substituted or unsubstituted C6 to C20 arylene group, a substituted or unsubstituted C2 to C20 heterocyclic group, or a combination thereof, $R^d$ is independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $R^d$ is independently present or adjacent groups thereof are linked with each other to form a substituted or unsubstituted aromatic monocyclic or polycyclic ring, or a substituted or unsubstituted aromatic monocyclic or polycyclic heteroring, and

* is a linking point with $L^5$ to $L^9$.

The second compound is a compound capable of accepting both holes and electrons when an electric field is applied, that is, a compound having bipolar characteristics, and specifically, may have an effect of improving the glass transition temperature relative to the molecular weight and ensure heat resistance due to the carbazol core represented by Formula 3 substituted with a ring including at least one nitrogen, for example a pyrimidine or triazine.

In addition, the second compound has fast and stable electron transport characteristics, thus may match a balance of holes and electrons by being included with the first compound having fast and stable hole transport characteristics, and may lower a driving voltage of an organic optoelectronic device including the same.

For example, $L^5$ to $L^9$ may independently be a single bond, a substituted or unsubstituted C6 to C20 arylene group, or a substituted or unsubstituted C2 to C20 heterocyclic group.

For example, $L^5$ to $L^9$ may independently be a single bond, a substituted or unsubstituted phenylene group, a substituted or unsubstituted biphenylene group, a substituted or unsubstituted terphenylene group, a substituted or unsubstituted naphthylene group, a substituted or unsubstituted dibenzofuranyl group, a substituted or unsubstituted dibenzothiophenyl group, a substituted or unsubstituted fused dibenzofuranyl group, a substituted or unsubstituted fused dibenzothiophenyl group, or a combination thereof.

For example, $L^5$ to $L^9$ may independently be a single bond, a substituted or unsubstituted m-phenylene group, a substituted or unsubstituted p-phenylene group, a substituted or unsubstituted biphenylene group, or a substituted or unsubstituted terphenylene group.

For example, $Ar^2$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, the group represented by Chemical Formula B, or a combination thereof.

For example, $Ar^2$ may be a substituted or unsubstituted phenyl group, a substituted or unsubstituted biphenyl group, a substituted or unsubstituted naphthyl group, a substituted or unsubstituted fluorenyl group, or the group represented by Chemical Formula B, but is not limited thereto.

For example, $R^5$ to $R^8$ may independently be hydrogen, deuterium, a cyano group, a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, the group represented by Chemical Formula B, or a combination thereof.

For example, $R^5$ to $R^8$ may independently be hydrogen, deuterium, a cyano group, a substituted or unsubstituted phenyl group, a substituted or unsubstituted biphenyl group, a substituted or unsubstituted terphenyl group, a substituted or unsubstituted naphthyl group, a substituted or unsubstituted dibenzofuranyl group, a substituted or unsubstituted dibenzothiophenyl group or the group represented by Chemical Formula B, but is not limited thereto.

For example, the second compound may be represented by one of, for example Chemical Formula 2A to Chemical Formula 2L according to a binding position of the group represented by Chemical Formula B.

[Chemical Formula 2A]

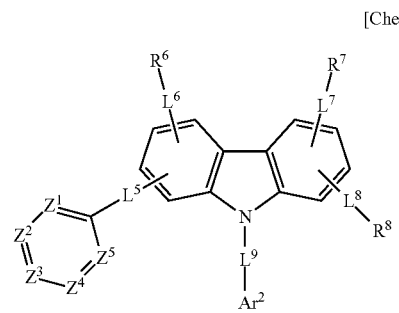

[Chemical Formula 2B]

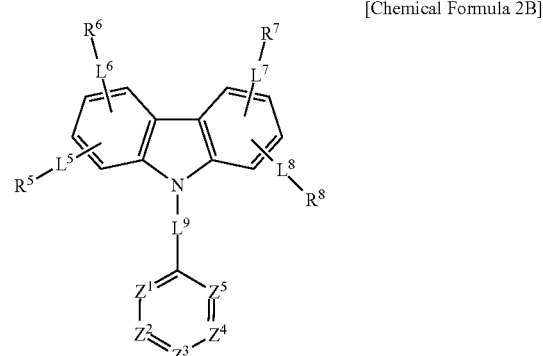

[Chemical Formula 2C]

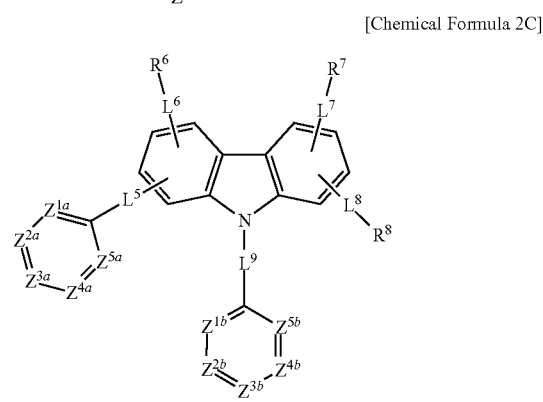

[Chemical Formula 2D]
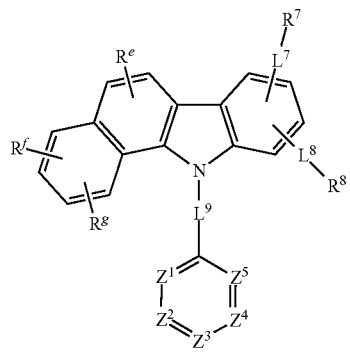
[Chemical Formula 2E]
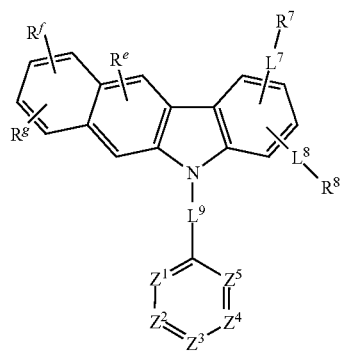
[Chemical Formula 2F]
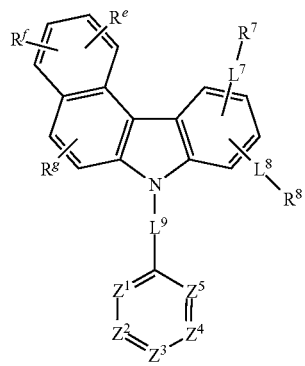
[Chemical Formula 2G]
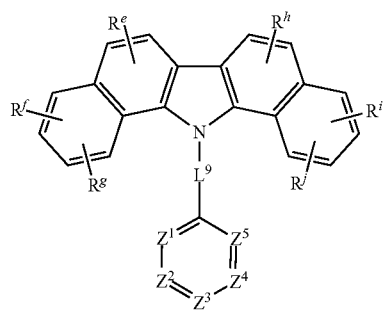
[Chemical Formula 2H]
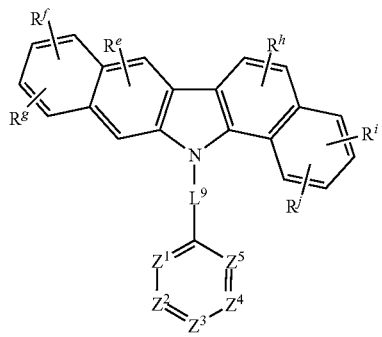
[Chemical Formula 2I]
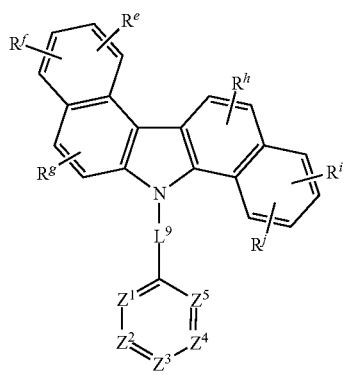
[Chemical Formula 2J]
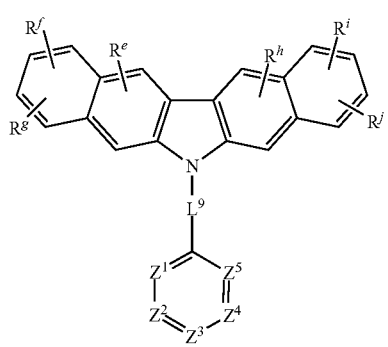
[Chemical Formula 2K]
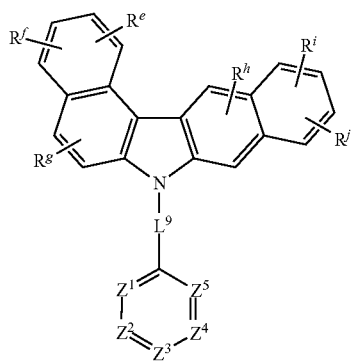

[Chemical Formula 2L]

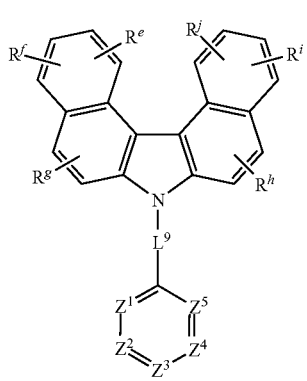

In Chemical Formulae 2A to 2L, $L^5$ to $L^9$, $Ar^2$, $R^5$ to $R^8$, and $Z^1$ to $Z^5$ are the same as described above, $R^e$, $R^f$, $R^g$, $R^h$, $R^i$, and $R^j$ are the same as $R^5$ to $R^8$, $Z^{1a}$ to $Z^{5a}$ are the same as $Z^1$ to $Z^5$, and $Z^{1b}$ to $Z^{5b}$ are the same as $Z^1$ to $Z^5$.

For example, $L^b$ may independently be a single bond, a substituted or unsubstituted C6 to C20 arylene group, a substituted or unsubstituted C2 to C20 heterocyclic group, or a combination thereof, for example $L^b$ may independently be a single bond, a substituted or unsubstituted phenylene group, a substituted or unsubstituted biphenylene group, a substituted or unsubstituted terphenylene group, a substituted or unsubstituted fluorenylene group, a substituted or unsubstituted dibenzofuranylene group, or a substituted or unsubstituted dibenzothiophenylene group.

For example, $L^b$ may independently be a single bond, a substituted or unsubstituted m-phenylene group, or a substituted or unsubstituted p-phenylene group, but is not limited thereto.

For example, $R^d$ may independently be hydrogen, deuterium, a cyano group, a substituted or unsubstituted C1 to C20 alkyl group, a substituted or unsubstituted C6 to C20 aryl group, a substituted or unsubstituted C2 to C20 heterocyclic group, or a combination thereof, for example, $R^d$ may independently be hydrogen, deuterium, a cyano group, a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrene group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

For example, $R^d$ may independently be hydrogen, deuterium, a cyano group, a substituted or unsubstituted phenyl group, a substituted or unsubstituted m-biphenyl group, a substituted or unsubstituted p-biphenyl group, a substituted or unsubstituted triphenylene group, a substituted or unsubstituted fluorenyl group, a substituted or unsubstituted dibenzofuranyl group, or a substituted or unsubstituted dibenzothiophenyl group, but is not limited thereto.

$R^d$ is independently present or adjacent groups thereof are linked with each other to form a substituted or unsubstituted monocyclic or polycyclic ring, or a substituted or unsubstituted aromatic monocyclic or polycyclic heteroring.

For example, in the group represented by Chemical Formula B, at least two of $Z^1$ to $Z^5$ may be N and $R^d$ may independently be present.

For example, the group represented by Chemical Formula B may be a substituted or unsubstituted pyrimidinyl group or a substituted or unsubstituted triazinyl group.

For example, $Z^1$ and $Z^3$ may be N and $Z^2$, $Z^4$, and $Z^5$ may independently be C-$L^b$-$R^d$; $Z^3$ and $Z^5$ may be N and $Z^1$, $Z^2$, and $Z^4$ may independently be C-$L^b$-$R^d$; or $Z^2$ and $Z^4$ may be N and $Z^1$, $Z^3$, and $Z^5$ may independently be C-$L^b$-$R^d$. In this case, $L^b$ and $R^d$ are the same as described above.

For example, $Z^1$, $Z^3$, and $Z^5$ may be N and $Z^2$ and $Z^4$ may independently be C-$L^b$-$R^d$. In this case, $L^b$ and $R^d$ are the same as described above.

For example, in the group represented by Chemical Formula B, at least one of $Z^1$ to $Z^5$ may be N and $R^d$ is linked with each other to form a substituted or unsubstituted aromatic monocyclic ring or a substituted or unsubstituted aromatic monocyclic heteroring.

In this case, the group represented by Chemical Formula B may be a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted naphthyridinyl group.

For example, $Z^3$ and $Z^4$ may independently be C—$R^d$, adjacent $R^d$'s are linked with each other to form a benzene ring, and one of $Z^1$, $Z^2$, and $Z^5$ may be N.

For example, $Z^3$ and $Z^4$ may independently be C—$R^d$, adjacent $R^d$'s are linked with each other to form a benzene ring, and two of $Z^1$, $Z^2$, and $Z^5$ may be N.

For example, $Z^3$ and $Z^4$ may independently be C—$R^d$, adjacent $R^d$'s are linked with each other to form a benzene ring, and each of $Z^1$, $Z^2$, and $Z^5$ may be N.

For example, Chemical Formula B may be represented by one of Chemical Formulae B-1 to B-7, but is not limited thereto.

[Chemical Formula B-1]

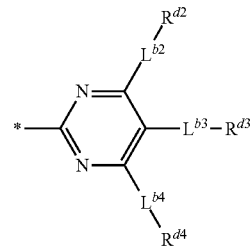

[Chemical Formula B-2]

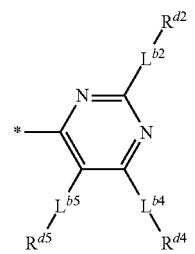

-continued

[Chemical Formula B-3]
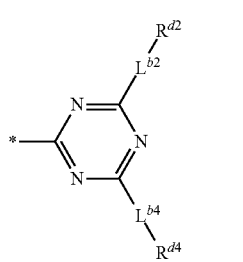

[Chemical Formula B-4]
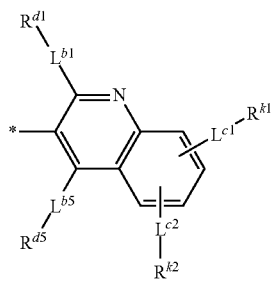

[Chemical Formula B-5]
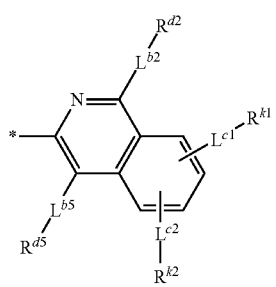

[Chemical Formula B-6]
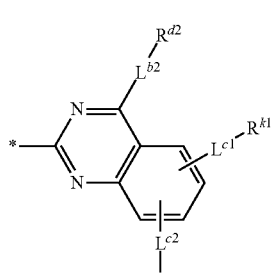

[Chemical Formula B-7]
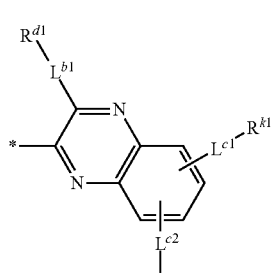

In Chemical Formula B-1 to Chemical Formula B-7, $L^{b1}$ to $L^{b5}$ and $L^{c1}$ and $L^{c2}$ are the same as $L^b$, and $R^{d1}$ to $R^{d5}$, $R^{k1}$, and $R^{k2}$ are the same as $R^d$.

For a specific example, the group represented by Chemical Formula B may be a substituted or unsubstituted pyrimidinyl group, a substituted or unsubstituted triazinyl group, a substituted or unsubstituted quinoxalinyl group, a substituted or unsubstituted quinazolinyl group, or a substituted or unsubstituted naphthyridinyl group.

For a more specific example, Chemical Formula B may be one of substituents of Group I.

[Group I]

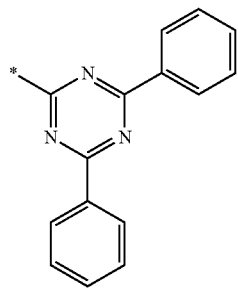

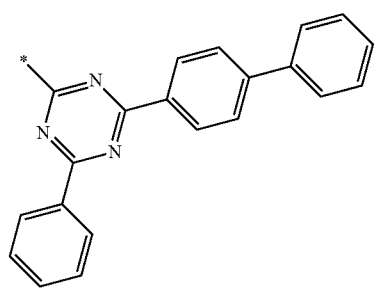

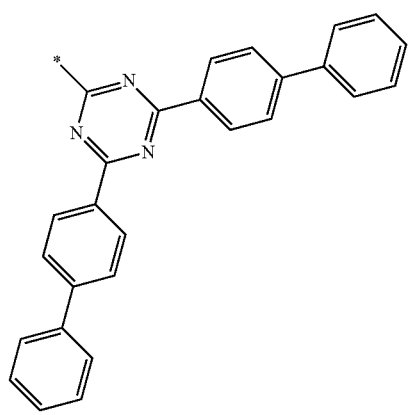

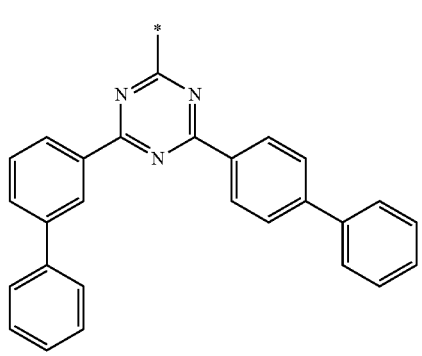

55
-continued
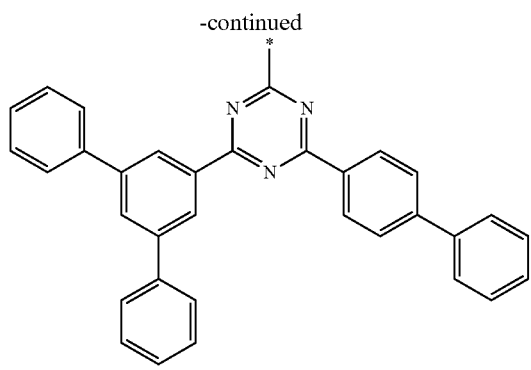
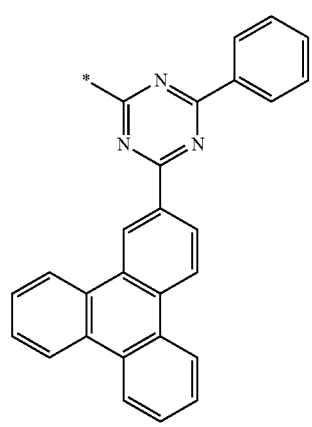
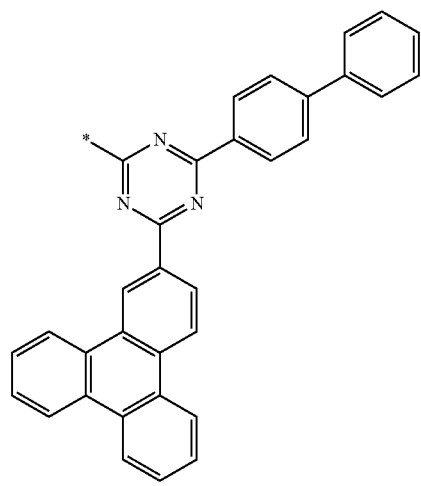
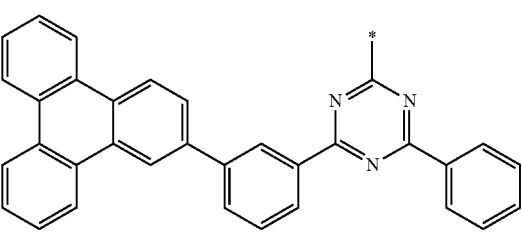
56
-continued
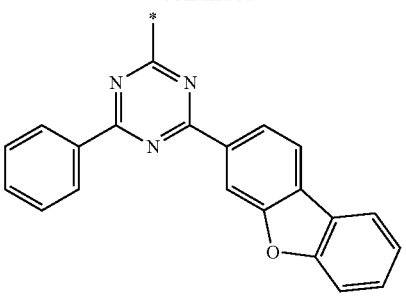
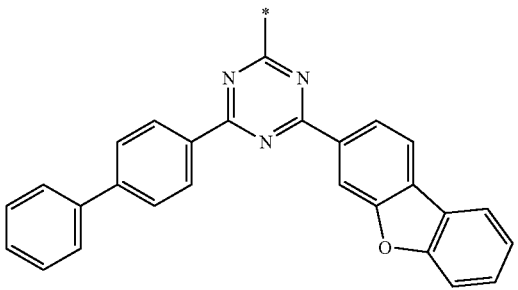
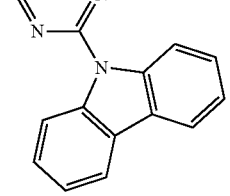
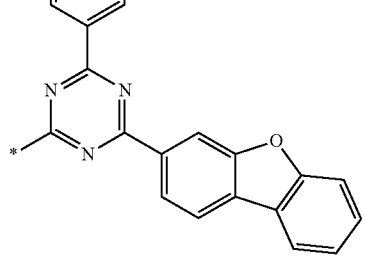
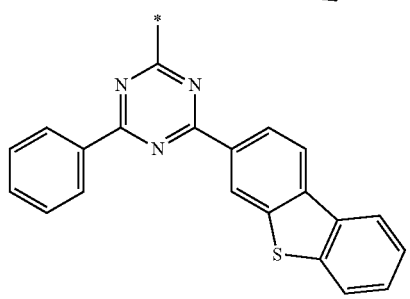

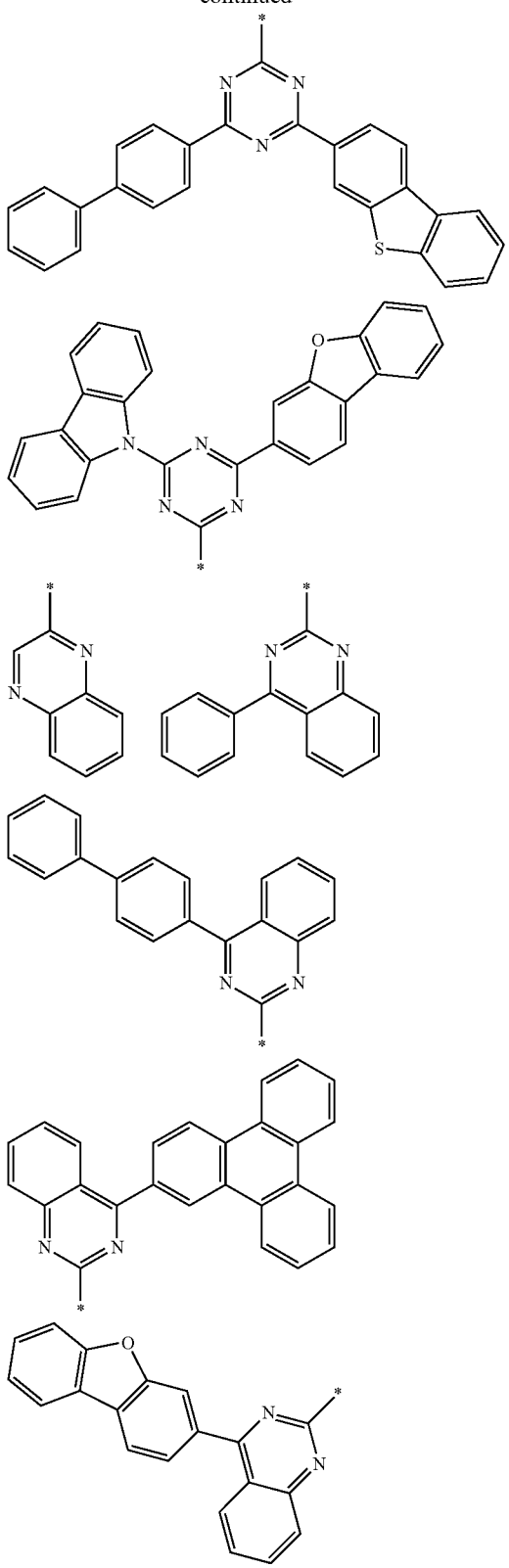

[Chemical Formula 2A-1]

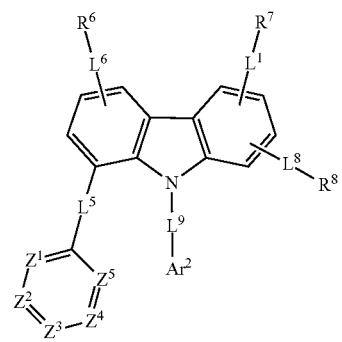

[Chemical Formula 2A-2]

[Chemical Formula 2A-3]

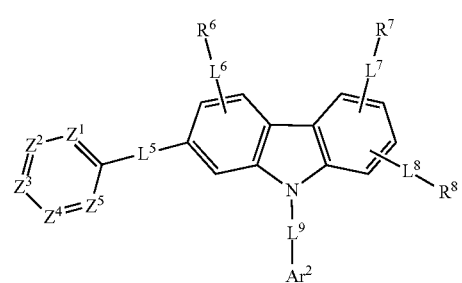

[Chemical Formula 2A-4]

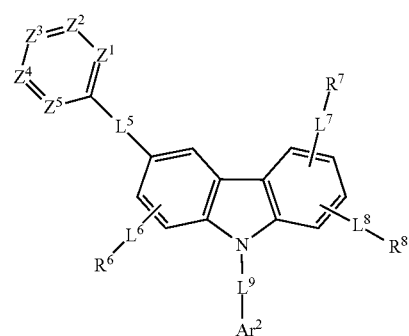

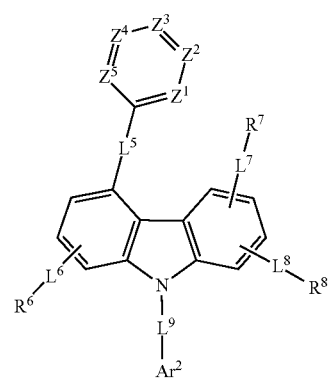

In Chemical Formula 2A-1 to Chemical Formula 2A-4, $L^5$ to $L^9$, $Ar^2$, $R^5$ to $R^8$, and $Z^1$ to $Z^5$ are the same as described above.

For example, Chemical Formula 2A may be represented by one of Chemical Formula 2A-1 to Chemical Formula 2A-4 according to a specific binding position of the group represented by Chemical Formula B.

For example, Chemical Formula 2C may be represented by one of Chemical Formula 2C-1 to Chemical Formula 2C-4 according to a specific binding position of the group represented by Chemical Formula B.

[Chemical Formula 2C-1]

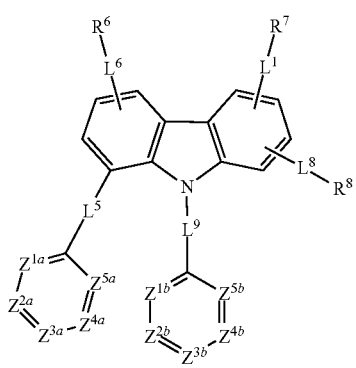

[Chemical Formula 2C-2]

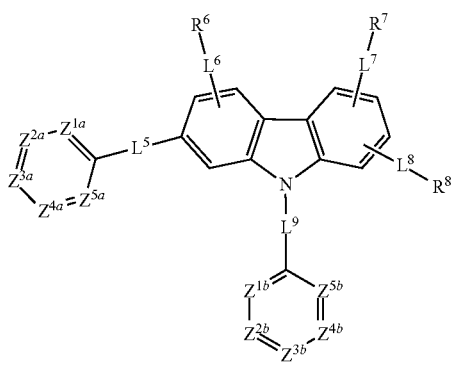

[Chemical Formula 2C-3]

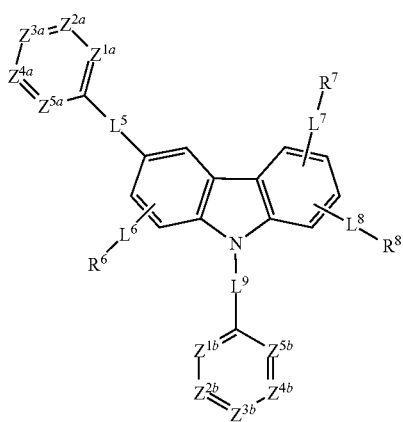

[Chemical Formula 2C-4]

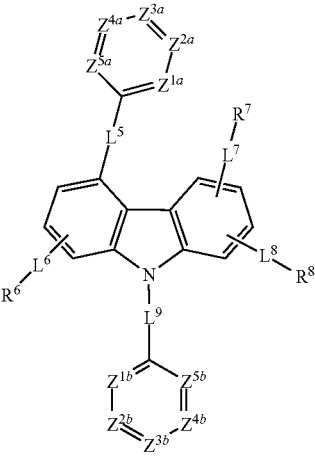

In Chemical Formula 2C-1 to Chemical Formula 2C-4, $L^5$ to $L^9$, $R^6$ to $R^8$, $Z^1a$ to $Z^{5a}$ and $Z^{1b}$ to $Z^{5b}$ are the same as described above.

In a specific embodiment of the present invention, the second compound may be represented by one of Chemical Formula 2B, Chemical Formula 2C, Chemical Formula 2D, Chemical Formula 2E, and Chemical Formula 2F, for example Chemical Formula 2B or Chemical Formula 2F.

The second compound may be for example one of compounds of Group 2, but is not limited thereto.

[Group 2]

B-1

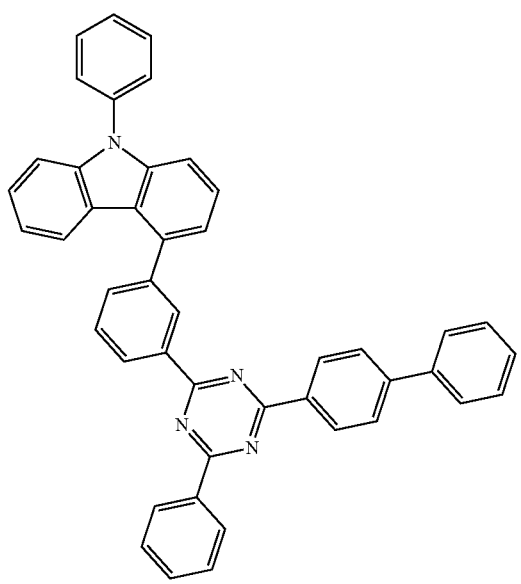

B-2
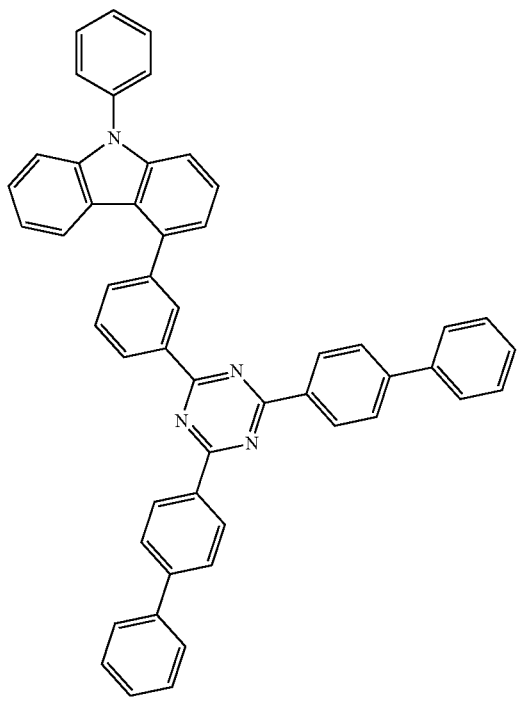
B-4
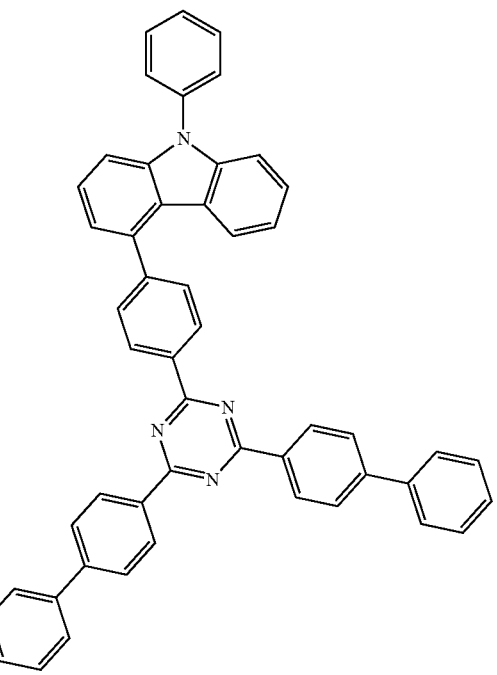
B-3
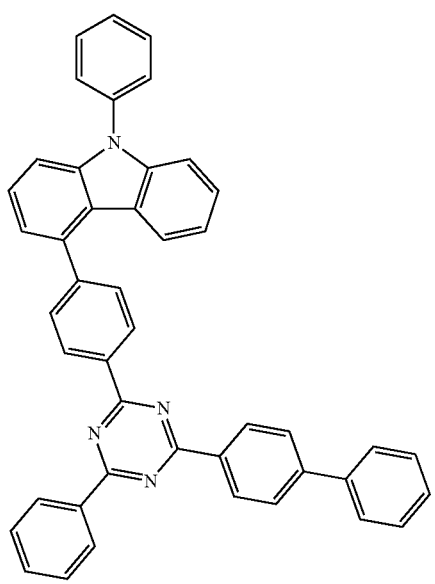
B-5
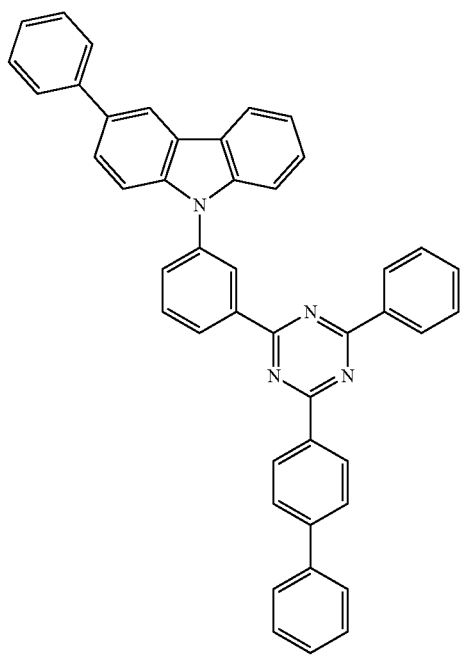

B-6
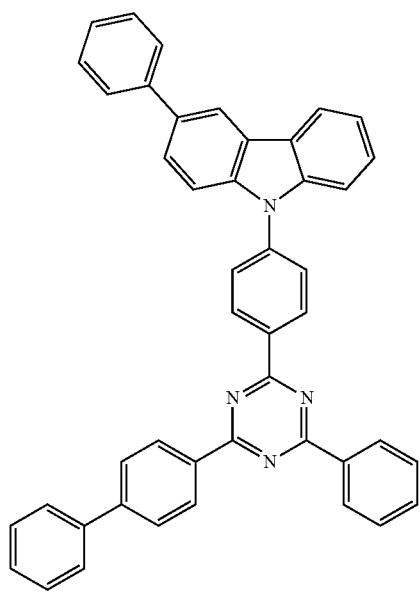
B-7
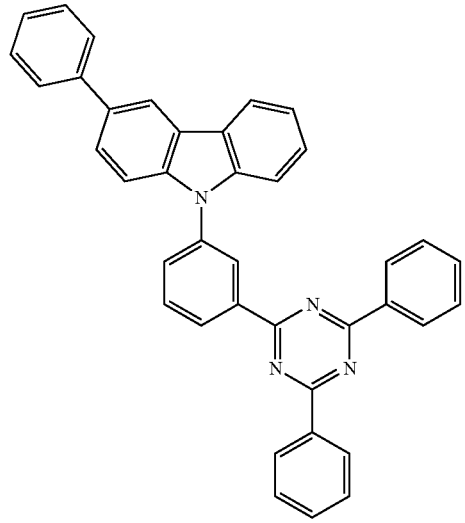
B-8
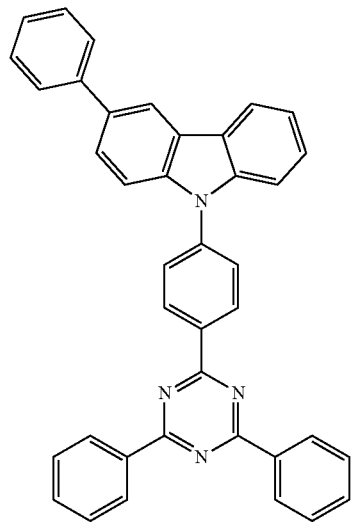
B-9
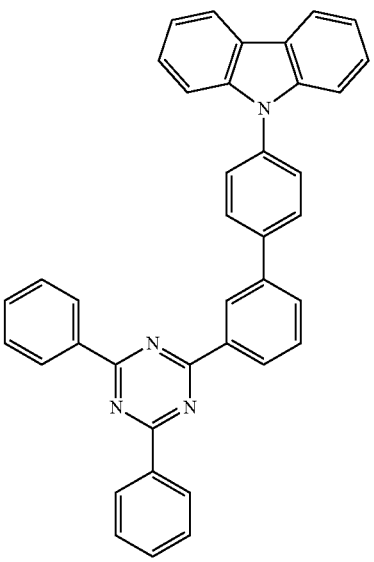
B-10
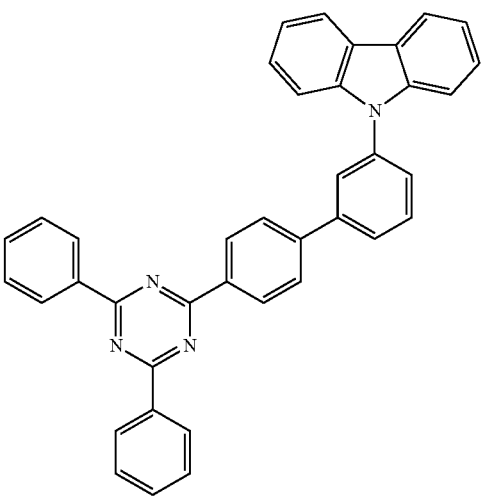

B-11
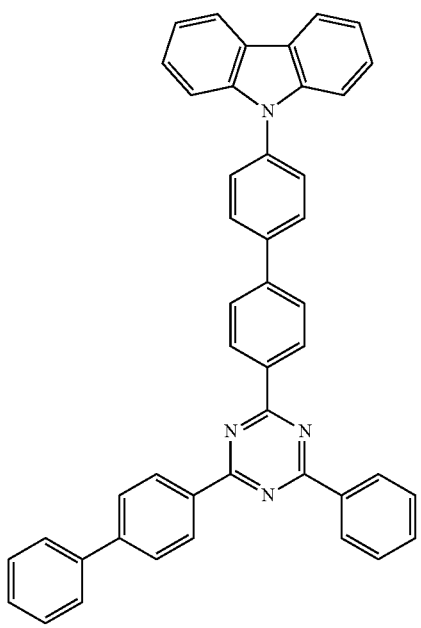
B-12
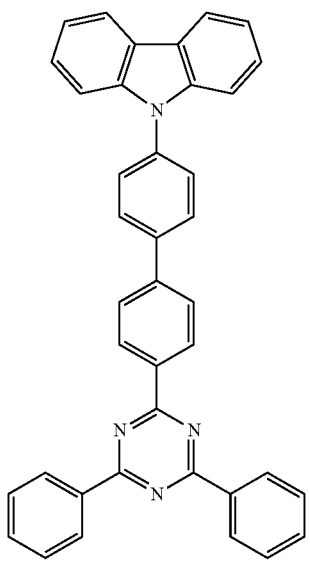
B-13
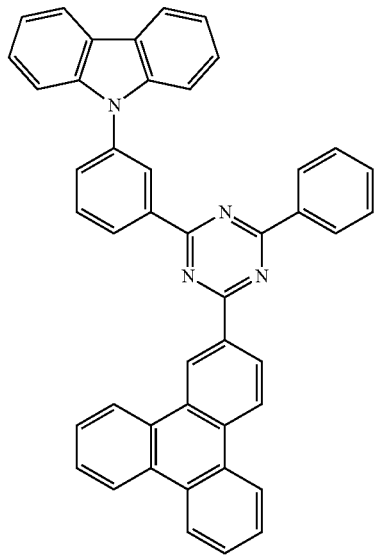
B-14
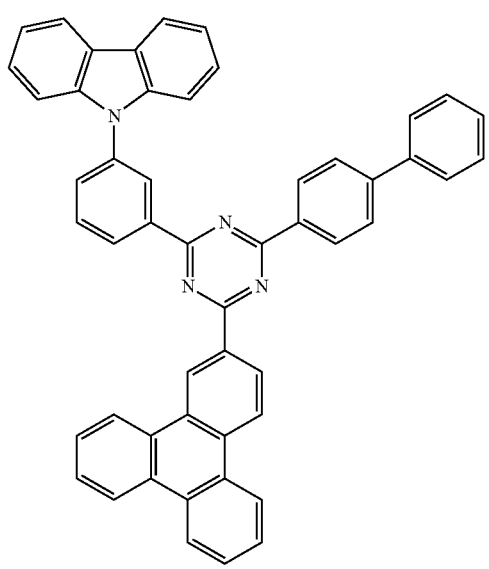
B-15

B-16
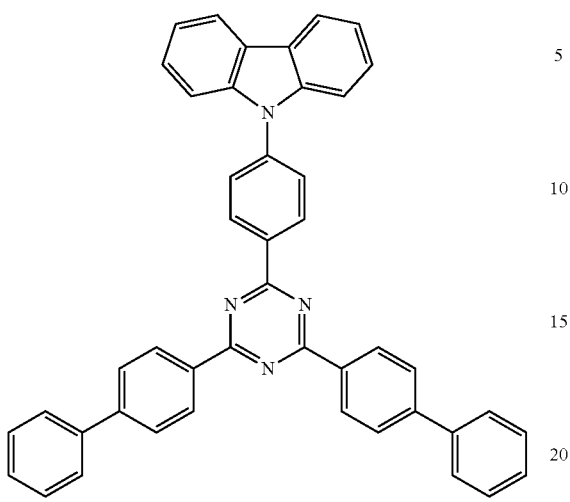
B-17
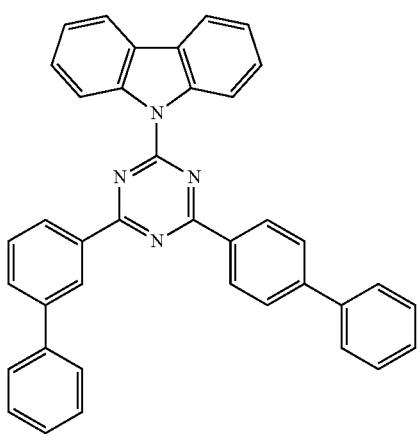
B-18
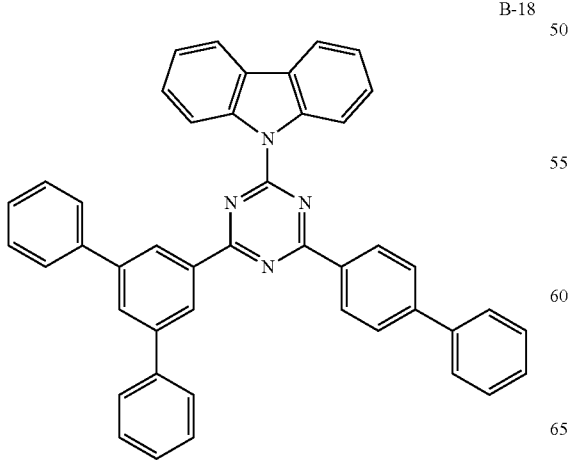
B-19
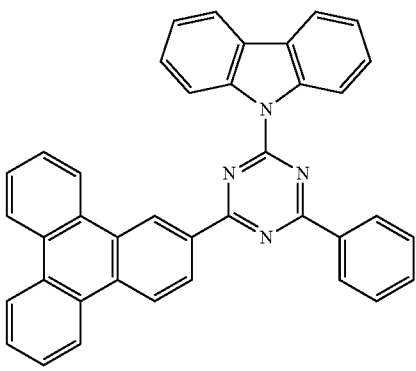
B-20
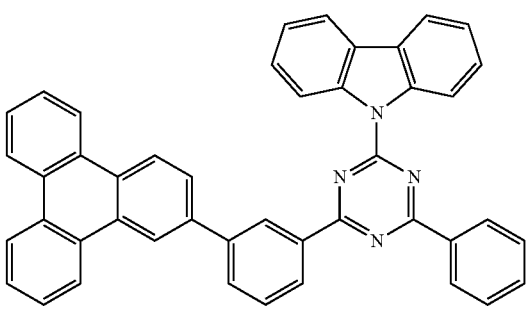
B-21
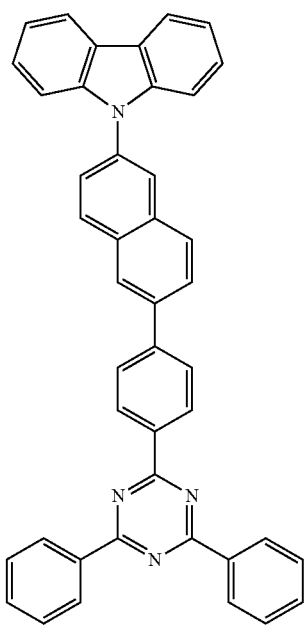

B-22
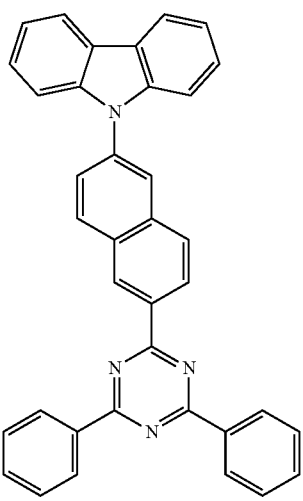
B-23
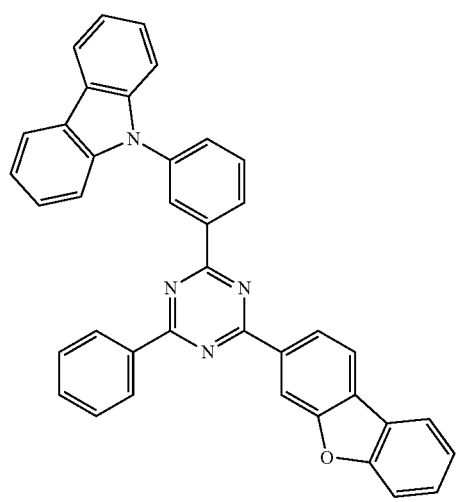
B-24
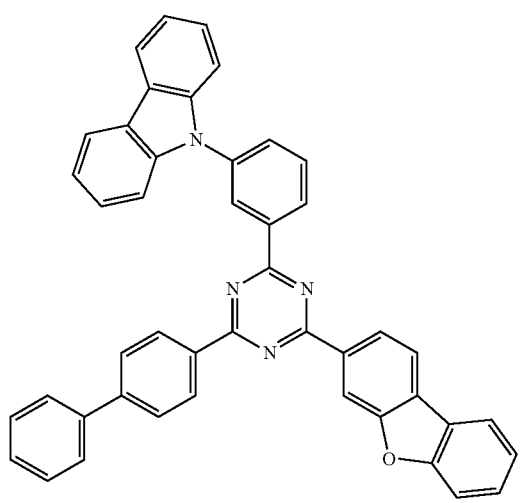
B-25
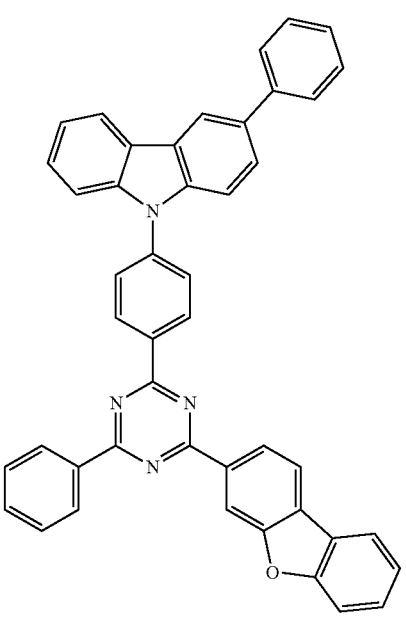
B-26
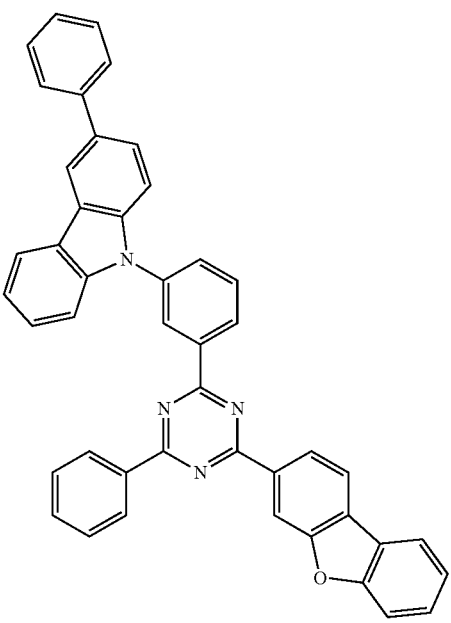

B-27
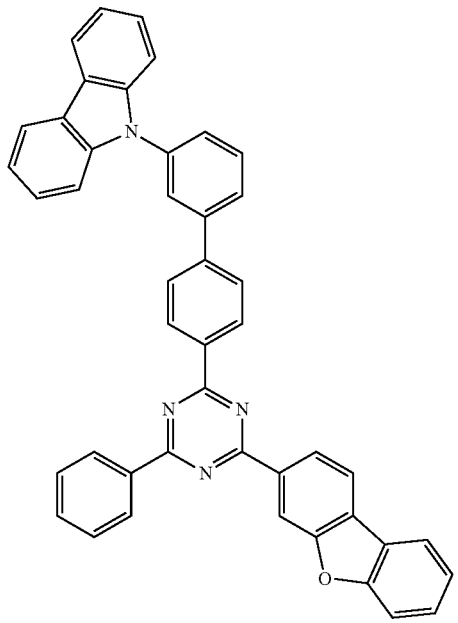
B-28
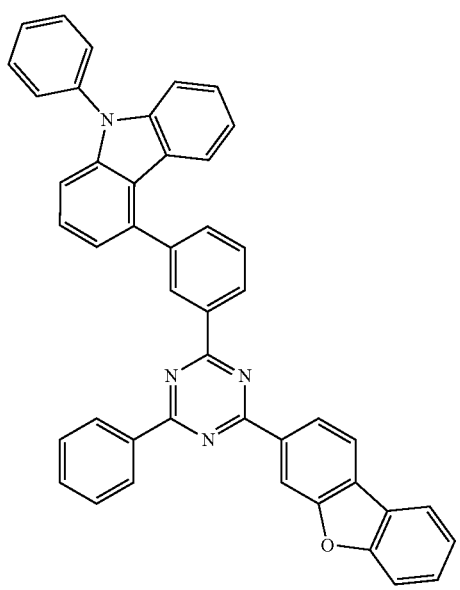
B-29
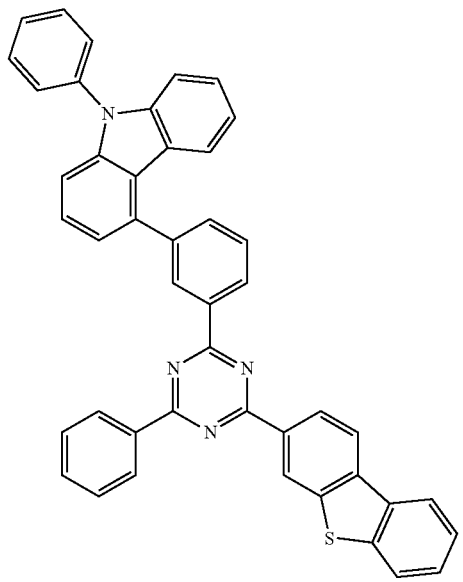
B-30
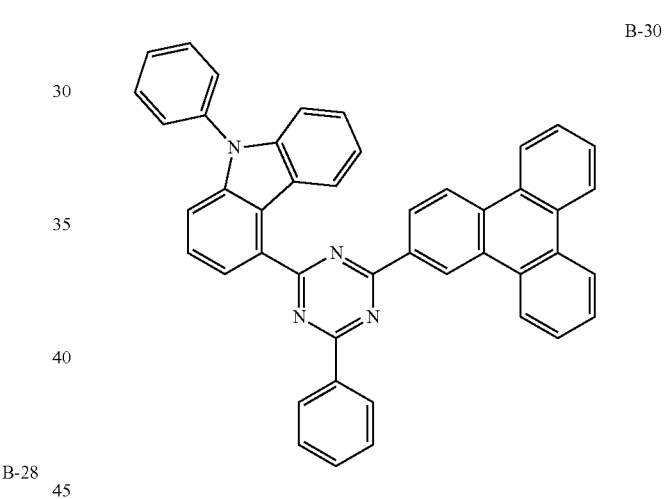
B-31
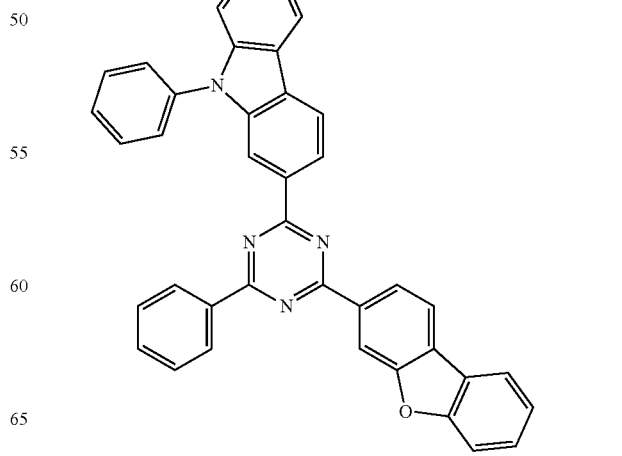

B-32
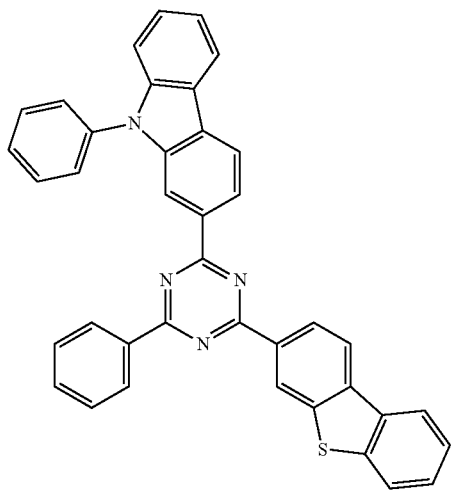
B-35
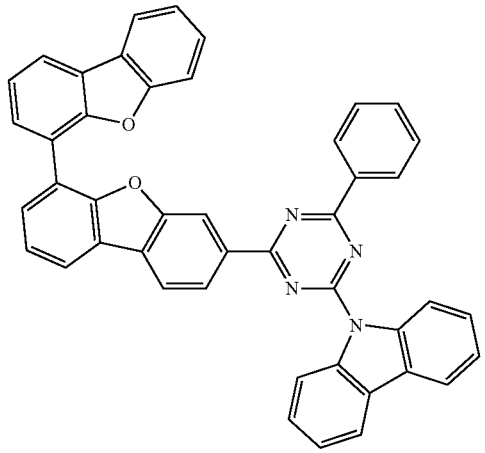
B-33
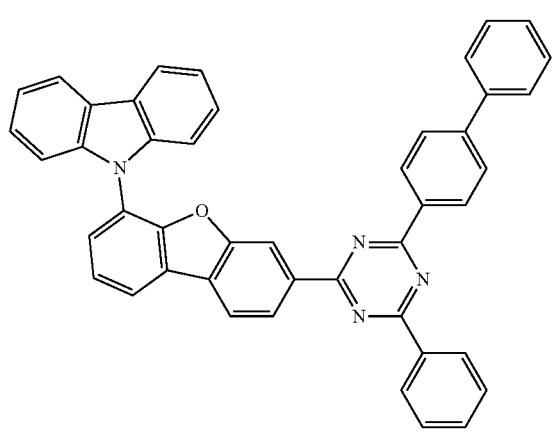
B-36
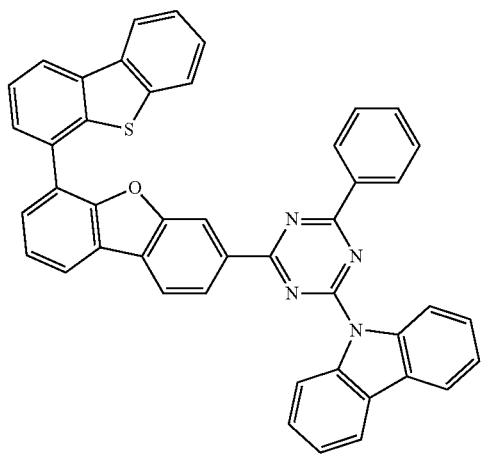
B-34
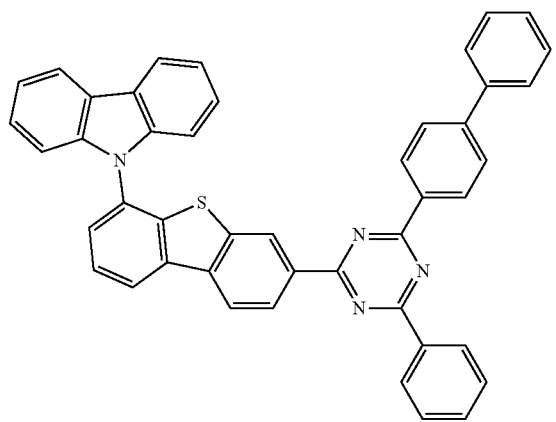
B-37
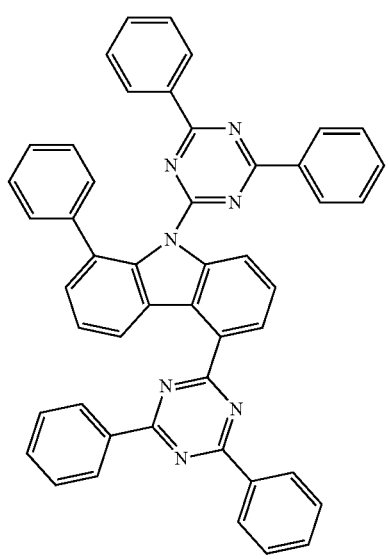

B-38
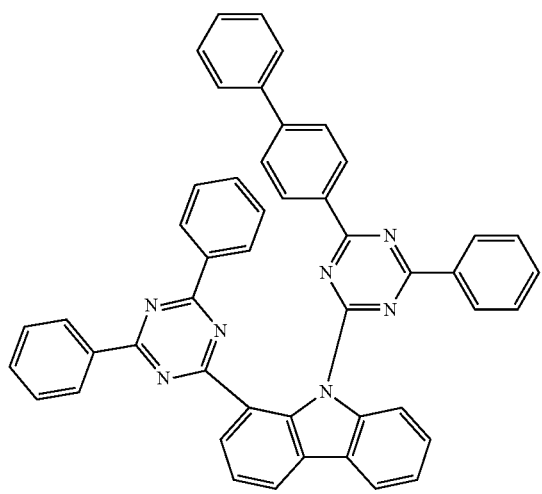
B-39
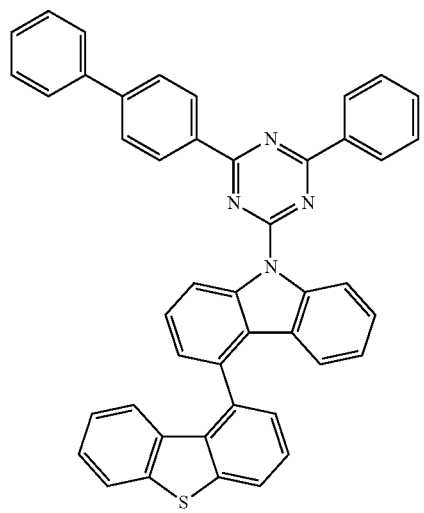
B-40
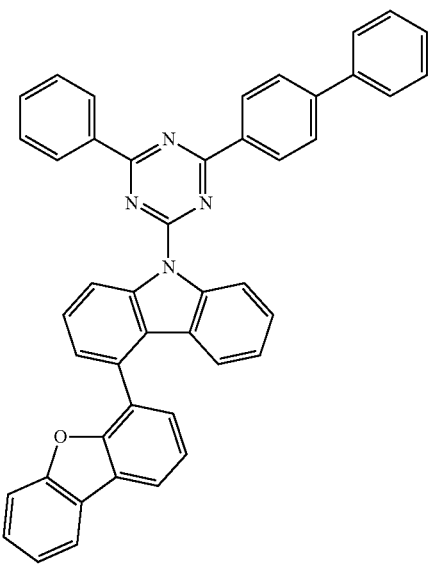
B-41
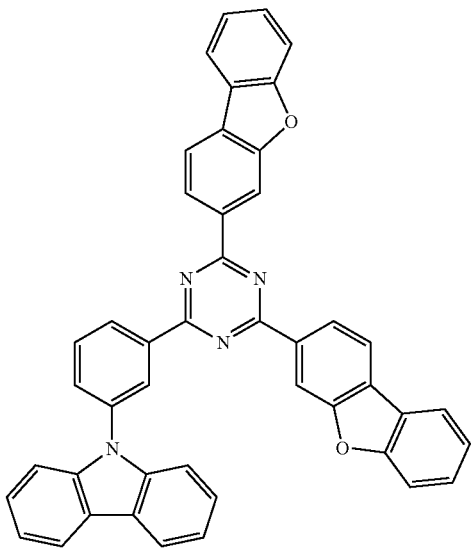
B-42
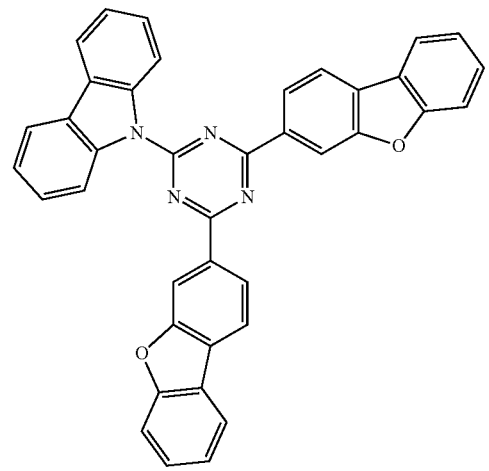
B-43
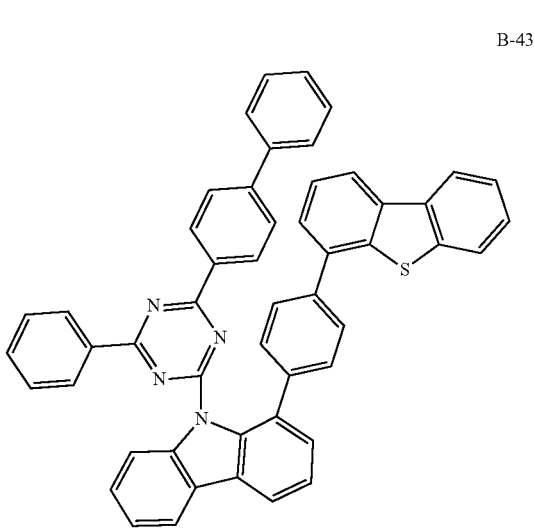

B-44
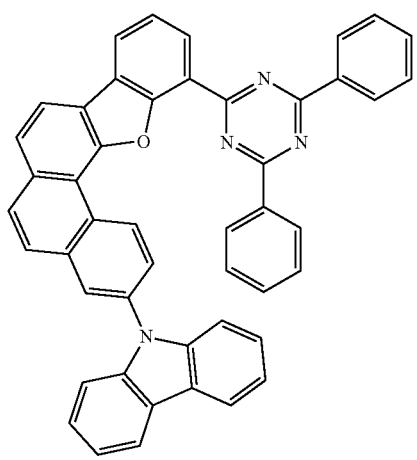
B-45
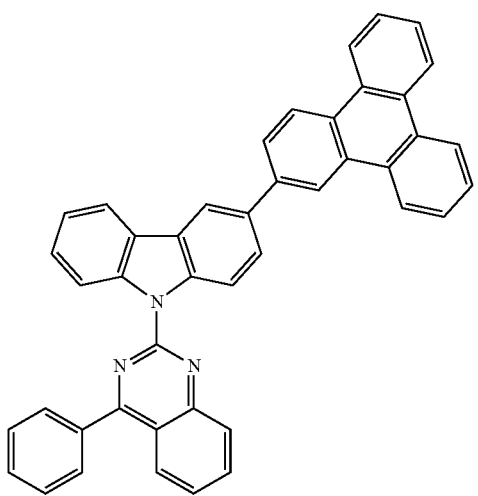
B-46
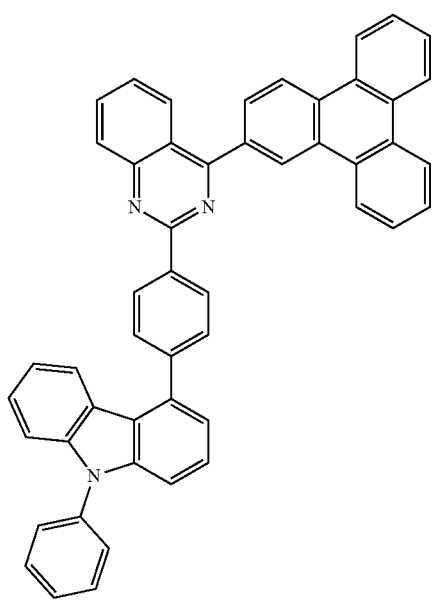
B-47
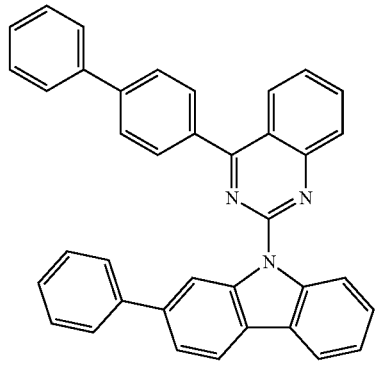
B-48
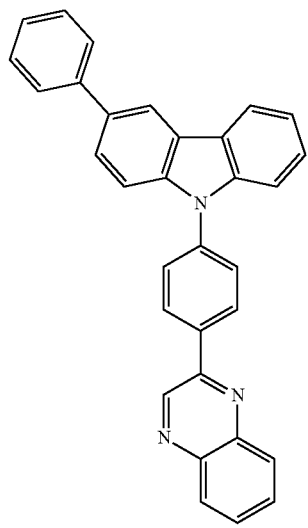
B-49
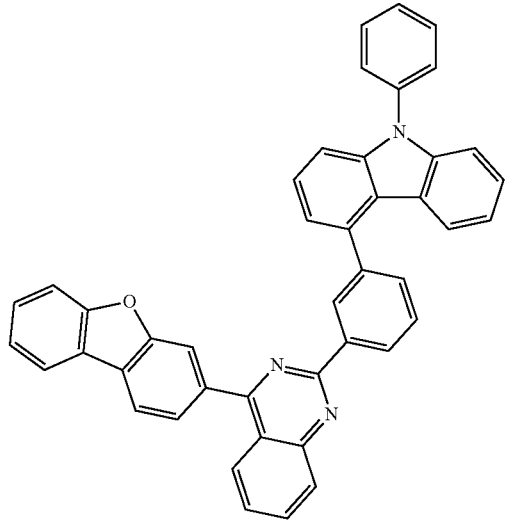

B-50
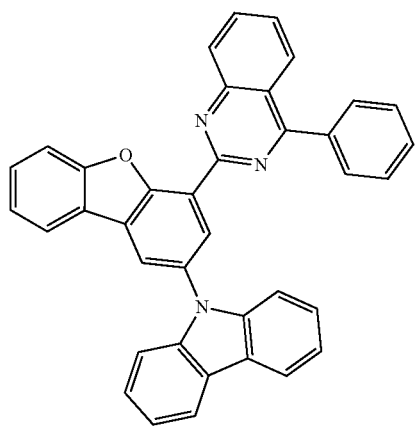
B-51
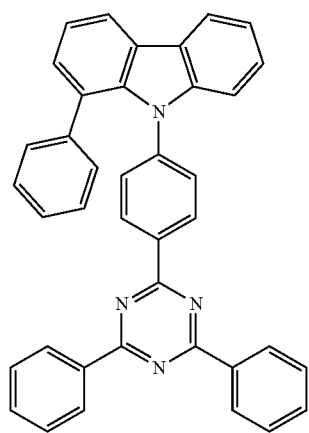
B-52
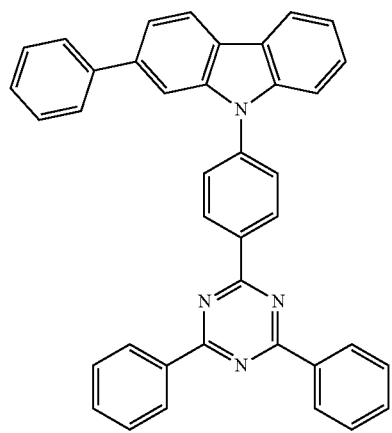
B-53
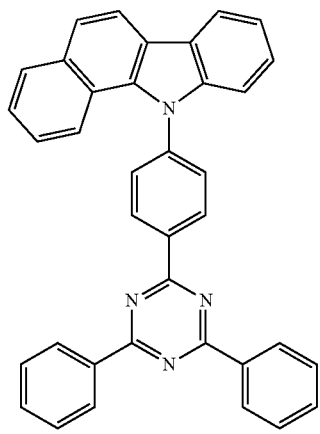
B-54
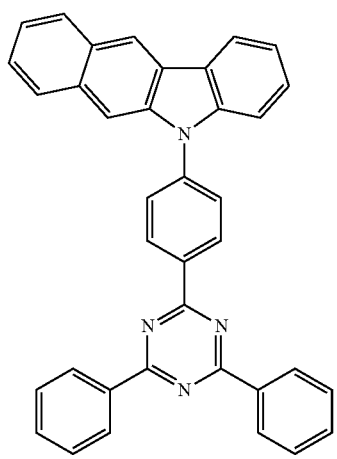
B-55
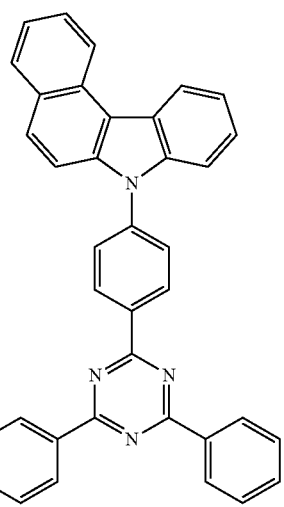

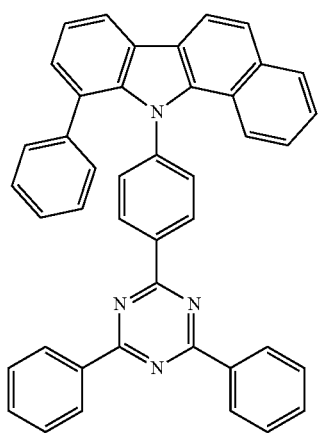
B-56
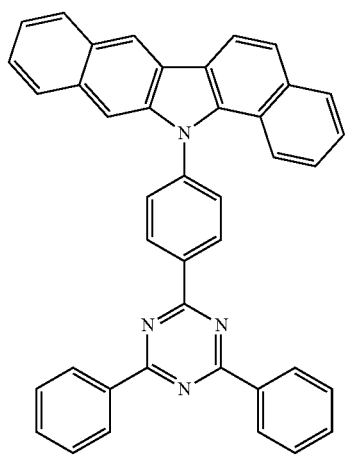
B-59
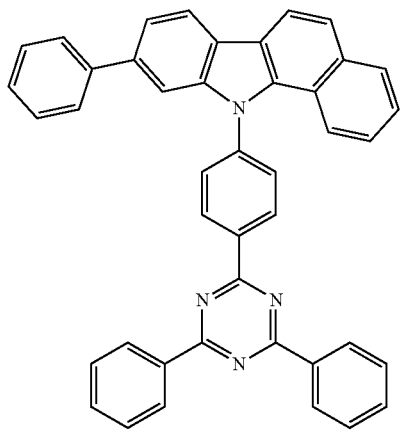
B-57
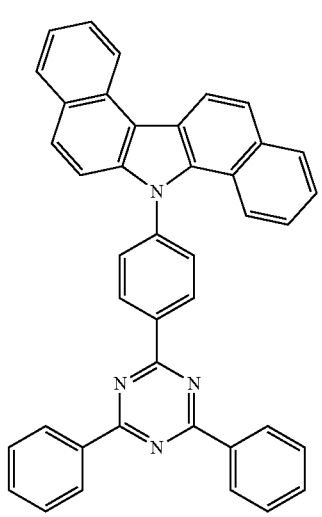
B-60
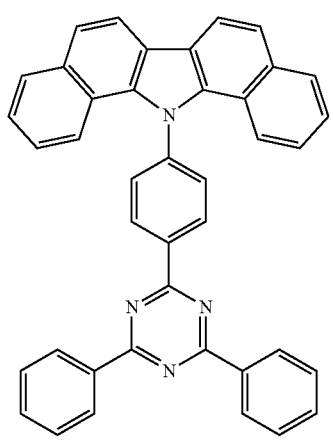
B-58
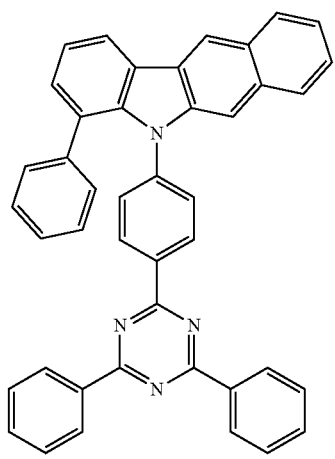
B-61

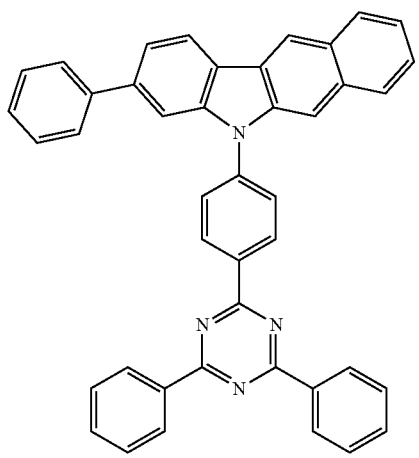
B-62
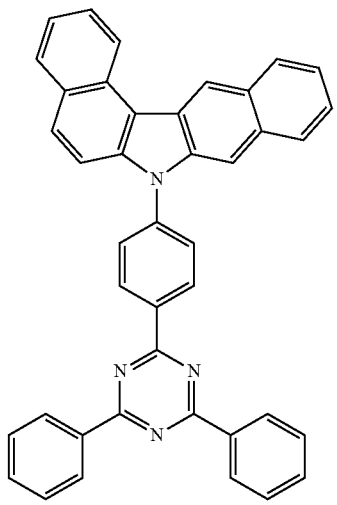
B-65
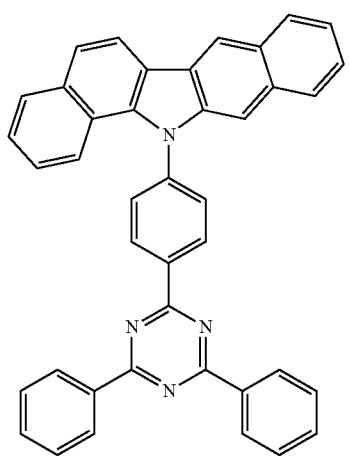
B-63
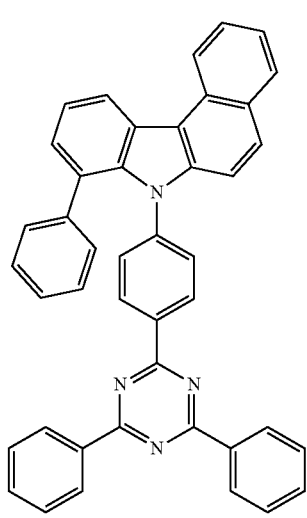
B-66
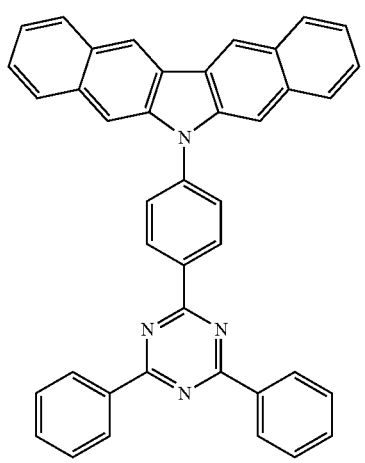
B-64
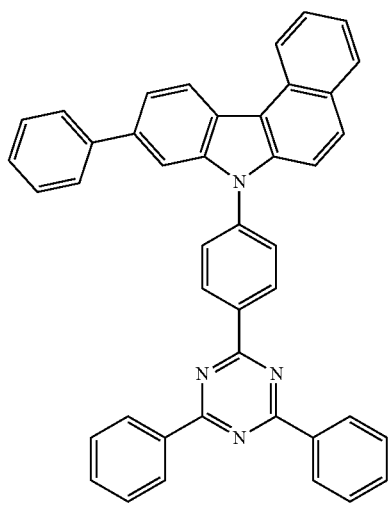
B-67

B-68
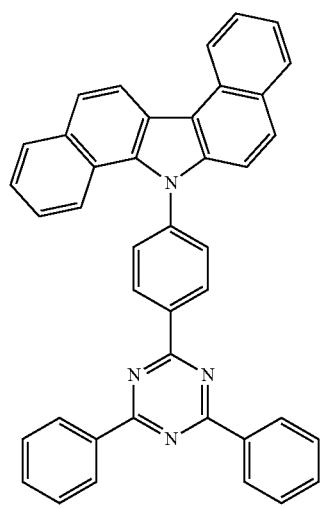
B-71
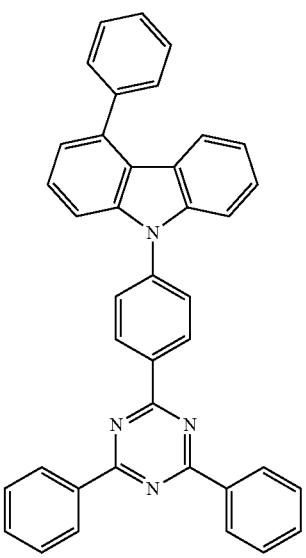
B-69
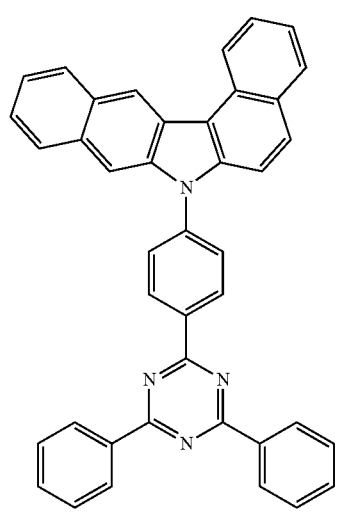
B-72
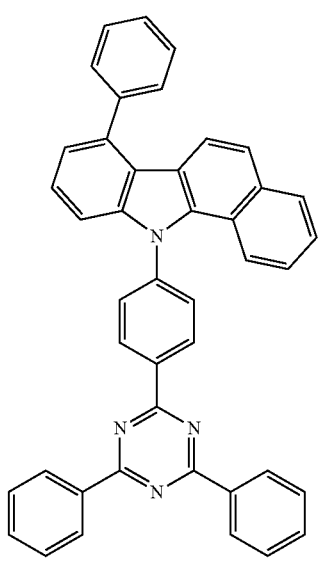
B-70
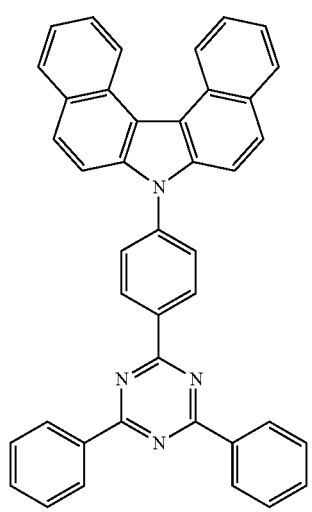
B-73
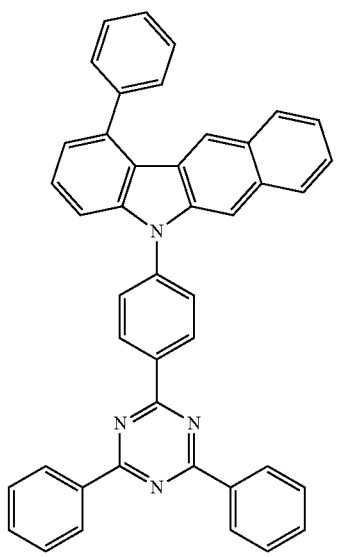

B-74
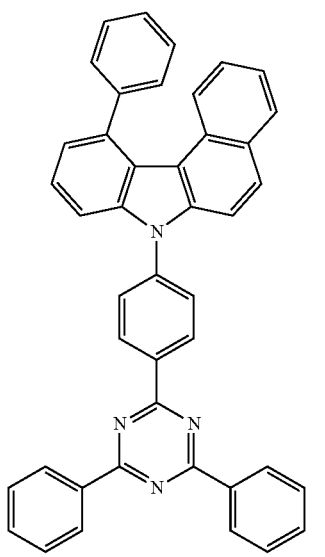

B-75
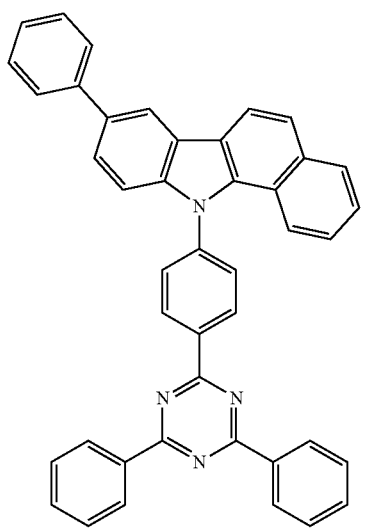

B-76
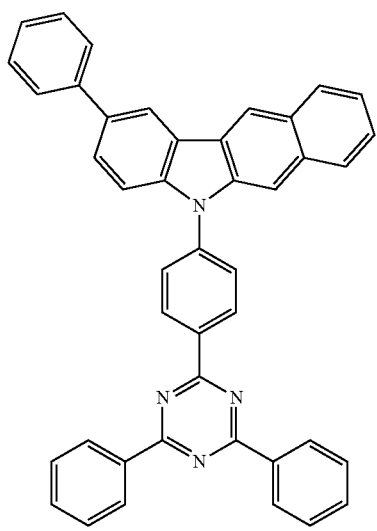

B-77
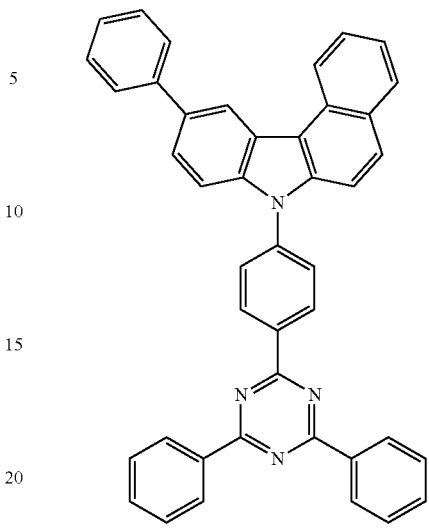

B-78
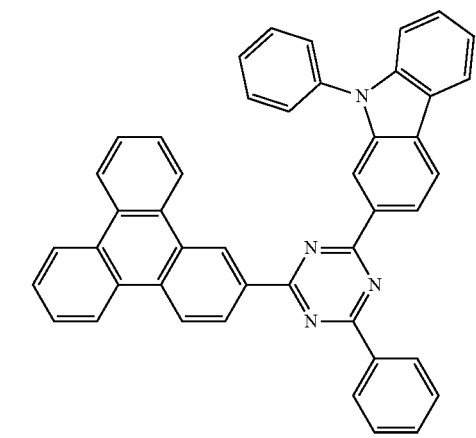

The first compound and the second compound may be for example included in a weight ratio of 1:99 to 99:1. Within the range, a desirable weight ratio may be adjusted using a hole transport capability of the first compound and an electron transport capability of the second compound to realize bipolar characteristics and thus to improve efficiency and life-span. Within the range, they may be for example included in a weight ratio of about 10:90 to 90:10, about 20:80 to 80:20, about 30:70 to 70:30, about 40:60 to 60:40, or about 50:50. For example, they may be included in a weight ratio of about 50:50 to 60:40, for example, about 50:50 or about 60:40.

For example, a composition according to an example embodiment of the present invention may include a compound represented by Chemical Formula 1A-1-b as a first compound and a compound represented by Chemical Formula 2B or Chemical Formula 2F as a second compound.

For example, in Chemical Formula 1A-1-b, $Ar^1$ may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, $L^a$ and $L^1$ to $L^4$ may independently be a single bond, a substituted or unsubstituted phenylene group, a substituted or unsubstituted biphenylene group, a substituted or unsubstituted terphenylene group, or a substituted or unsubstituted naphthylene group, $R^a$, $R^1$, $R^2$, and $R^4$ may independently be hydrogen, deuterium, a cyano group, a substituted or unsubstituted C1 to C30 alkyl group, a substituted or unsubstituted C6 to C30 aryl group, a substituted or unsubstituted C2 to C30 heterocyclic group, or a combination thereof, and $R^b$ and $R^e$ are independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group, and in Chemical Formula 2B and Chemical Formula 2F, $L^5$ to $L^9$ may independently be a single bond, a substituted or unsubstituted phenylene group, a substituted or unsubstituted biphenylene group, a substituted or unsubstituted terphenylene group, or a substituted or unsubstituted naphthylene group, and $R^5$ to $R^8$, $R^e$, $R^f$, and $R^g$ may independently be hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof.

In addition, $Z^1$ to $Z^5$ may independently be N or $C-L^b-R^d$, at least two of $Z^1$ to $Z^5$ may be N, $L^b$ may independently be a single bond, or a substituted or unsubstituted C6 to C20 arylene group, and $R^d$ may independently be a substituted or unsubstituted phenyl group, a substituted or unsubstituted biphenyl group, a substituted or unsubstituted terphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

The composition may further include at least one compound in addition to the first compound and the second compound.

The composition may further include a dopant. The dopant may be for example a phosphorescent dopant, for example a red, green, or blue phosphorescent dopant, for example a red phosphorescent dopant.

The dopant is a material mixed in a small amount with the first compound and the second compound to cause light emission and generally a material such as a metal complex that emits light by multiple excitations into a triplet or more. The dopant may be, for example an inorganic, organic, or organic/inorganic compound, and one or more kinds thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L^{10}MX \qquad \text{[Chemical Formula Z]}$$

In Chemical Formula Z, M is a metal, and $L^{10}$ and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof, and the $L^{10}$ and X may be, for example a bidentate ligand.

The composition may be formed by a dry film formation method such as chemical vapor deposition (CVD).

Hereinafter, an organic optoelectronic device including the composition is described.

The organic optoelectronic device may be any device to convert electrical energy into photoenergy and vice versa without particular limitation, and may be for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views showing organic light emitting diodes according to embodiments.

Referring to FIG. 1, an organic optoelectronic device 100 according to an embodiment includes an anode 120 and a cathode 110 and facing each other and an organic layer 105 disposed between the anode 120 and the cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy) thiophene) (PEDOT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, $LiO_2$/Al, LiF/Ca, LiF/Al and $BaF_2$/Ca, but is not limited thereto.

The organic layer 105 includes a light emitting layer 130 including the composition.

The light emitting layer 130 may include for example the composition.

The composition may be for example a red light emitting composition.

The light emitting layer 130 may include for example the first compound and the second compound as a phosphorescent host.

Referring to FIG. 2, an organic light emitting diode 200 further includes a hole auxiliary layer 140 in addition to the light emitting layer 130. The hole auxiliary layer 140 may further increase hole injection and/or hole mobility while blocking electrons between the anode 120 and the light emitting layer 130. The hole auxiliary layer 140 may include for example at least one of a hole transport layer, a hole injection layer, and/or an electron blocking layer.

The hole auxiliary layer 140 may include for example at least one of compounds of Group D.

Specifically, the hole auxiliary layer 140 may include a hole transport layer between the anode 120 and the light emitting layer 130 and a hole transport auxiliary layer between the light emitting layer 130 and the hole transport layer, and at least one of compounds of Group D may be included in the hole transport auxiliary layer.
[Group D]
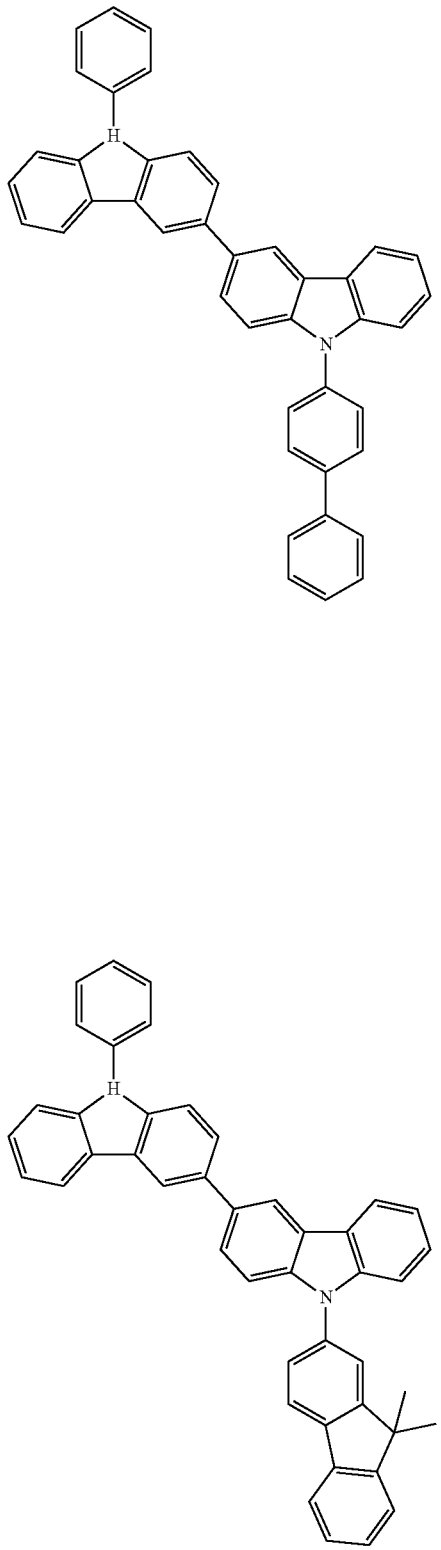
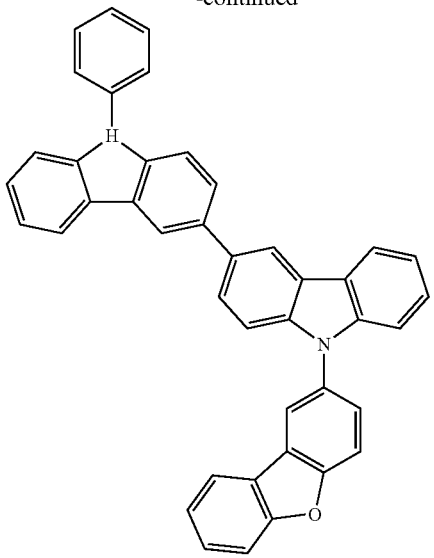
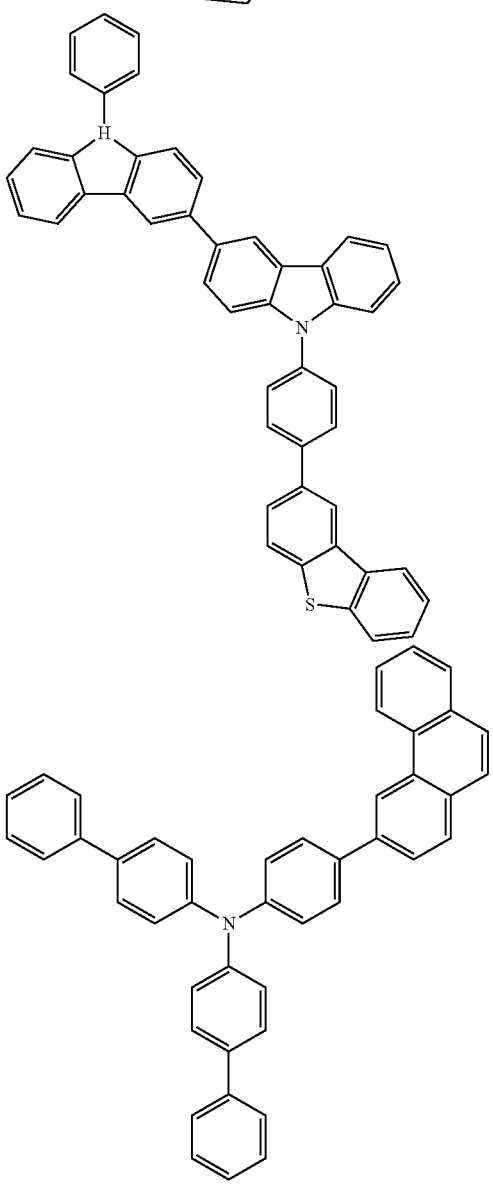

93
-continued
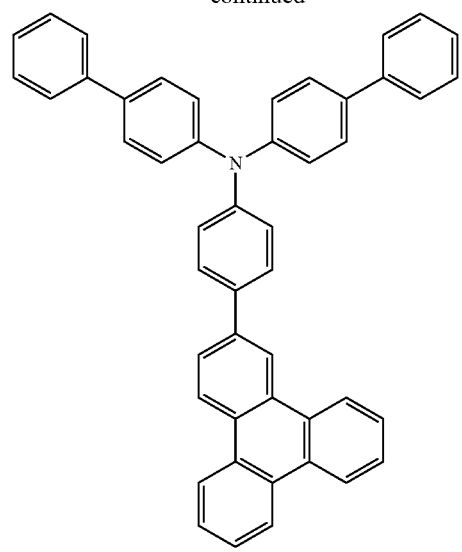
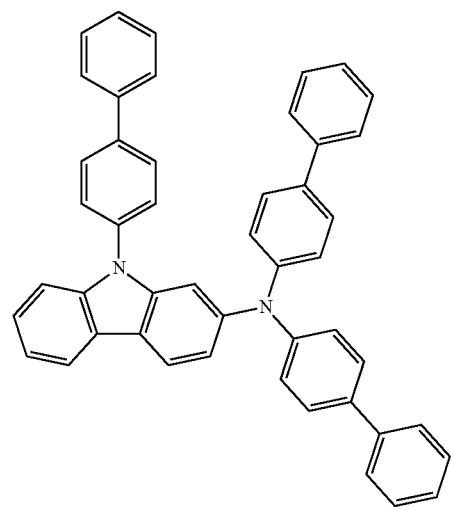
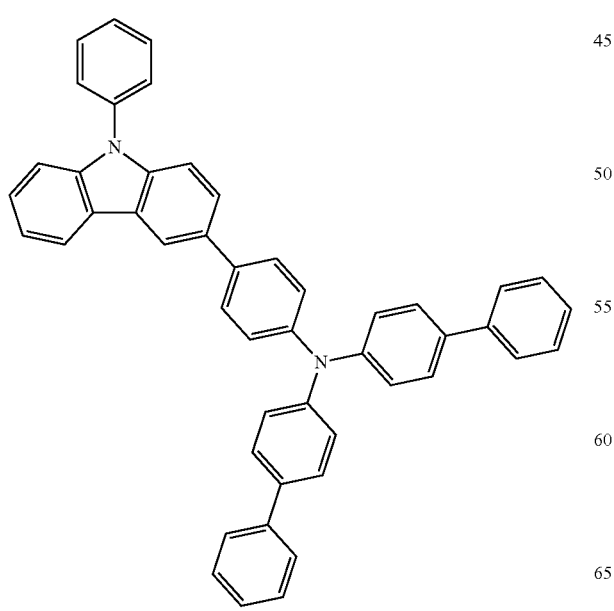
94
-continued
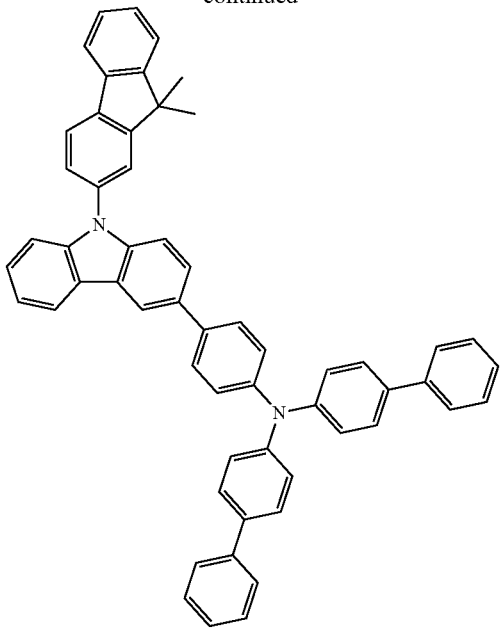
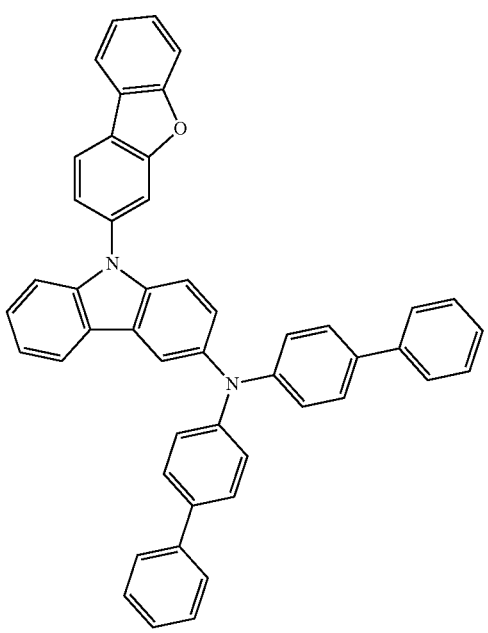

95
-continued
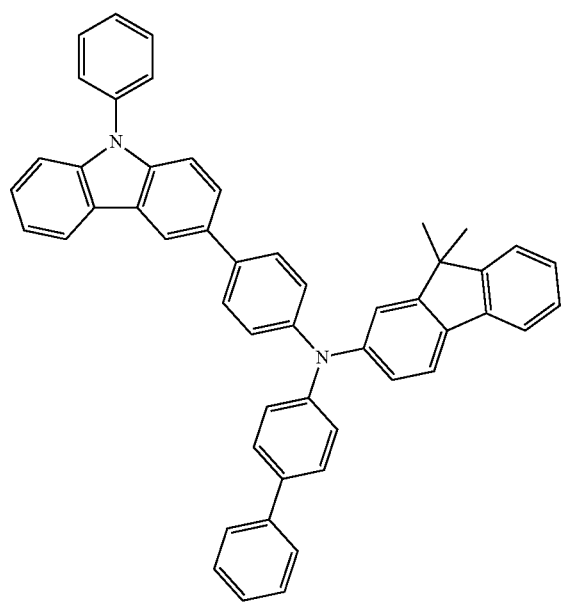
96
-continued
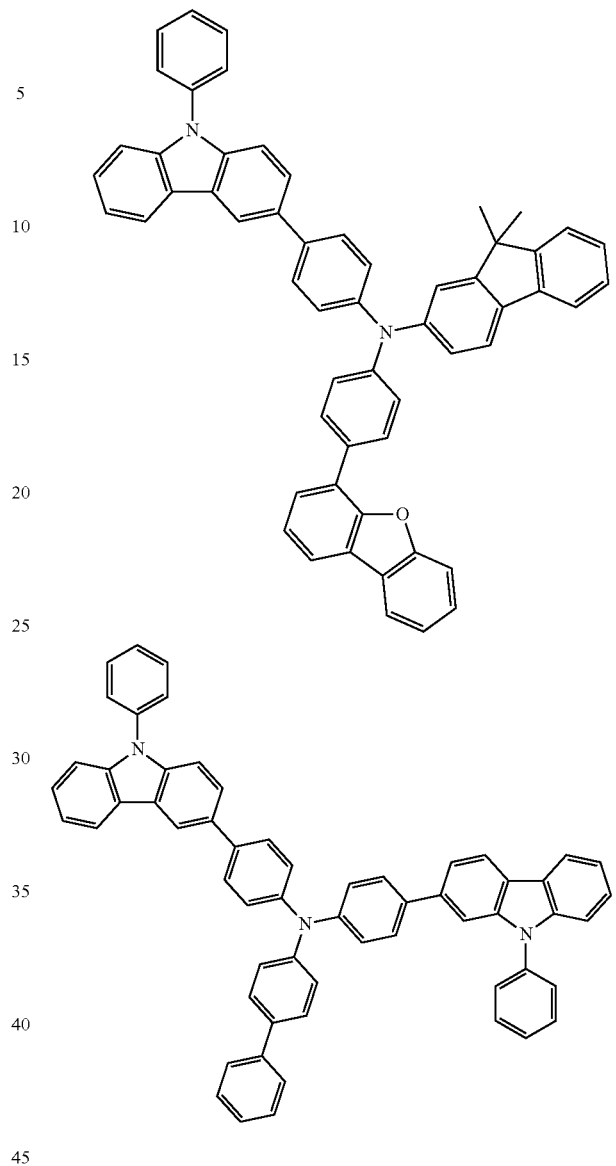
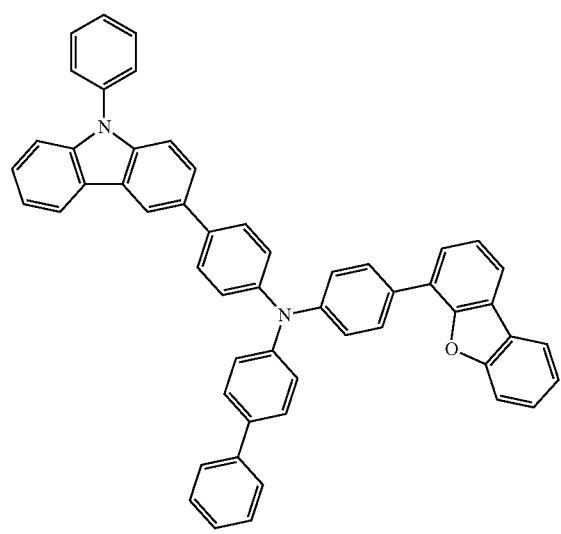
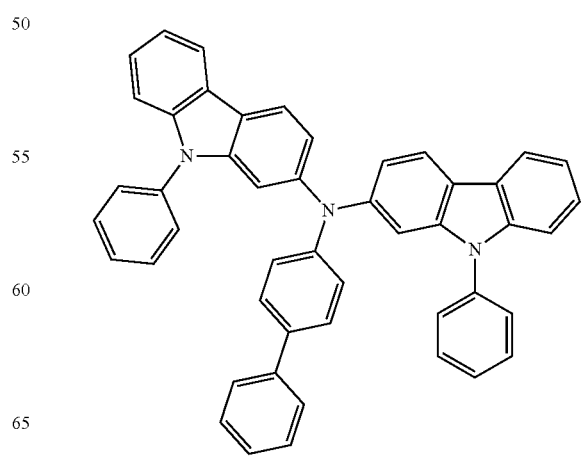

97
-continued
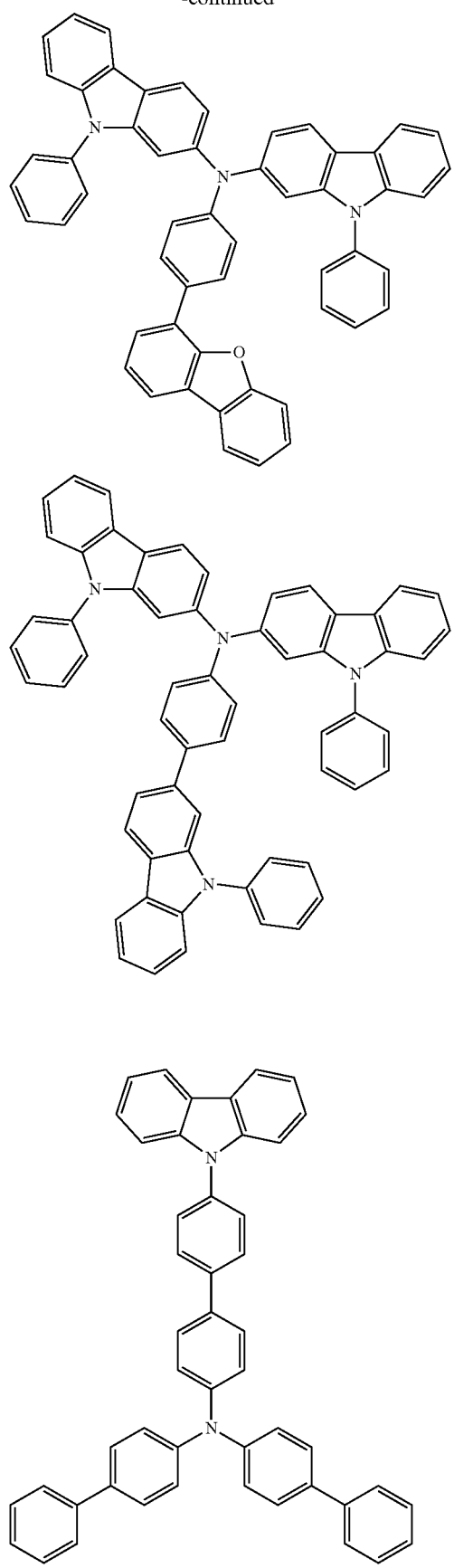
98
-continued
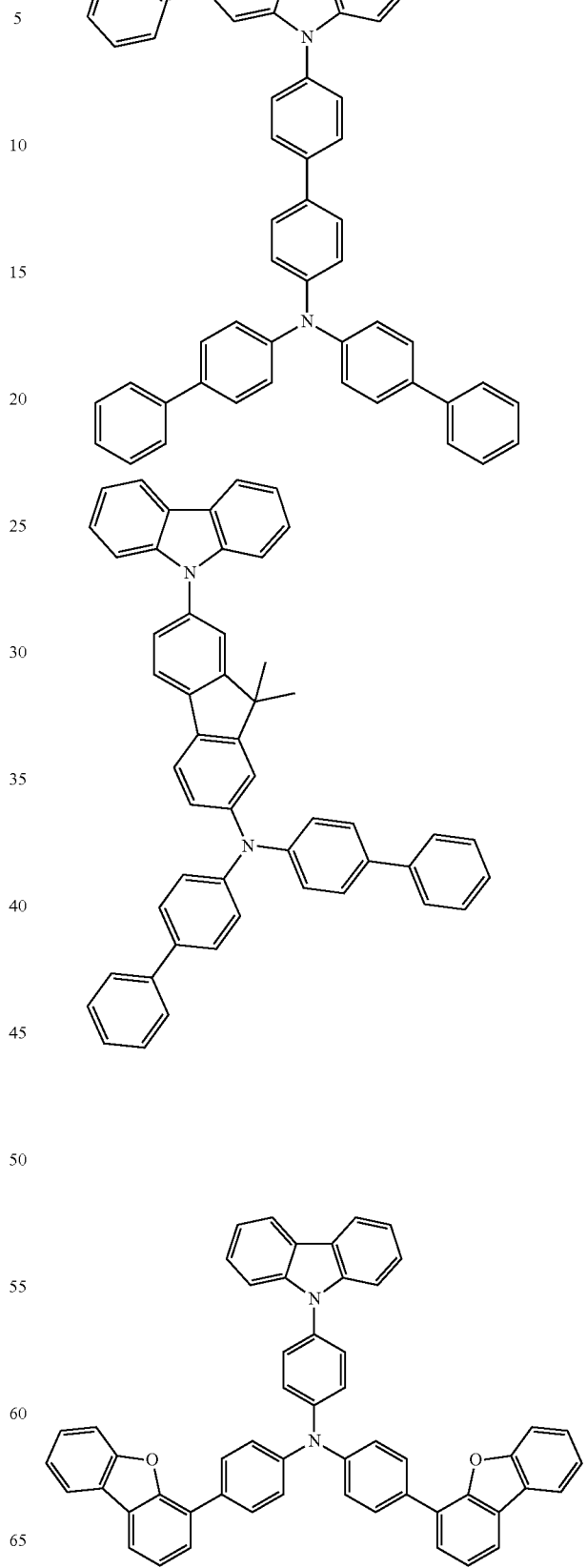

99
-continued
100
-continued
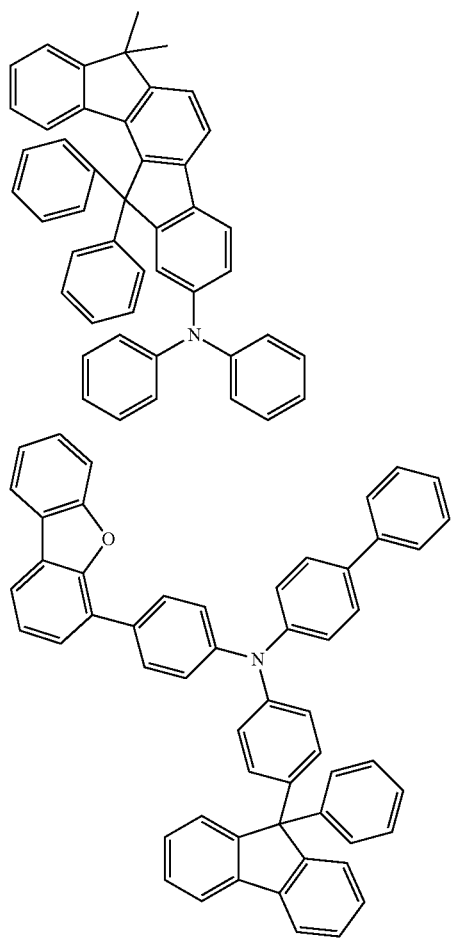
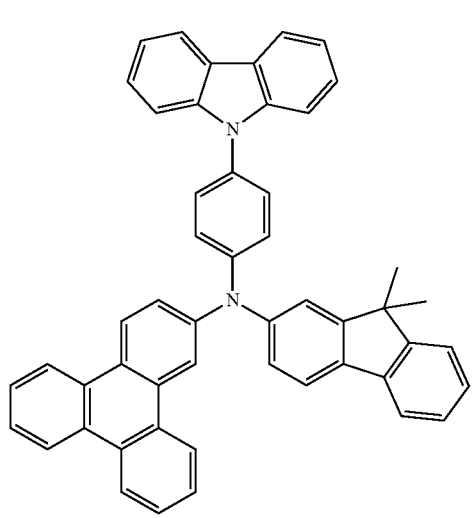
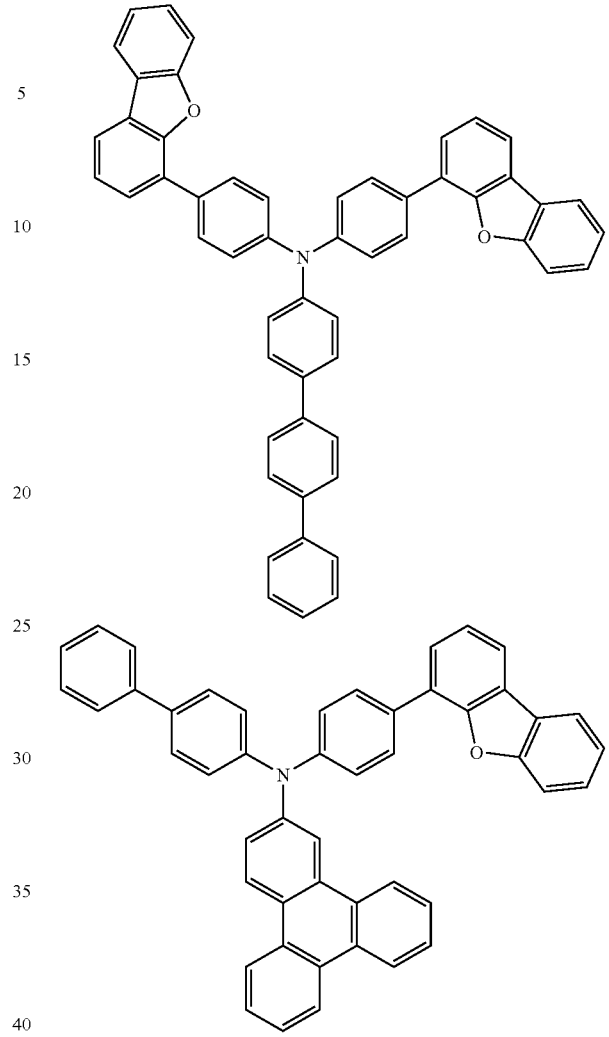

| 101 -continued | 102 -continued |
|---|---|
| 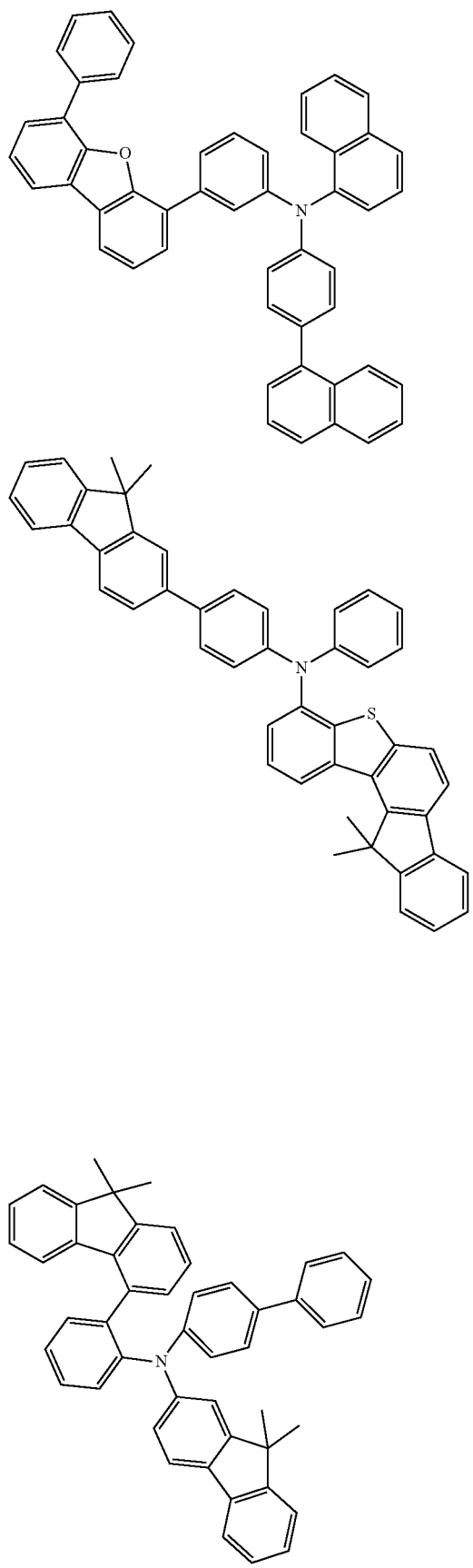 | 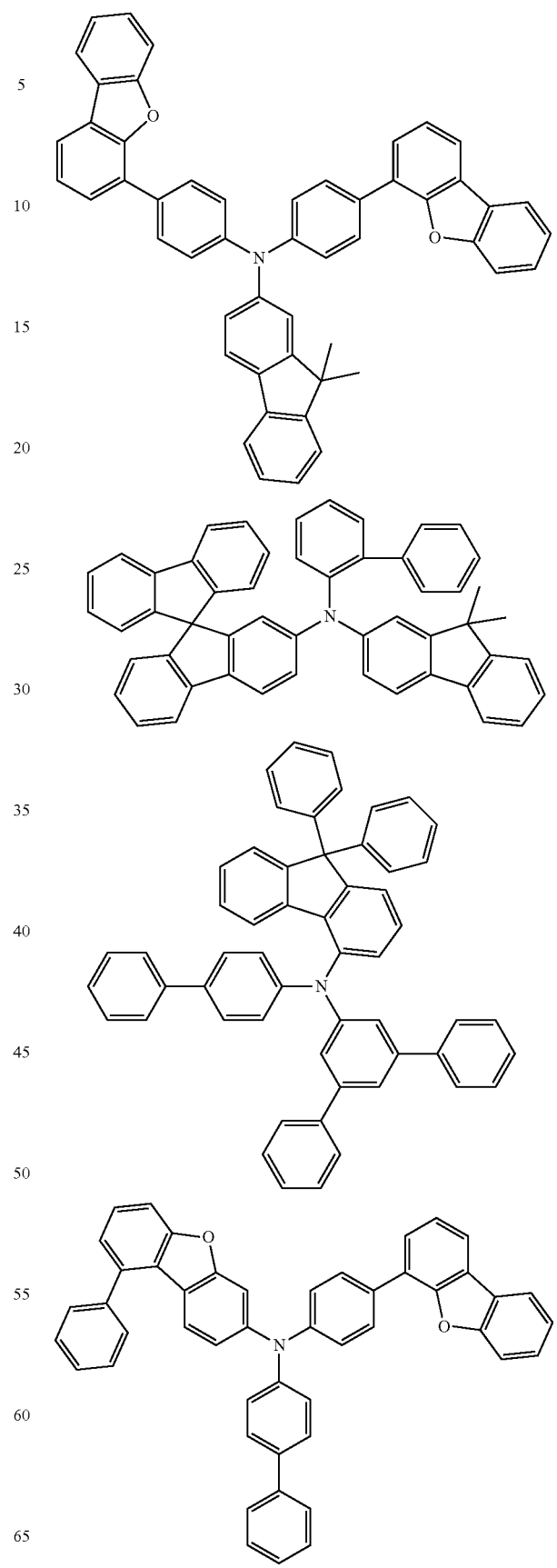 |

103
-continued
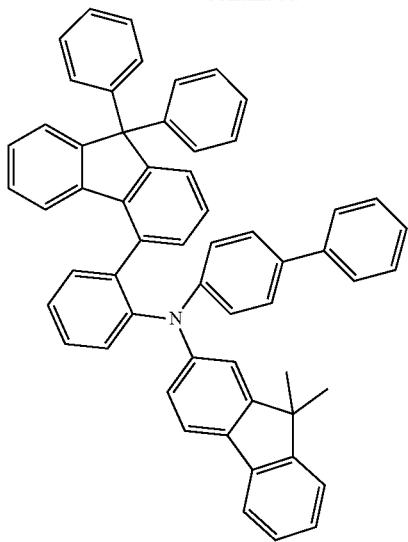
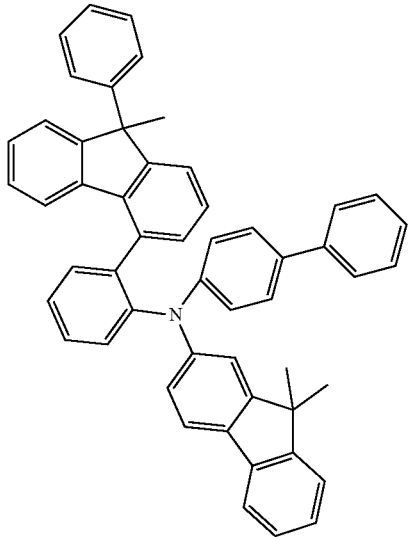
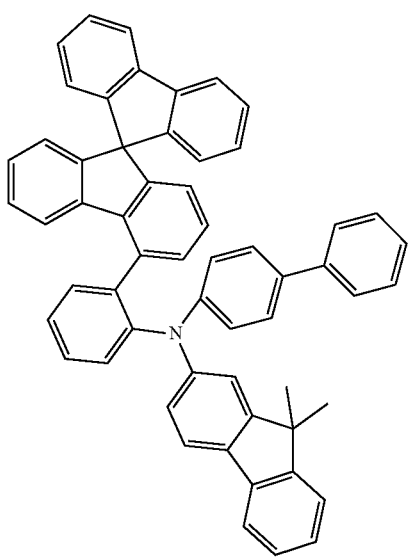
104
-continued
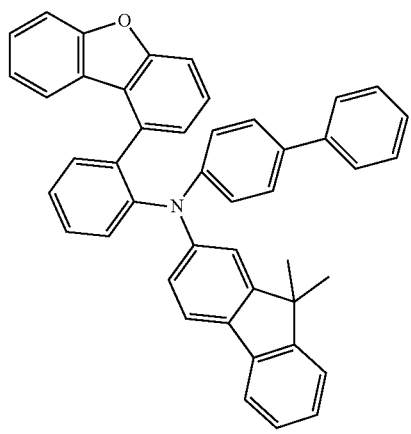
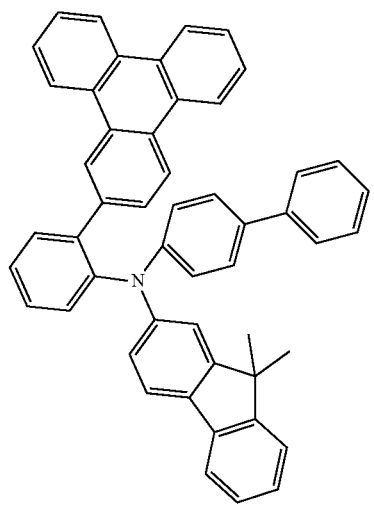
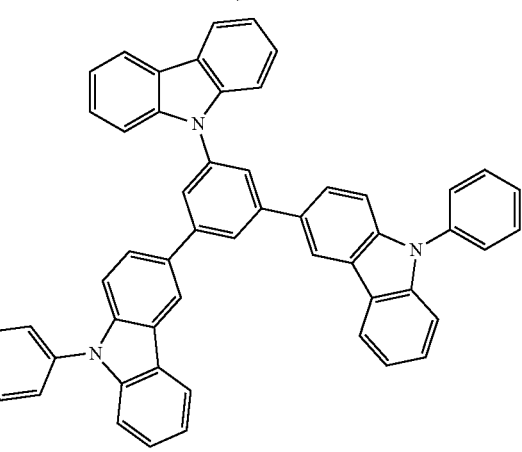
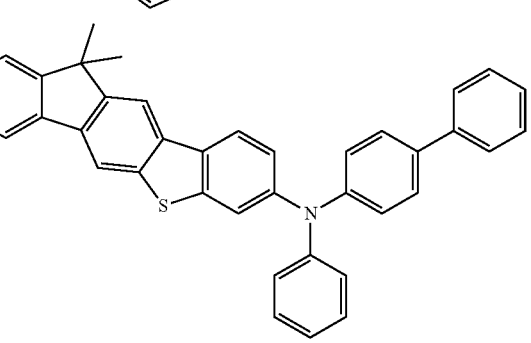

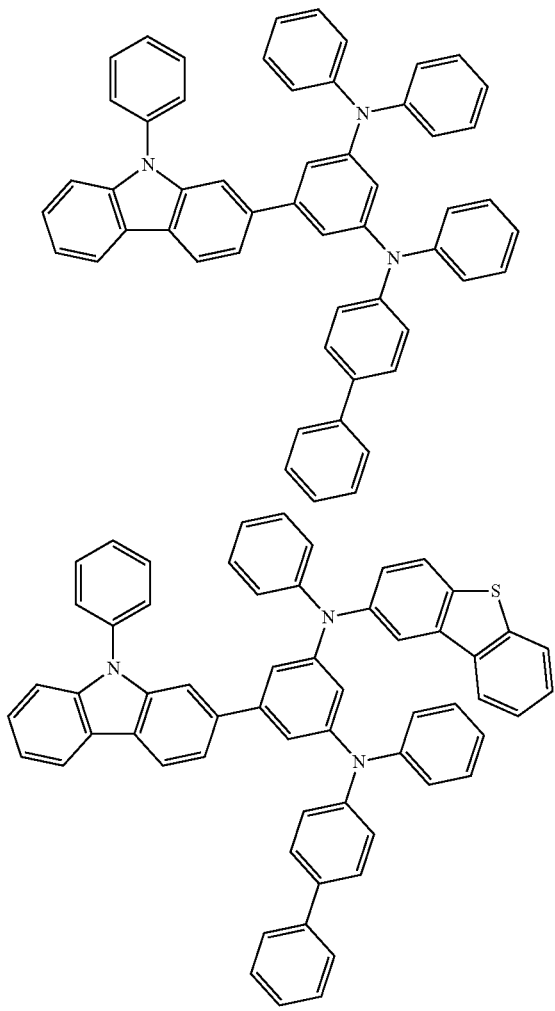
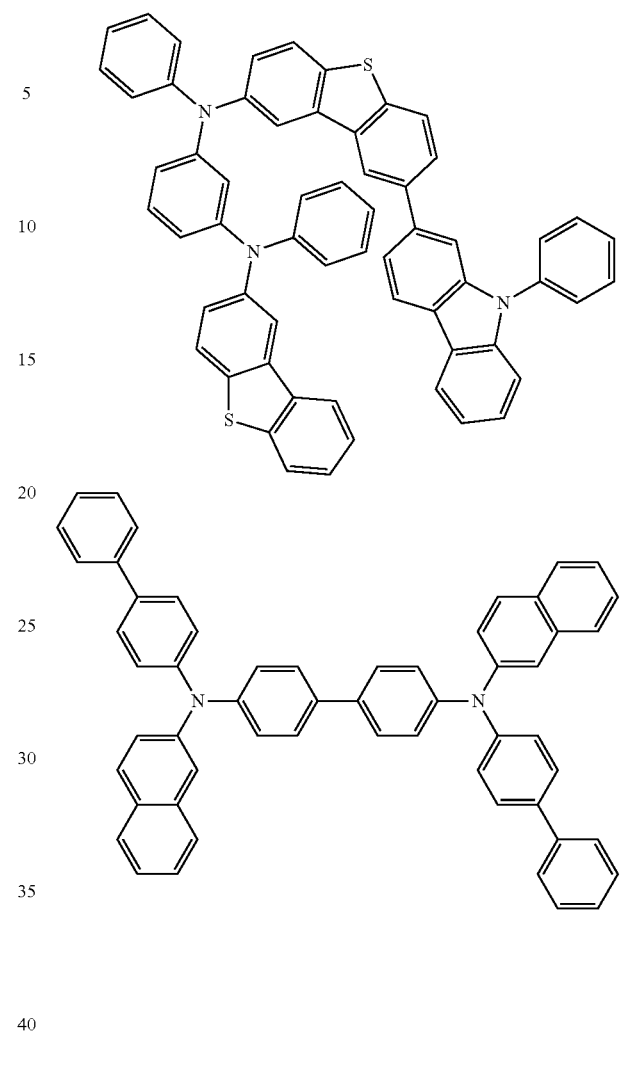
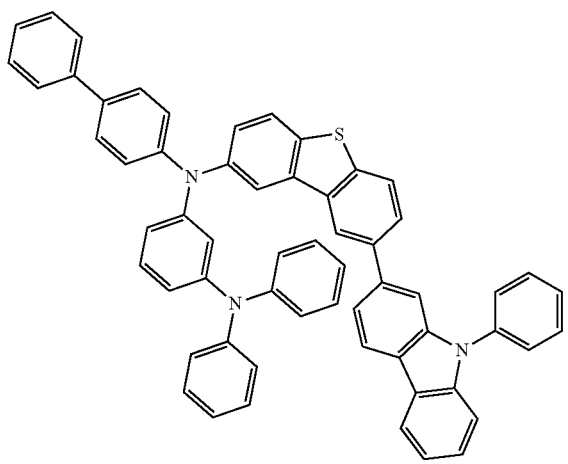

107
-continued
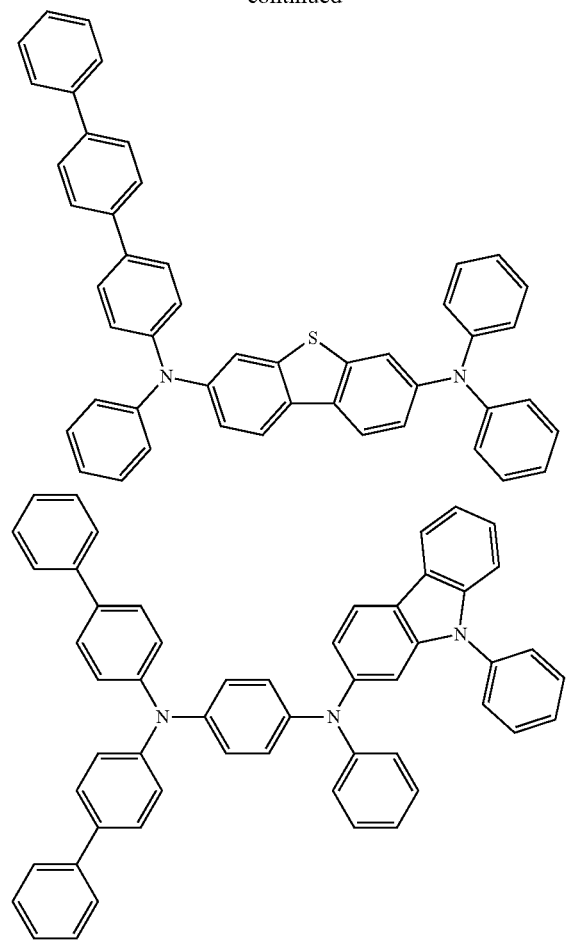
108
-continued
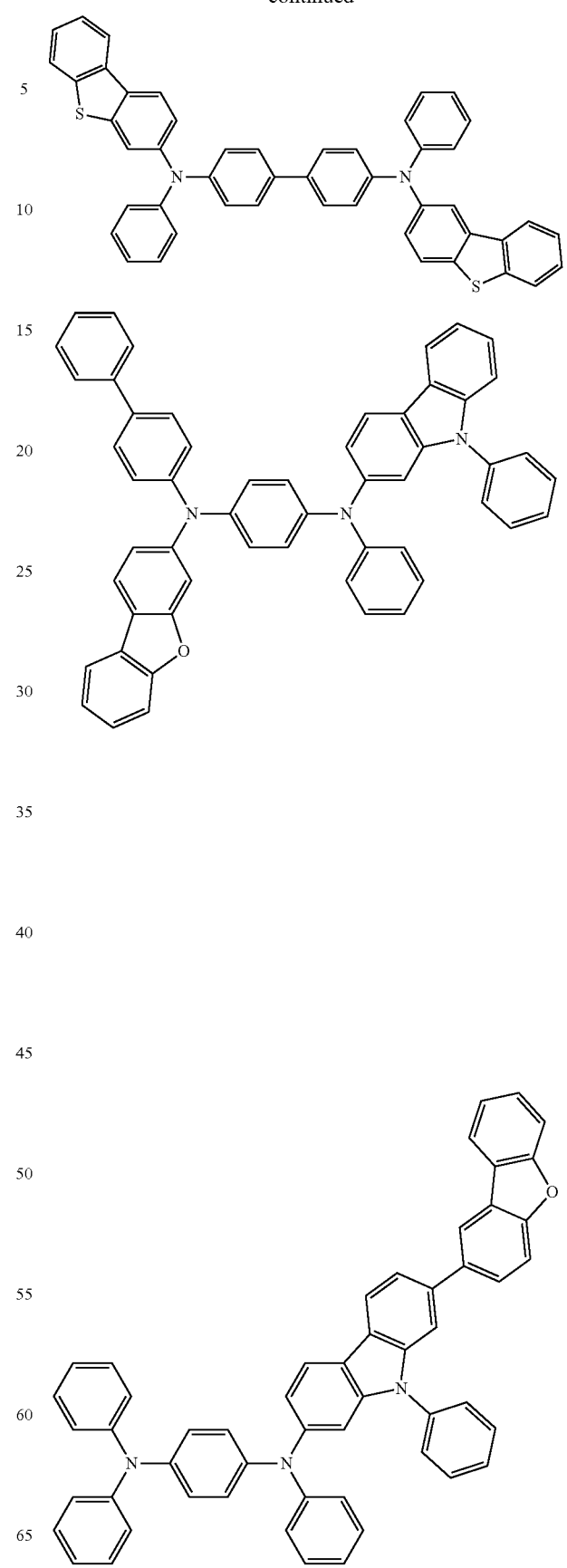

109
-continued
110
-continued
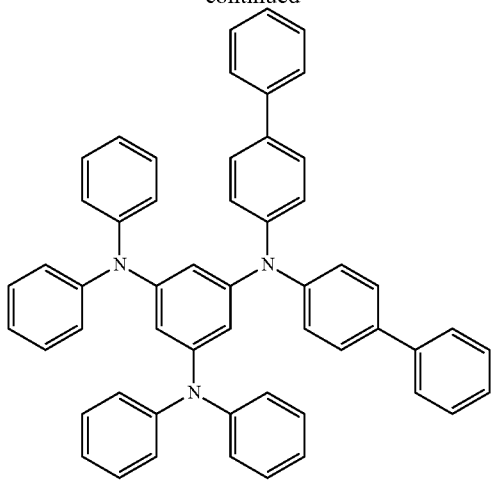
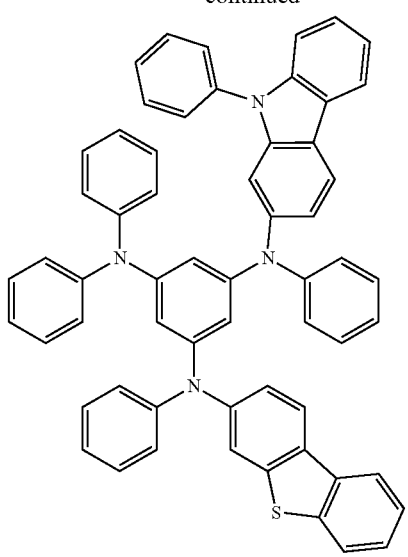
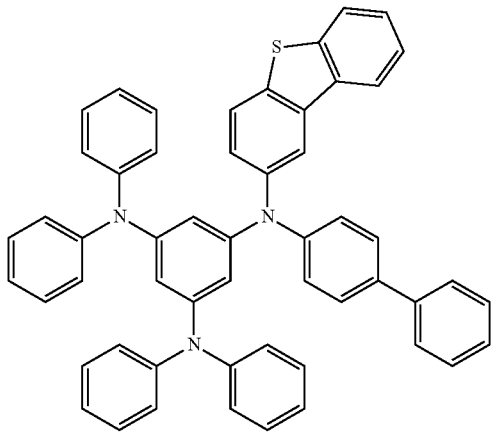
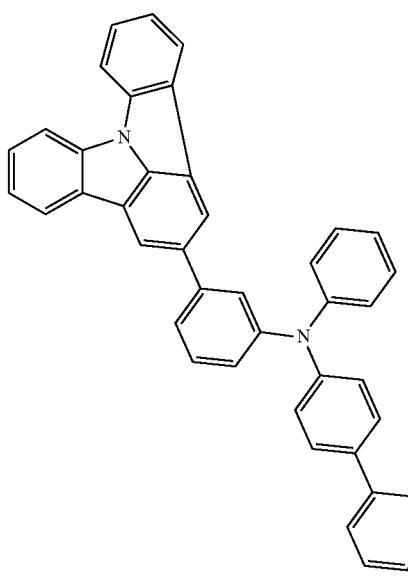
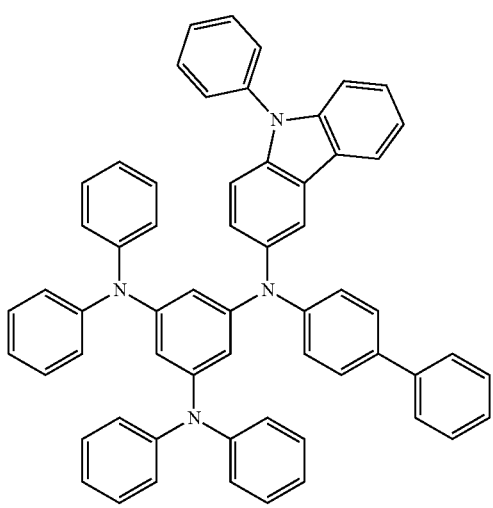
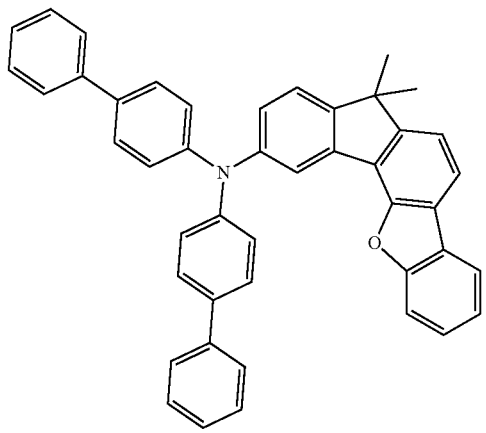

111
-continued
112
-continued
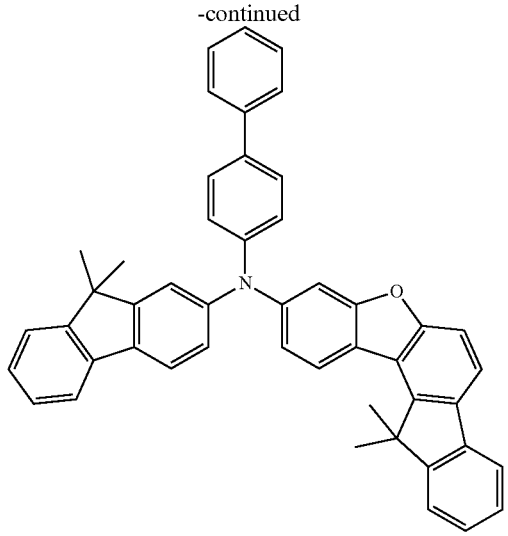
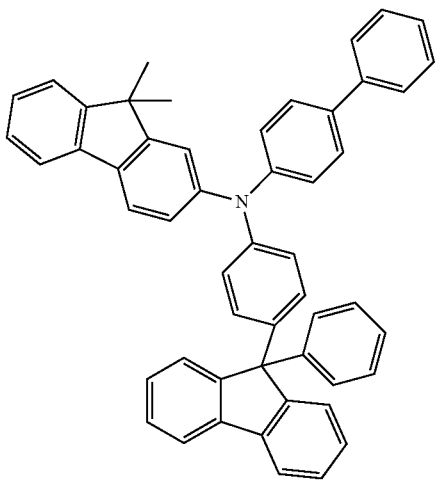
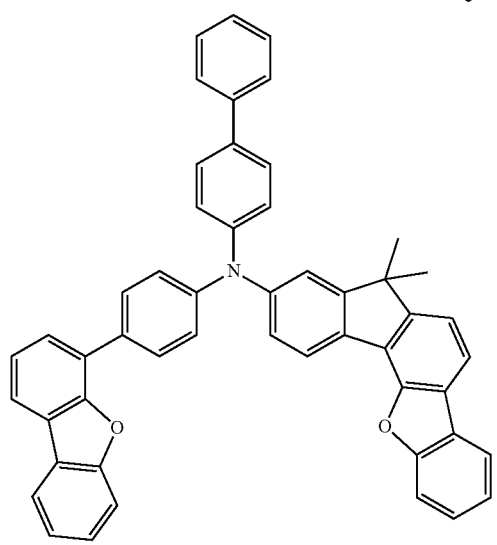
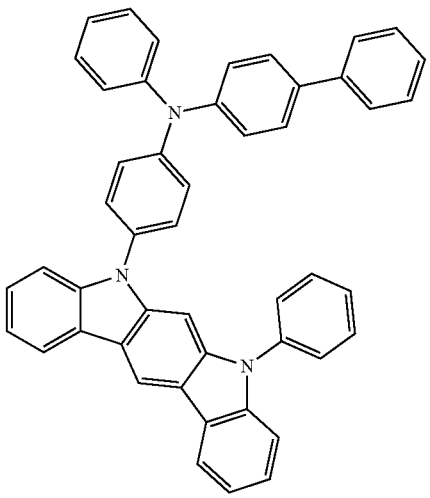
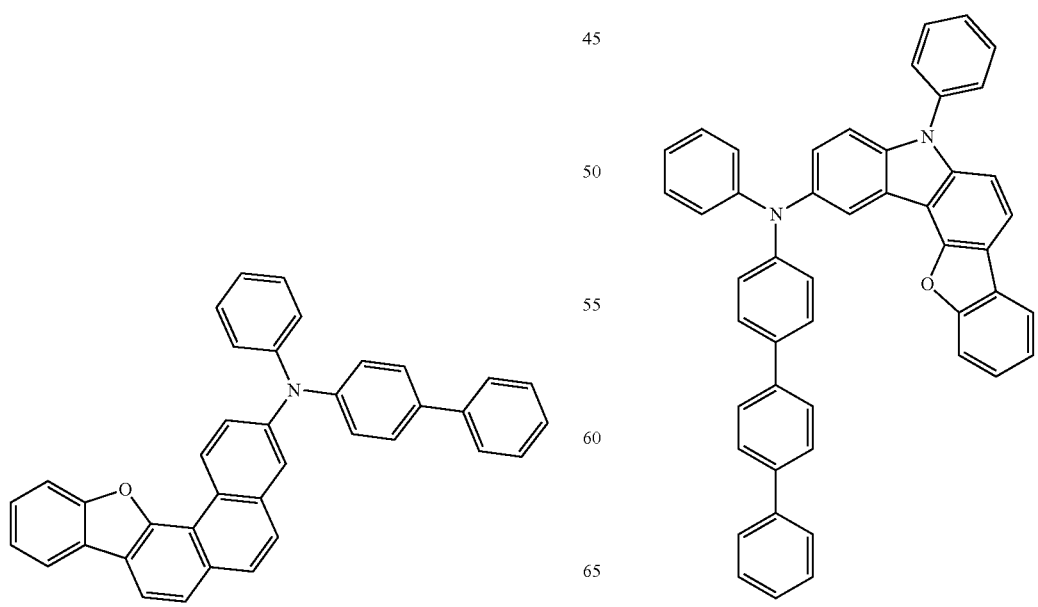

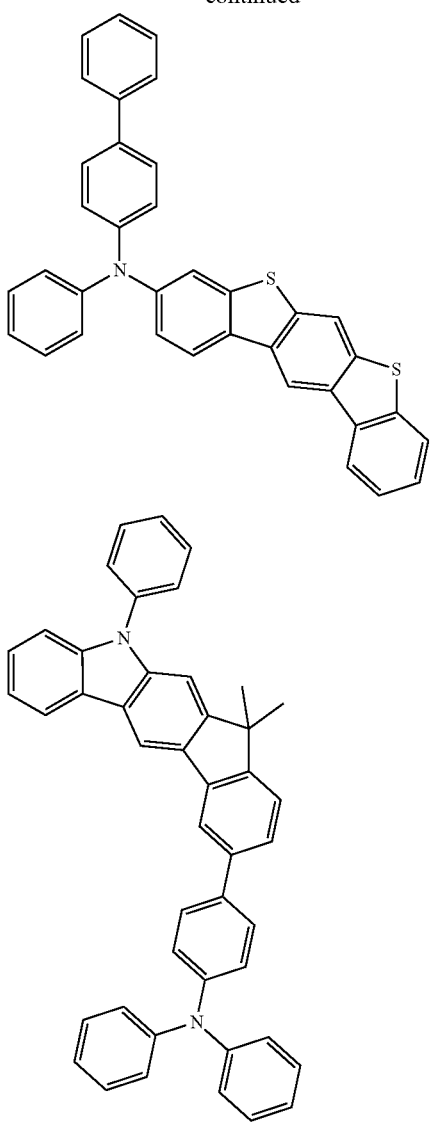

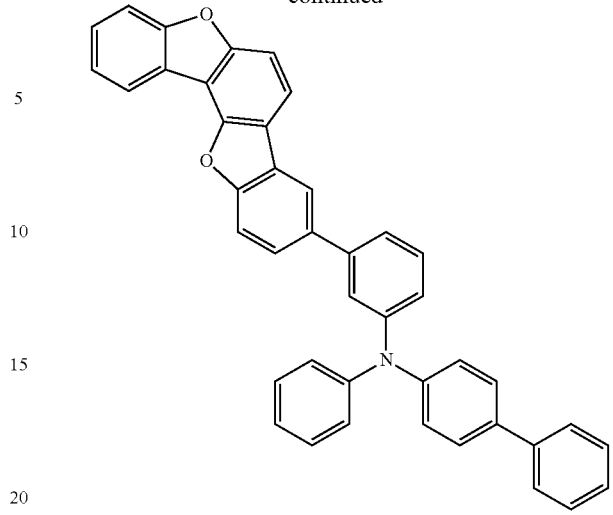

In the hole transport auxiliary layer, known compounds disclosed in U.S. Pat. No. 5,061,569A, JP1993-009471A, WO1995-009147A1, JP1995-126615A, JP1998-095973A, and the like and compounds similar thereto may be used in addition to the compounds.

In an embodiment of the present invention, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

MODE FOR INVENTION

Hereinafter, the embodiments are illustrated in more detail with reference to examples. However, these examples are exemplary, and the present scope is not limited thereto.

Preparation of First Compound

Synthesis Example 1: Synthesis of Compound A-2

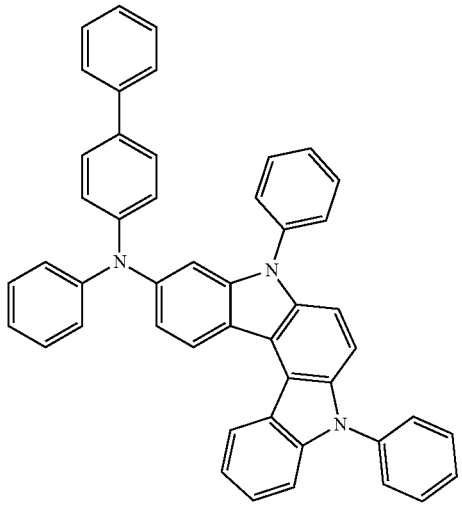

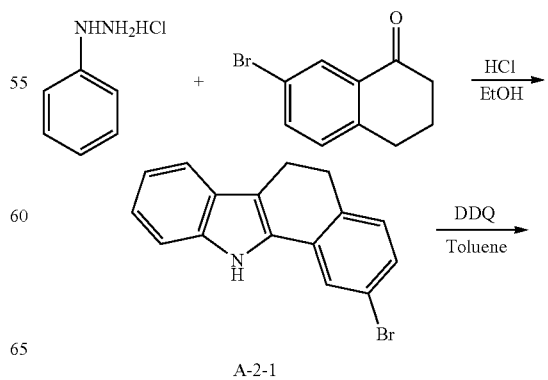

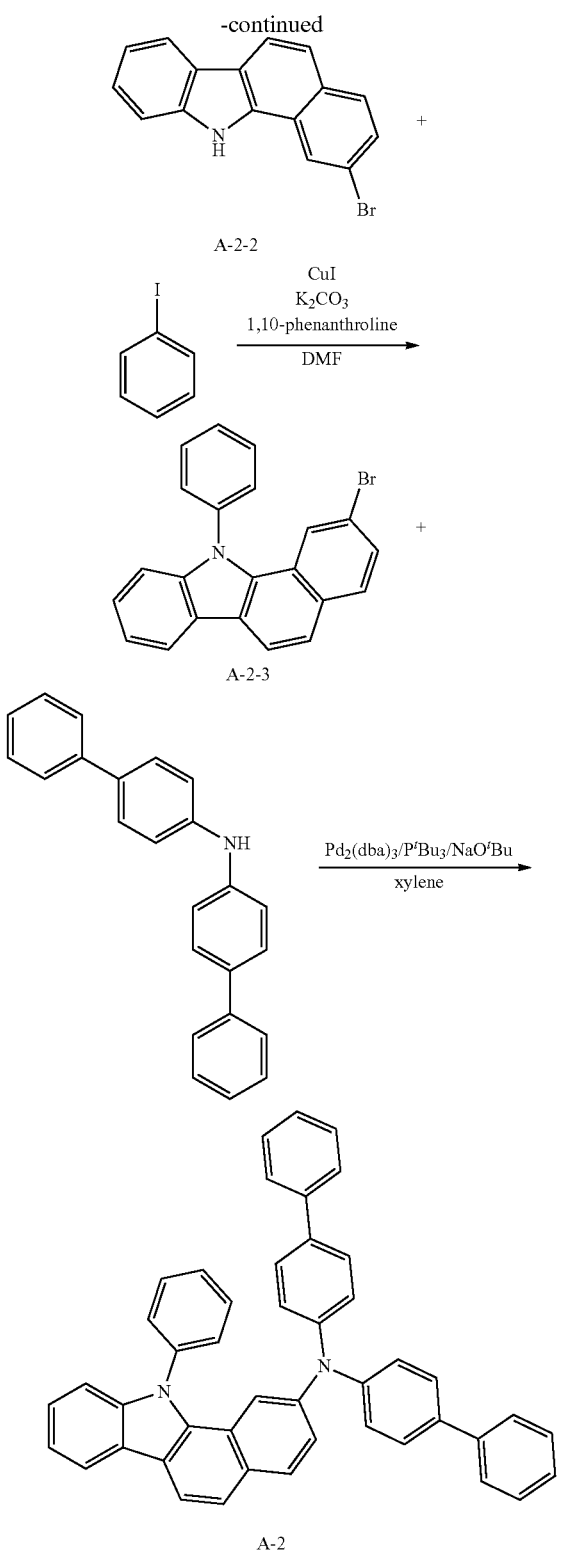

A-2-2

A-2-3

A-2 a) Synthesis of Intermediate A-2-1

Phenylhydrazine hydrochloride (70.0 g, 484.1 mmol) and 7-bromo-3,4-dihydro-2H-naphthalen-1-one (108.9 g, 484.1 mmol) were put in a round-bottomed flask and then, dissolved in ethanol (1200 ml). 60 mL of hydrochloric acid was slowly added in a dropwise fashion thereto at room temperature, and the obtained mixture was stirred at 90° C. for 12 hours. When a reaction was complete, the solvent was removed therefrom under a reduced pressure, and an extract was obtained therefrom by using an excessive amount of EA. After removing the organic solvent under a reduced pressure, the extract was stirred in a small amount of methanol and then, filtered to obtain 95.2 g of Intermediate A-2-1 (66%).

b) Synthesis of Intermediate A-2-2

Intermediate A-2-1 (95.2 g, 319.3 mmol) and 2,3-dichloro-5,6-dicyano-1,4-benzoquinone (108.7 g, 478.9 mmol) were put in a round-bottomed flask and dissolved in 600 ml of toluene. The solution was stirred at 80° C. for 12 hours. When a reaction was complete, a reaction solvent was removed, and the rest thereof was treated through column chromatography to obtain 41.3 g of Intermediate A-2-2 (44%).

c) Synthesis of Intermediate A-2-3

Intermediate A-2-2 (41.3 g, 139.0 mmol), iodobenzene (199.2 g, 976.0 mmol), CuI (5.31 g, 28.0 mmol), $K_2CO_3$ (28.9 g, 209.0 mmol), and 1,10-phenanthroline (5.03 g, 28.0 mmol) were put in a round-bottomed flask and dissolved in 500 ml of DMF. The solution was stirred at 180° C. for 12 hours. When a reaction was complete, the reaction solvent was removed therefrom under a reduced pressure, and then, a product therefrom was dissolved in dichloromethane and silica gel-filtered. After dichloromethane concentration, the filtered product was recrystallized with hexane to obtain 39.0 g of Intermediate A-2-3 (75%).

d) Synthesis of Compound A-2

Intermediate A-2-3 (23.2 g, 62.5 mmol), bis-biphenyl-4-yl-amine (21.1 g, 65.6 mmol), sodium t-butoxide (NaOtBu) (9.0 g, 93.8 mmol), $Pd_2(dba)_3$ (3.4 g, 3.7 mmol), and tri t-butylphosphine $(P(tBu)_3)$ (4.5 g, 50% in toluene) were put in xylene (300 mL) and then, heated and refluxed under a nitrogen flow for 12 hours. After removing the xylene, 200 mL of methanol was added thereto to crystallize a solid, the solid was filtered, dissolved in toluene, and filtered again with silica gel/Celite, and then, the organic solvent in an appropriate amount was concentrated to obtain 29 g of Compound A-2 (76%).

LC/MS calculated for: C46H32N2 Exact Mass: 612.26 found for 612.32 [M+H]

Synthesis Example 2: Synthesis of Compound A-3

[Reaction Scheme 2]

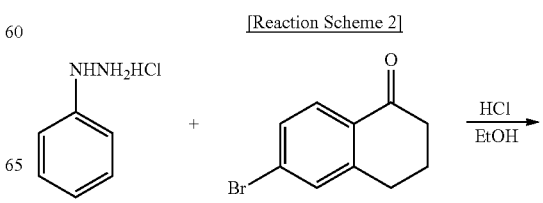

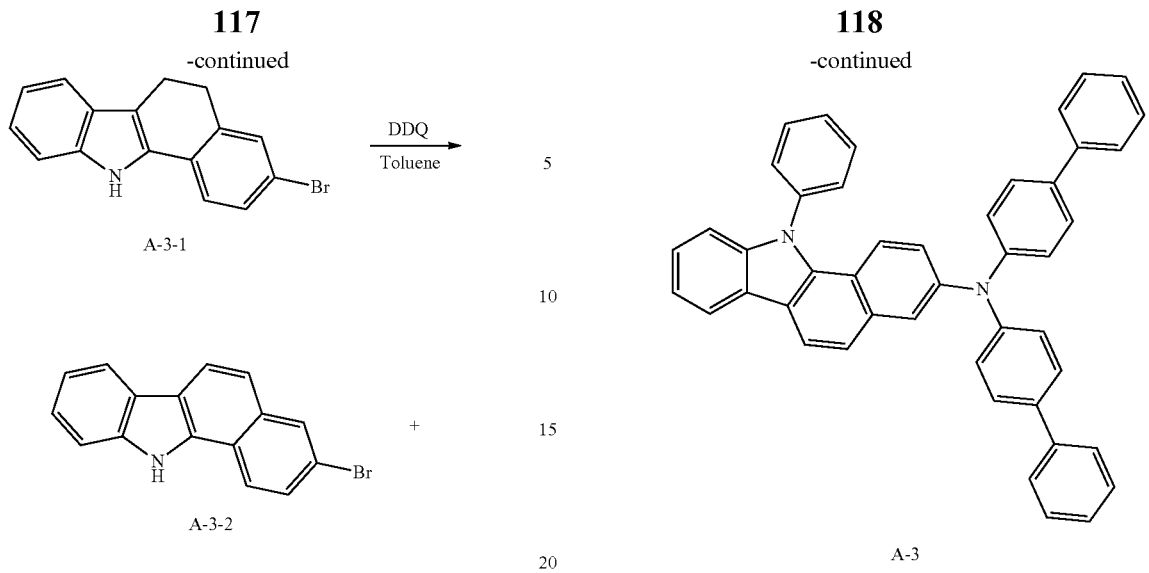

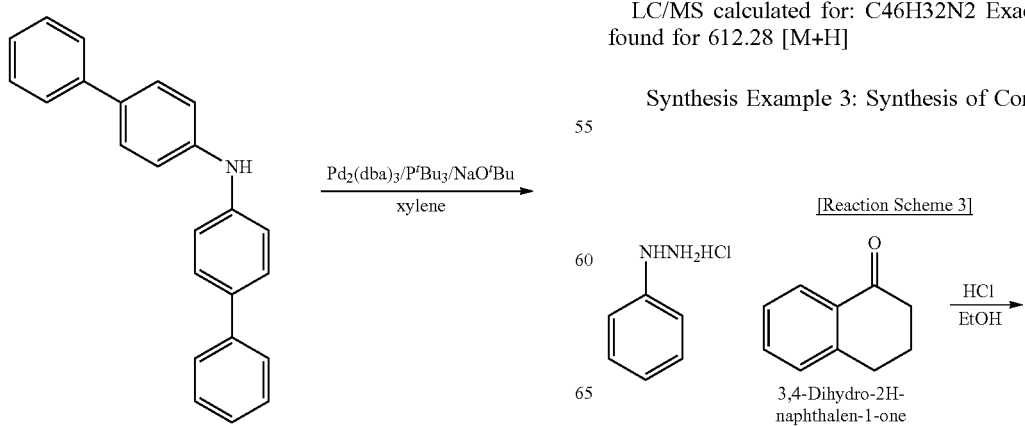

a) Synthesis of Intermediate A-3-1

Intermediate A-3-1 was synthesized according to the same method as the a) of Synthesis Example 1 by respectively using phenylhydrazinehydrochloride and 6-bromo-3,4-dihydro-2H-naphthalen-1-one by 1.0 equivalent.

b) Synthesis of Intermediate A-3-2

Intermediate A-3-2 was synthesized according to the same method as the b) of Synthesis Example 1 by using Intermediate A-3-1 and 2,3-dichloro-5,6-dicyano-1,4-benzoquinone in an equivalent ratio of 1:1.5.

c) Synthesis of Intermediate A-3-3

Intermediate A-3-3 was synthesized according to the same method as the c) of Synthesis Example 1 by using Intermediate A-3-2 and iodobenzene in an equivalent ratio of 1:3.

d) Synthesis of Compound A-3

Compound A-3 was synthesized according to the same method as the d) of Synthesis Example 1 by using Intermediate A-3-3 and bis-biphenyl-4-yl-amine in an equivalent ratio of 1:1.

LC/MS calculated for: C46H32N2 Exact Mass: 612.26 found for 612.28 [M+H]

Synthesis Example 3: Synthesis of Compound A-5

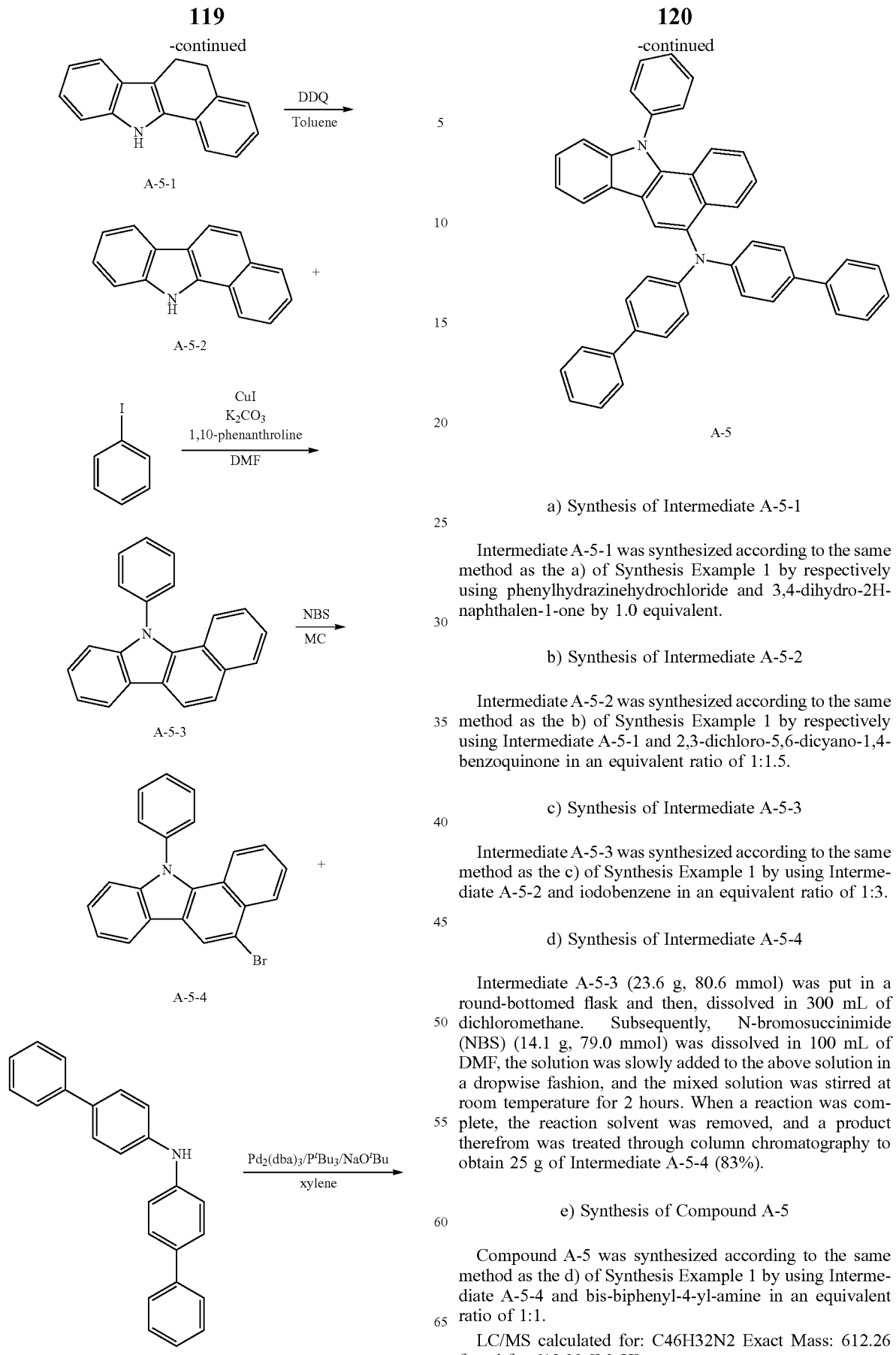

a) Synthesis of Intermediate A-5-1

Intermediate A-5-1 was synthesized according to the same method as the a) of Synthesis Example 1 by respectively using phenylhydrazinehydrochloride and 3,4-dihydro-2H-naphthalen-1-one by 1.0 equivalent.

b) Synthesis of Intermediate A-5-2

Intermediate A-5-2 was synthesized according to the same method as the b) of Synthesis Example 1 by respectively using Intermediate A-5-1 and 2,3-dichloro-5,6-dicyano-1,4-benzoquinone in an equivalent ratio of 1:1.5.

c) Synthesis of Intermediate A-5-3

Intermediate A-5-3 was synthesized according to the same method as the c) of Synthesis Example 1 by using Intermediate A-5-2 and iodobenzene in an equivalent ratio of 1:3.

d) Synthesis of Intermediate A-5-4

Intermediate A-5-3 (23.6 g, 80.6 mmol) was put in a round-bottomed flask and then, dissolved in 300 mL of dichloromethane. Subsequently, N-bromosuccinimide (NBS) (14.1 g, 79.0 mmol) was dissolved in 100 mL of DMF, the solution was slowly added to the above solution in a dropwise fashion, and the mixed solution was stirred at room temperature for 2 hours. When a reaction was complete, the reaction solvent was removed, and a product therefrom was treated through column chromatography to obtain 25 g of Intermediate A-5-4 (83%).

e) Synthesis of Compound A-5

Compound A-5 was synthesized according to the same method as the d) of Synthesis Example 1 by using Intermediate A-5-4 and bis-biphenyl-4-yl-amine in an equivalent ratio of 1:1.

LC/MS calculated for: C46H32N2 Exact Mass: 612.26 found for 612.33 [M+H]

Synthesis Example 4: Synthesis of Compound A-7

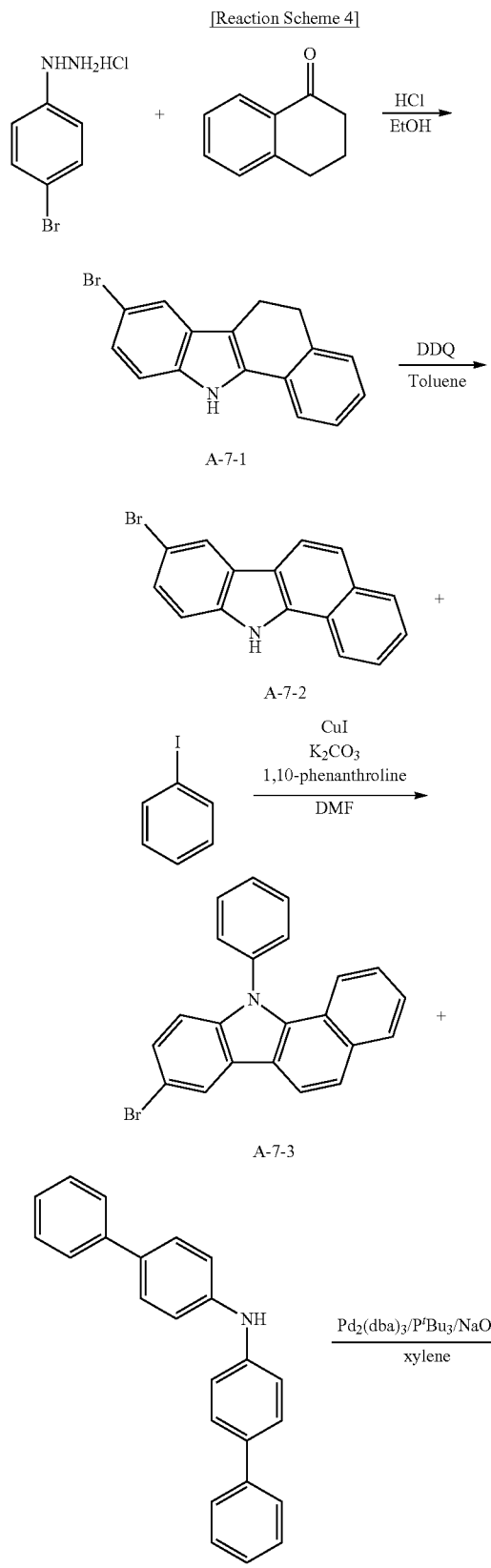

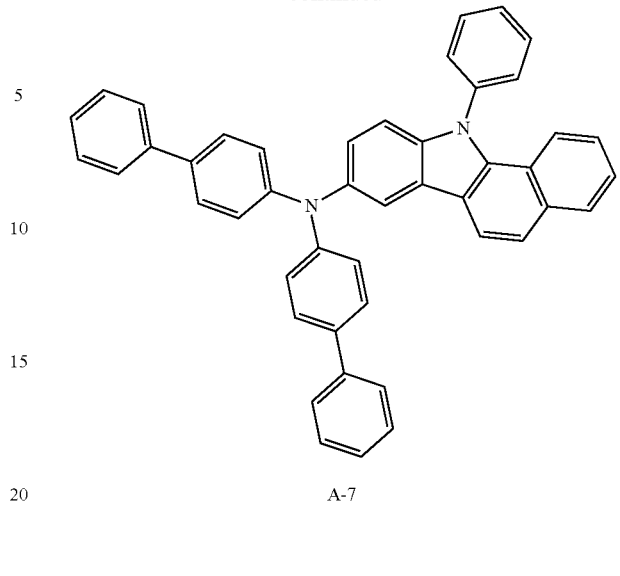

a) Synthesis of Intermediate A-7-1

Intermediate A-7-1 was synthesized according to the same method as the a) of Synthesis Example 1 by respectively using 4-bromophenylhydrazinehydrochloride and 3,4-dihydro-2H-naphthalen-1-one by 1.0 equivalent.

b) Synthesis of Intermediate A-7-2

Intermediate A-7-2 was synthesized according to the same method as the b) of Synthesis Example 1 by using Intermediate A-7-1 and 2,3-dichloro-5,6-dicyano-1,4-benzoquinone in an equivalent ratio of 1:1.5.

c) Synthesis of Intermediate A-7-3

Intermediate A-7-3 was synthesized according to the same method as the c) of Synthesis Example 1 by using Intermediate A-7-2 and iodobenzene in an equivalent ratio of 1:3.

d) Synthesis of Compound A-7

Compound A-7 was synthesized according to the same method as the d) of Synthesis Example 1 by using Intermediate A-7-3 and bis-biphenyl-4-yl-amine in an equivalent ratio of 1:1.

LC/MS calculated for: C46H32N$_2$ Exact Mass: 612.26 found for 612.30 [M+H]

Synthesis Example 5: Synthesis of Compound A-8

[Reaction Scheme 5]

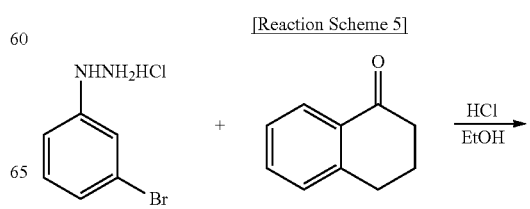

-continued

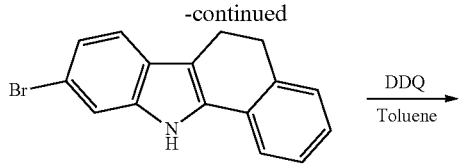
A-8-1

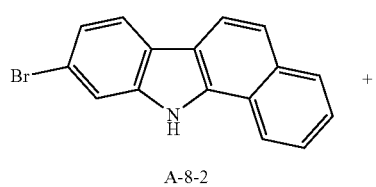
A-8-2

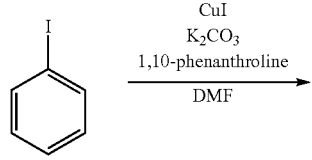

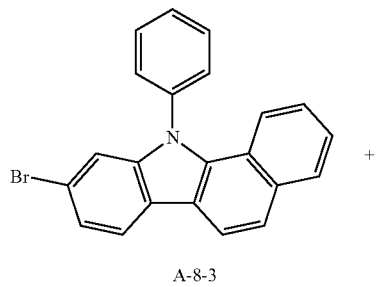
A-8-3

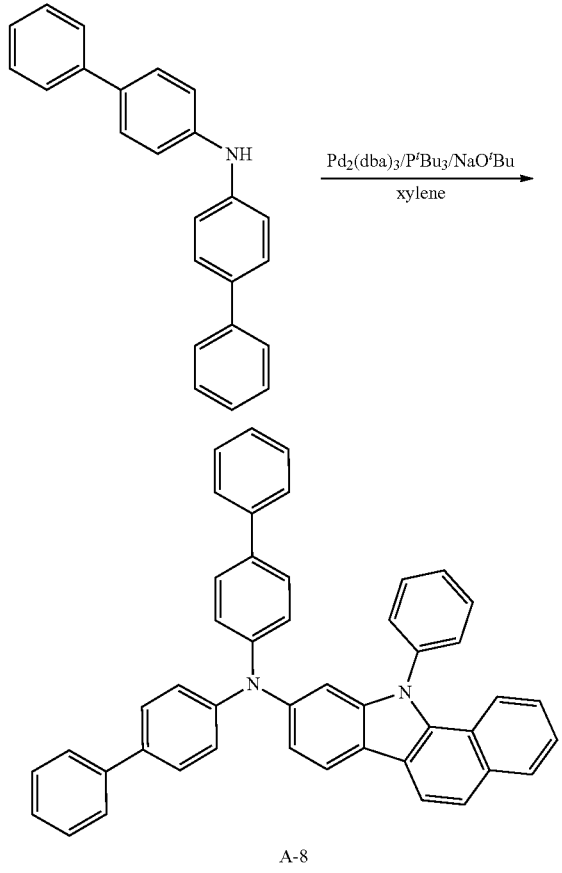
A-8 a) Synthesis of Intermediate A-8-1

Intermediate A-8-1 was synthesized according to the same method as the a) of Synthesis Example 1 by respectively using 3-bromophenylhydrazinehydrochloride and 3,4-di-hydro-2H-naphthalen-1-one by 1.0 equivalent.

b) Synthesis of Intermediate A-8-2

Intermediate A-8-2 was synthesized according to the same method as the b) of Synthesis Example 1 by using Intermediate A-8-1 and 2,3-dichloro-5,6-dicyano-1,4-benzoquinone in an equivalent ratio of 1:1.5.

c) Synthesis of Intermediate A-8-3

Intermediate A-8-3 was synthesized according to the same method as the c) of Synthesis Example 1 by using Intermediate A-8-2 and iodobenzene in an equivalent ratio of 1:3.

d) Synthesis of Compound A-8

Compound A-8 was synthesized according to the same method as the d) of Synthesis Example 1 by using Intermediate A-8-3 and bis-biphenyl-4-yl-amine in an equivalent ratio of 1:1.

LC/MS calculated for: C46H32N2 Exact Mass: 612.26 found for 612.33 [M+H]

Synthesis Example 6: Synthesis of Compound A-11

[Reaction Scheme 6]

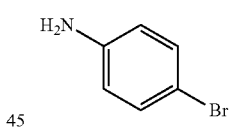

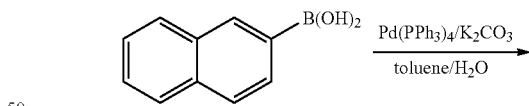

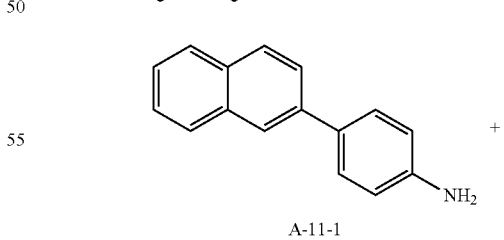
A-11-1

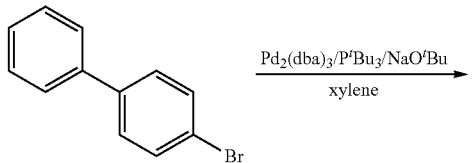

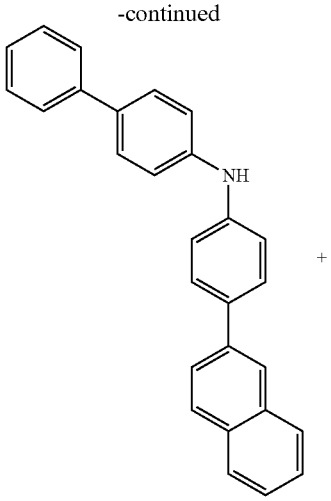

A-11-2

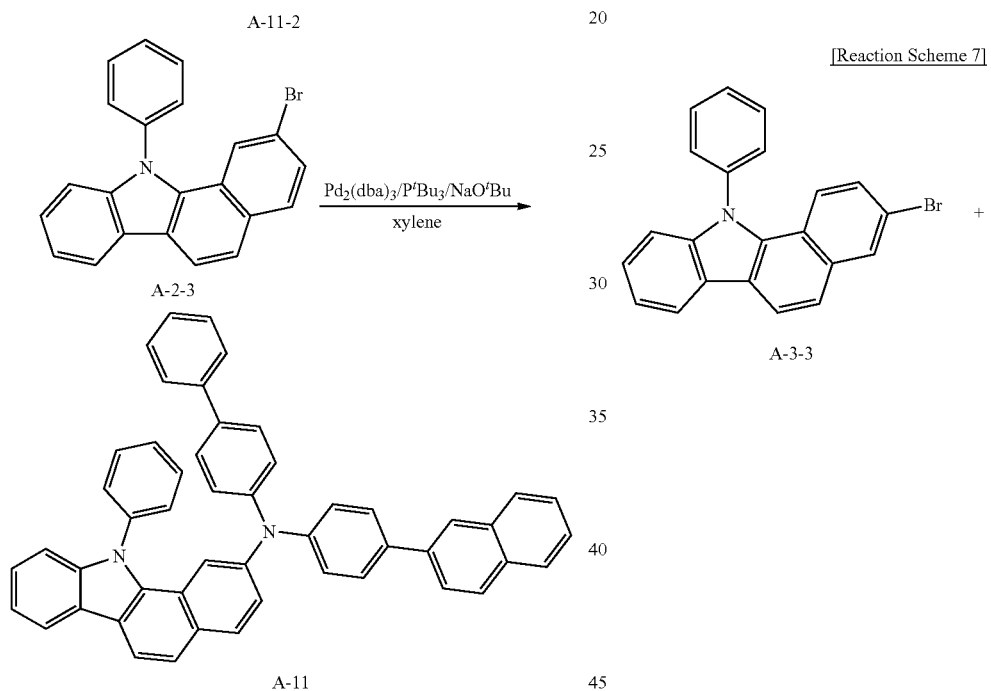

A-11 a) Synthesis of Intermediate A-11-1

4-bromo-phenylamine (50.0 g, 290.7 mmol), 2-naphthalene boronic Acid (59.9 g, 171.9 mmol), K$_2$CO$_3$ (80.4 g, 581.3 mmol), and Pd(PPh$_3$)$_4$ (10.1 g, 8.7 mmol) were put in a round-bottomed flask and dissolved in 800 ml of toluene and 400 ml of distilled water, and the solution was stirred at 80° C. for 12 hours. When a reaction was complete, an aqueous layer was removed therefrom, and the rest thereof was treated through column chromatography to obtain 40.0 g of Intermediate A-11-1 (63%).

b) Synthesis of Intermediate A-11-2

Intermediate A-11-1 (17.7 g, 80.8 mmol), 4-bromo-biphenyl (18.8 g, 80.8 mmol), sodium t-butoxide (NaOtBu) (11.6 g, 121.1 mmol), Pd$_2$(dba)$_3$ (4.4 g, 4.8 mmol), and tri t-butylphosphine (P(tBu)$_3$) (5.9 g, 50% in toluene) were added to xylene (400 mL) and then, heated and refluxed together under a nitrogen flow for 12 hours. After removing the xylene, the rest thereof was treated through column chromatography to obtain 20.0 g of Intermediate A-11-2 (67%).

c) Synthesis of Compound A-11

Compound A-11 was synthesized according to the same method as the d) of Synthesis Example 1 by using Intermediate A-11-2 and Intermediate A-2-3 in an equivalent ratio of 1:1.

LC/MS calculated for: C50H34N2 Exact Mass: 662.27 found for 662.31 [M+H]

Synthesis Example 7: Synthesis of Compound A-12

[Reaction Scheme 7]

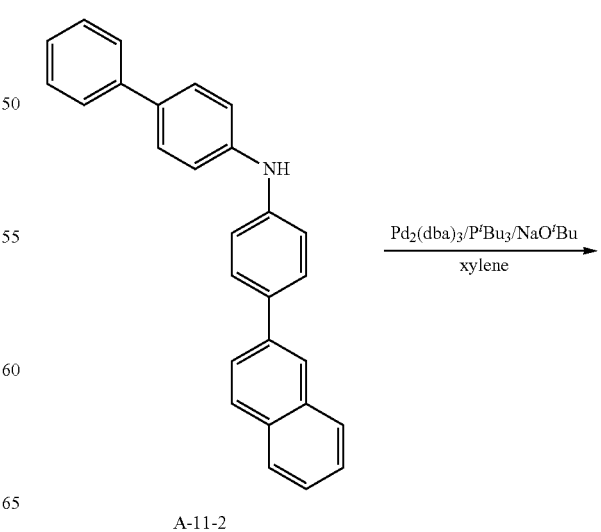

A-11-2

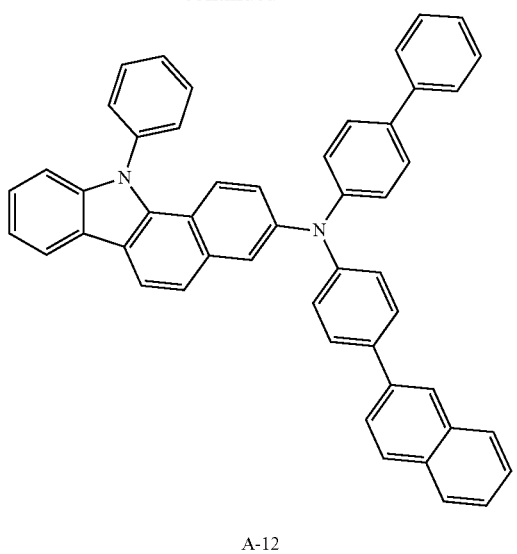

A-12

Compound A-12 was synthesized according to the same method as the d) of Synthesis Example 1 by using Intermediate A-3-3 and Intermediate A-11-2 in an equivalent ratio of 1:1.

LC/MS calculated for: C50H34N$_2$ Exact Mass: 662.27 found for 662.30 [M+H]

Synthesis Example 8: Synthesis of Compound A-29

[Reaction Scheme 8]

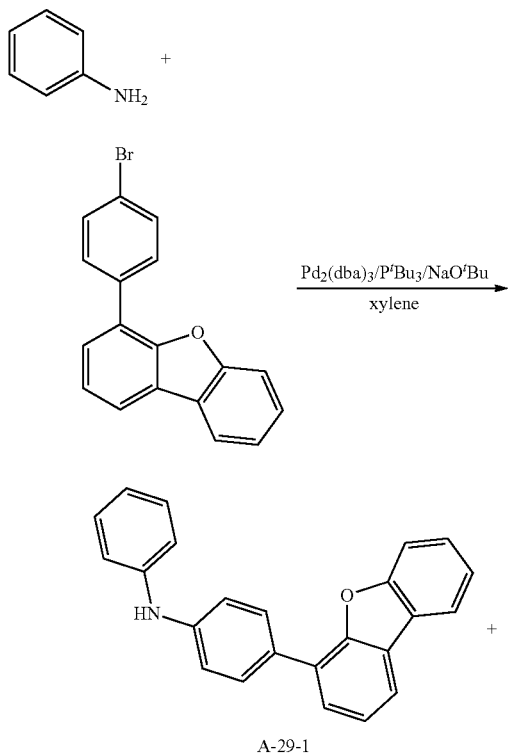

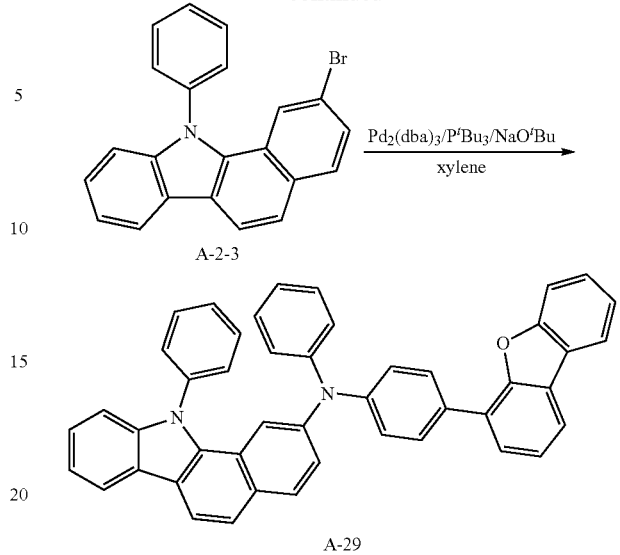

a) Synthesis of Intermediate A-29-1

Aniline (8.3 g, 89.5 mmol), 4-(4-bromo-phenyl)-dibenzofuran (23.1 g, 71.5 mmol), sodium t-butoxide (NaOtBu) (12.9 g, 134.2 mmol), Pd$_2$(dba)$_3$ (4.9 g, 5.4 mmol), and tri t-butylphosphine (P(tBu)$_3$) (6.5 g, 50% in toluene) were added to xylene (400 mL) and then, heated and refluxes together under a nitrogen flow for 12 hours. After removing the xylene, the rest thereof was treated through column chromatography to obtain 20.0 g of Intermediate A-29-1 (67%).

b) Synthesis of Compound A-29

Compound A-29 was synthesized according to the same method as the d) of Synthesis Example 1 by using Intermediate A-29-1 and Intermediate A-2-3 in an equivalent ratio of 1:1.

LC/MS calculated for: C46H30N2O Exact Mass: 626.24 found for 626.28 [M+H]

Synthesis Example 9: Synthesis of Compound A-38

[Reaction Scheme 9]

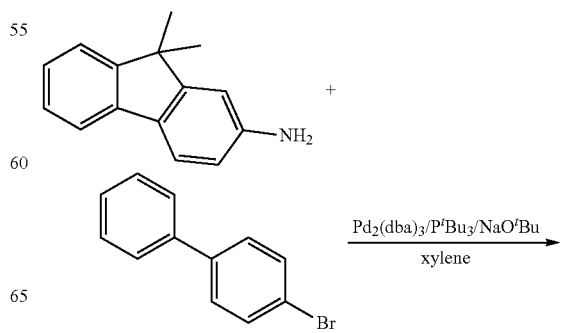

-continued

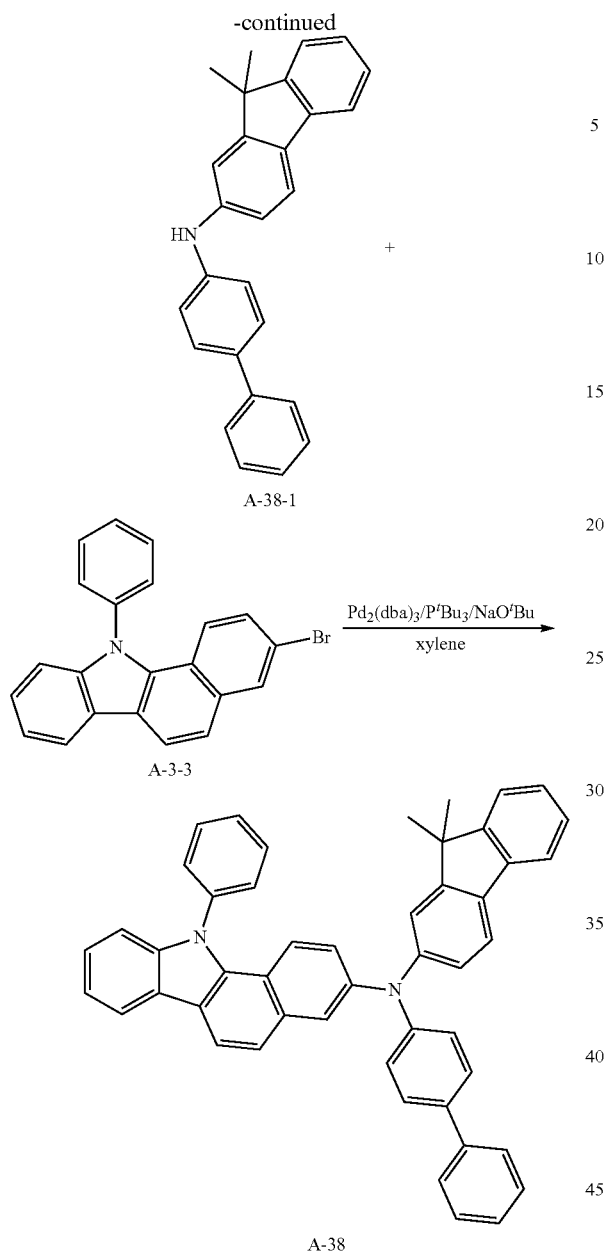

a) Synthesis of Intermediate A-38-1

9,9-Dimethyl-9H-fluoren-2-ylamine (17.4 g, 83.0 mmol), 4-bromo-biphenyl (15.5 g, 66.4 mmol), sodium t-butoxide (NaOtBu) (12.0 g, 124.5 mmol), Pd$_2$(dba)$_3$ (4.6 g, 5.0 mmol), and tri t-butylphosphine (P(tBu)$_3$) (6.0 g, 50% in toluene) were put in xylene (400 mL) and then, heated and refluxed under a nitrogen flow for 12 hours. After removing the xylene, the rest thereof was treated through column chromatography to obtain 18.0 g of Intermediate A-38-1 (60%).

b) Synthesis of Compound A-38

Compound A-38 was synthesized according to the same method as the d) of Synthesis Example 1 by using Intermediate A-38-1 and Intermediate A-3-3 in an equivalent ratio of 1:1.

LC/MS calculated for: C49H36N2 Exact Mass: 652.29 found for 652.33 [M+H]

Synthesis Example 10: Synthesis of Compound A-51

[Reaction Scheme 10]

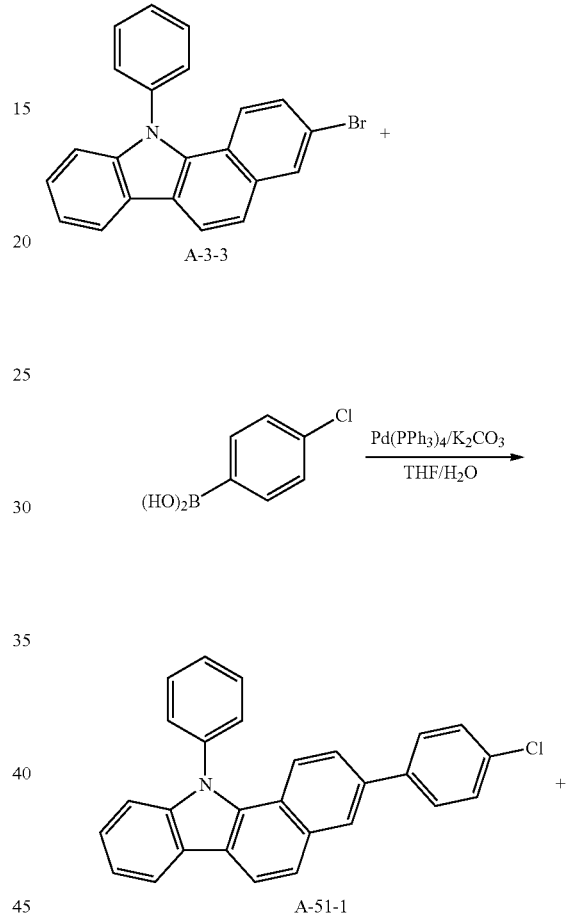

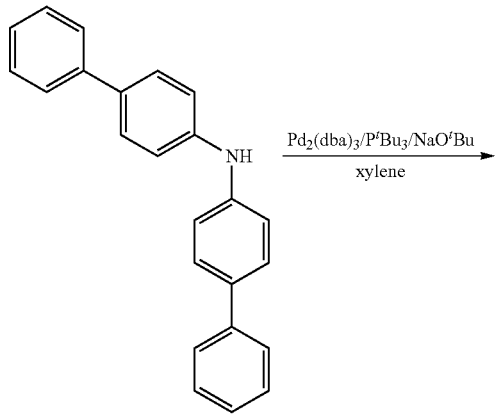

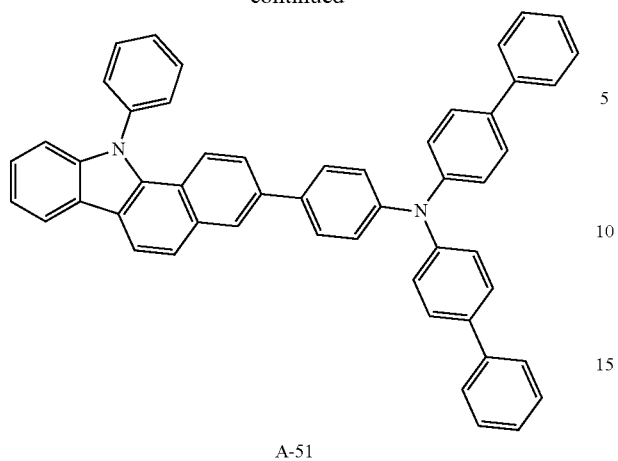

A-51 a) Synthesis of Intermediate A-51-1

Intermediate A-3-3 (30.0 g, 80.6 mmol), 4-chlorophenyl boronic acid (15.1 g, 96.7 mmol), $K_2CO_3$ (22.3 g, 161.2 mmol), and $Pd(PPh_3)_4$ (2.8 g, 2.4 mmol) were put in a round-bottomed flask and then, dissolved in 200 ml of tetrahydrofuran and 100 ml of distilled water, and the solution was stirred at 80° C. for 12 hours. When a reaction was complete, an aqueous layer was removed, and the rest thereof was treated through column chromatography to obtain 27.0 g of Intermediate A-51-1 (83%).

b) Synthesis of Compound A-51

Compound A-51 was synthesized according to the same method as the d of Synthesis Example 1 by using Intermediate A-51-1 and bis-biphenyl-4-yl-amine in an equivalent ratio of 1:1.

LC/MS calculated for: C52H36N2 Exact Mass: 688.29 found for 688.34 [M+H]

Synthesis Example 11: Synthesis of Compound A-65

[Reaction Scheme 11]

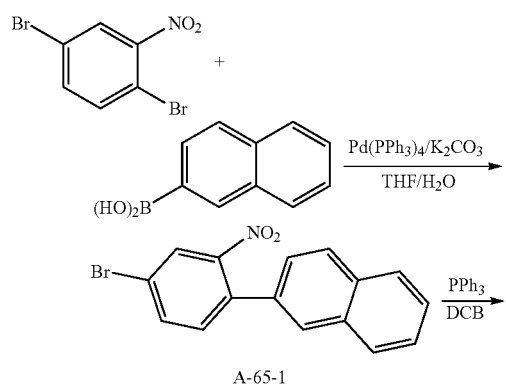

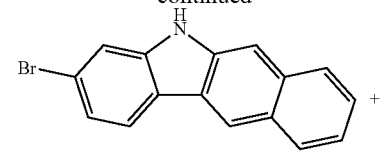

A-65-2

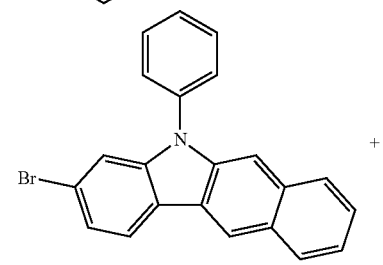

A-65-3

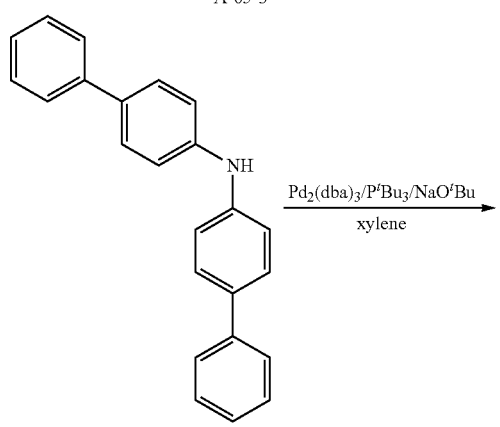

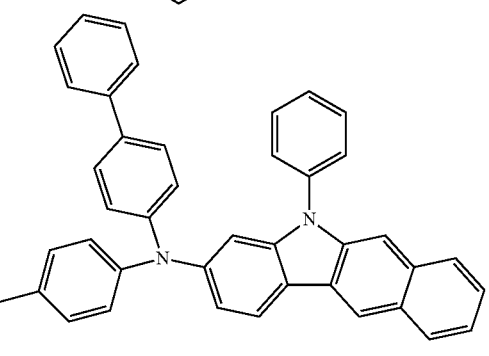

A-65 a) Synthesis of Intermediate A-65-1

1,4-Dibromo-2-nitro-benzene (30.0 g, 106.8 mmol), 2-naphthalene boronic acid (18.4 g, 106.8 mmol), $K_2CO_3$ (29.5 g, 213.6 mmol), and $Pd(PPh_3)_4$ (3.7 g, 3.2 mmol) were put in a round-bottomed flask and then, dissolved in 300 mL of tetrahydrofuran and 150 mL of distilled water, and the solution was stirred at 80° C. for 12 hours. When a reaction was complete, an aqueous layer was removed, and the rest thereof was treated through column chromatography to obtain 27.0 g of Intermediate A-65-1 (77%).

b) Synthesis of Intermediate A-65-2

Intermediate A-65-1 (27.0 g, 82.3 mmol) and triphenylphosphine (86.3 g, 329.1 mmol) were put in a round-bottomed flask and then, dissolved in 300 mL of 1,2-dichlorobenzene, and the solution was stirred at 180° C. for 12 hours. When a reaction was complete, a solvent was removed therefrom, and the rest thereof was treated through column chromatography to obtain 18.0 g of Intermediate A-65-2 (74%).

c) Synthesis of Intermediate A-65-3

Intermediate A-65-3 was synthesized according to the same method as the c) of Synthesis Example 1 by using Intermediate A-65-2 and iodobenzene in an equivalent ratio of 1:3.

d) Synthesis of Compound A-65

Intermediate A-65 was synthesized according to the same method as the d) of Synthesis Example 1 by using Intermediate A-65-3 and bis-biphenyl-4-yl-amine in an equivalent ratio of 1:1.
LC/MS calculated for: C46H32N2 Exact Mass: 612.26 found for 612.30 [M+H]

Synthesis Example 12: Synthesis of Compound A-72

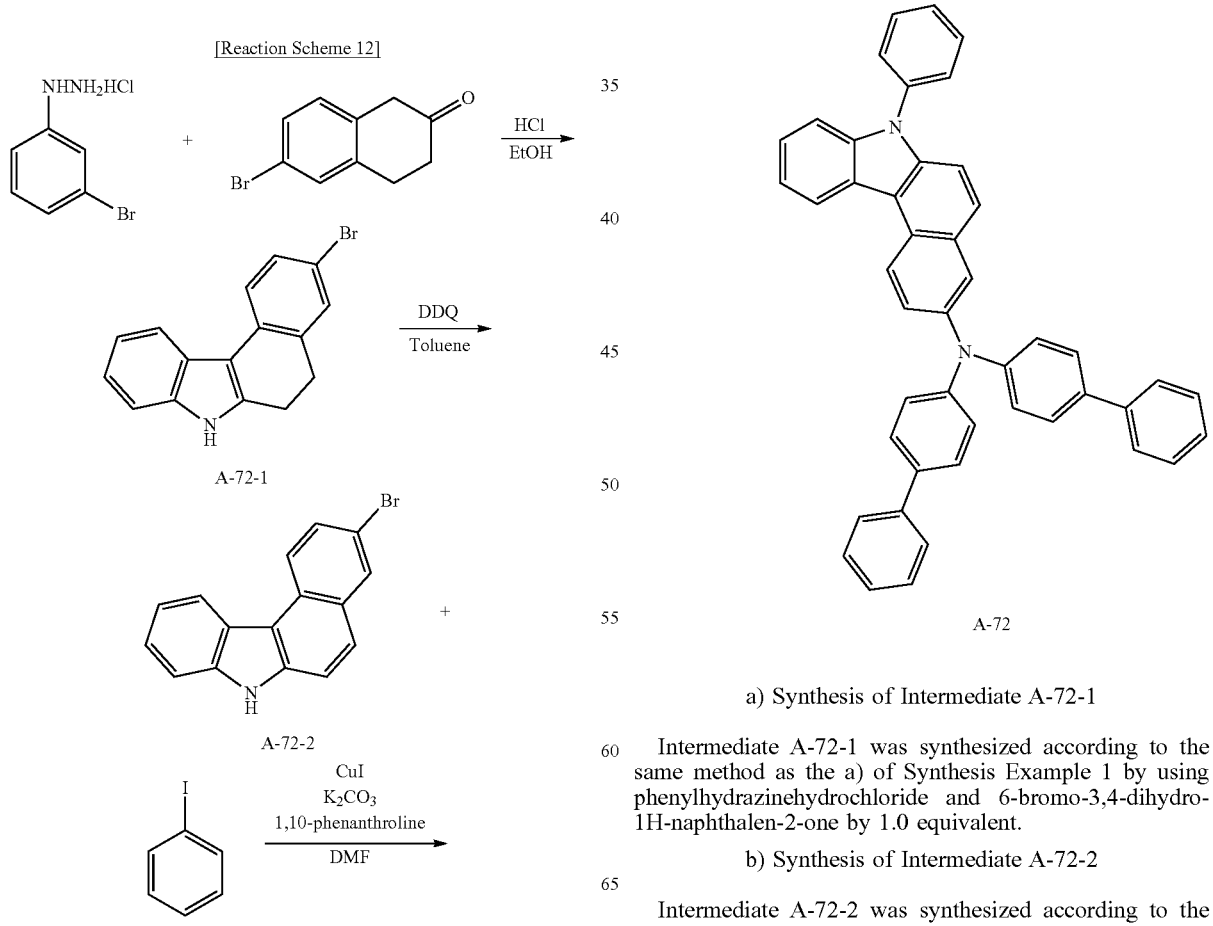

a) Synthesis of Intermediate A-72-1

Intermediate A-72-1 was synthesized according to the same method as the a) of Synthesis Example 1 by using phenylhydrazinehydrochloride and 6-bromo-3,4-dihydro-1H-naphthalen-2-one by 1.0 equivalent.

b) Synthesis of Intermediate A-72-2

Intermediate A-72-2 was synthesized according to the same method as the b) of Synthesis Example 1 by using Intermediate A-72-1 and 2,3-dichloro-5,6-dicyano-1,4-benzoquinone in an equivalent ratio of 1:1.5.

c) Synthesis of Intermediate A-72-3

Intermediate A-72-3 was synthesized according to the same method as the c) of Synthesis Example 1 by using Intermediate A-72-2 and iodobenzene in an equivalent ratio of 1:3.

d) Synthesis of Compound A-72

Intermediate A-72 was synthesized according to the same method as the d) of Synthesis Example 1 by using Intermediate A-72-3 and bis-biphenyl-4-yl-amine in an equivalent ratio of 1:1.
LC/MS calculated for: C46H32N2 Exact Mass: 612.26 found for 612.31 [M+H]

Synthesis Example 13: Synthesis of Compound A-77

[Reaction Scheme 13]

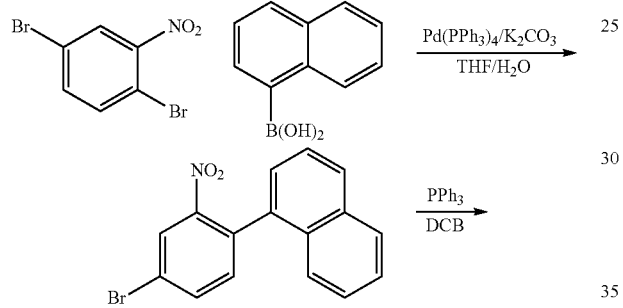

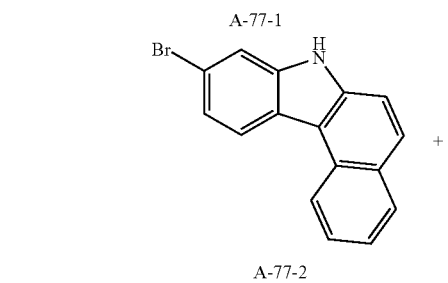

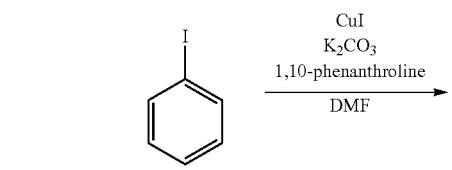

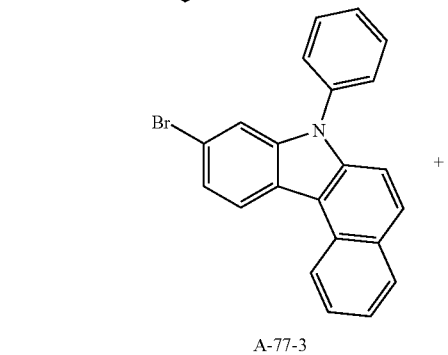

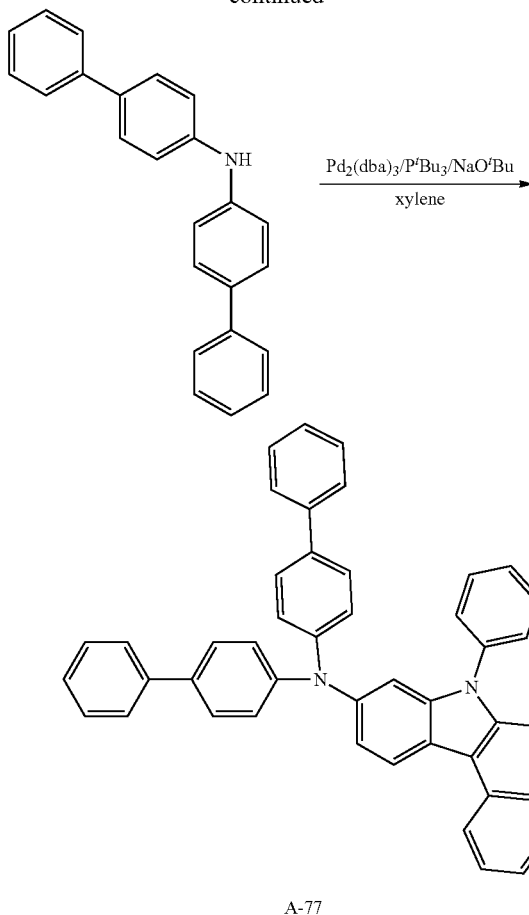

A-77 a) Synthesis of Intermediate A-77-1

Intermediate A-77-1 was synthesized according to the same method as the a) of Synthesis Example 11 by using 1,4-dibromo-2-nitro-benzene and 1-naphthalene boronic acid by 1.0 equivalent.

b) Synthesis of Intermediate A-77-2

Intermediate A-77-2 was synthesized according to the same method as the b) of Synthesis Example 11 by using Intermediate A-77-1 and triphenylphosphine in an equivalent ratio of 1:4.

c) Synthesis of Intermediate A-77-3

Intermediate A-77-3 was synthesized according to the same method as the c) of Synthesis Example 1 by using Intermediate A-77-2 and iodobenzene in an equivalent ratio of 1:3.

d) Synthesis of Compound A-77

Compound A-77 was synthesized according to the same method as the d) of Synthesis Example 1 by using Intermediate A-77-3 and bis-biphenyl-4-yl-amine in an equivalent ratio of 1:1.
LC/MS calculated for: C46H32N2 Exact Mass: 612.26 found for 612.29 [M+H] (Preparation of Second Compound)

Synthesis Example 14: Synthesis of Compound B-8

[Reaction Scheme 14]

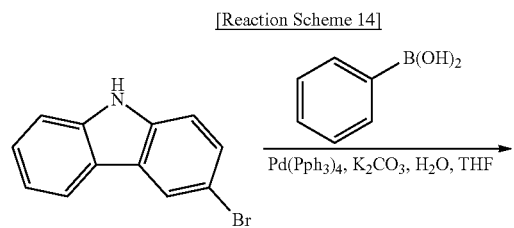

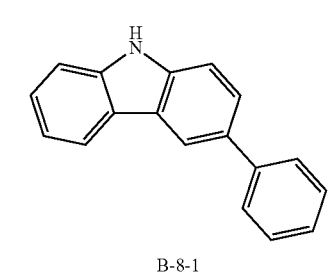

B-8-1

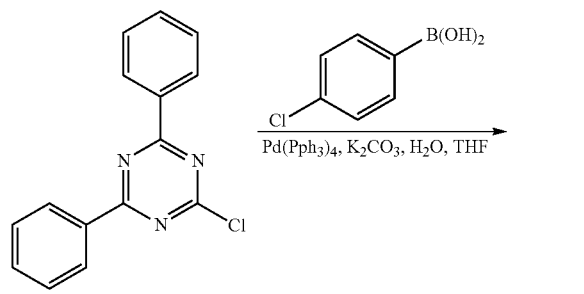

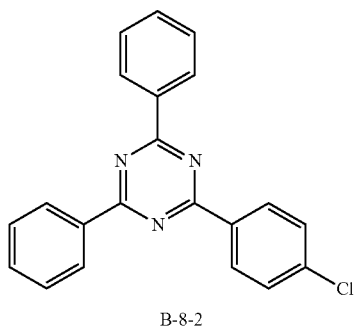

B-8-2

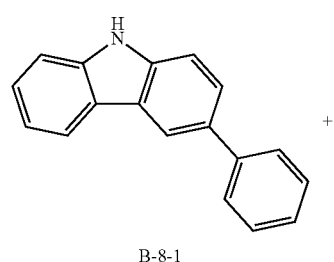

B-8-1

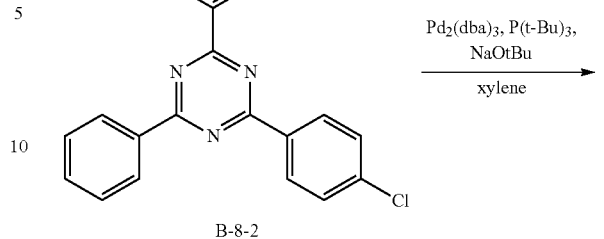

B-8-2

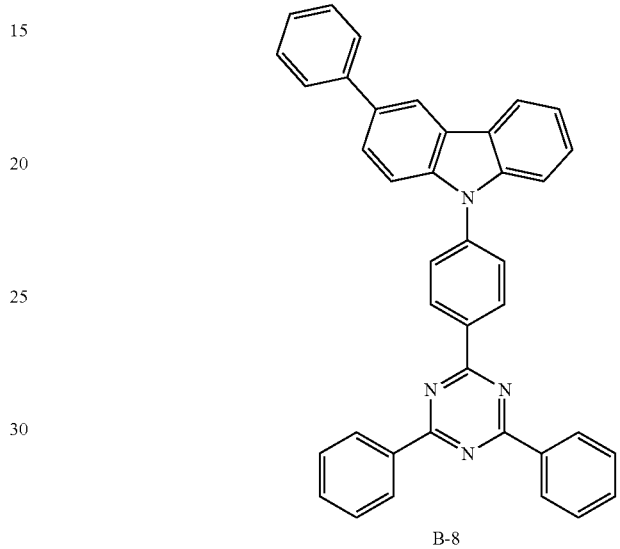

B-8 a) Synthesis of Intermediate B-8-1

3-Bromocarbazole (35 g, 142 mmol) was dissolved in 0.5 L of tetrahydrofuran (THF) in a 1 L round-bottomed flask, phenyl boronic acid (17.3 g, 142 mmol) and tetrakis(triphenylphosphine)palladium (8.2 g, 7.1 mmol) were added thereto, and the mixture was stirred. Subsequently, potassium carbonate (49.1 g, 356 mmol) saturated in water was added thereto, and the obtained mixture was heated and refluxed at 80° C. for 12 hours. When a reaction was complete, water was poured into the reaction solution, and then, an extract was obtained therefrom by using dichloromethane (DCM), treated with anhydrous magnesium sulfate to remove moisture therefrom, filtered, and concentrated under a reduced pressure. The obtained residue was separated and purified through flash column chromatography to obtain 22.0 g of Intermediate B-8-1.

b) Synthesis of Intermediate B-8-2

Intermediate B-8-1 (40 g, 164 mmol) was dissolved in 0.5 L of tetrahydrofuran (THF) in a 1 L round-bottomed flask, 2-Chloro-4,6-diphenyl-1,3,5-triazine (40 g, 149 mmol) and tetrakis(triphenylphosphine)palladium (8.63 g, 7.5 mmol) were added thereto, and the mixture was stirred. Subsequently, potassium carbonate (51.6 g, 374 mmol) saturated in water was added thereto, and the obtained mixture was heated and refluxed at 80° C. for 12 hours. When a reaction was complete, water was poured into the reaction solution, and then, an extract was obtained therefrom by using dichloromethane (DCM), treated with anhydrous magnesium sulfate to remove moisture therefrom, filtered, and concentrated under a reduced pressure. The obtained residue was separated and purified through flash column chromatography to obtain 32.1 g of Intermediate B-8-2.

c) Synthesis of Compound B-8

Intermediate B-8-1 (22.0 g, 90.4 mmol), Intermediate B-8-2 (31.1 g, 90.4 mmol), sodium t-butoxide (NaOtBu) (13.01 g, 135.6 mmol), Pd$_2$(dba)$_3$ (2.48 g, 2.7 mmol), and tri t-butylphosphine (P(tBu)$_3$) (5.49 g, 50% in toluene) were added to xylene (300 mL), and the mixture was heated and refluxed for 12 hours under a nitrogen flow. After removing the xylene therefrom, 200 mL of methanol was added thereto, a solid crystallized therein was filtered, dissolved in monochlorobenzene (MCB), and filtered with silica gel/Celite, and then, an organic solvent in an appropriate amount was concentrated therefrom to obtain Compound B-8 (32 g, 64.3%).

Synthesis Example 15: Synthesis of Compound B-12

[Reaction Scheme 15]

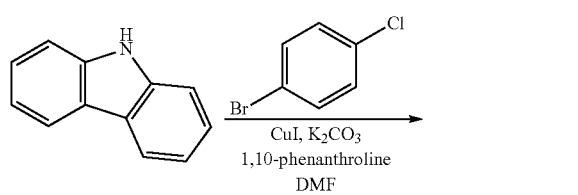

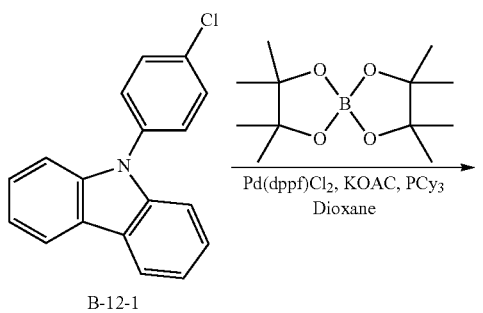

B-12-1

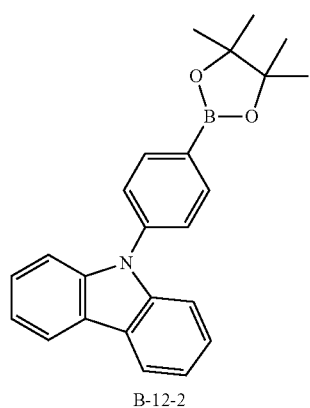

B-12-2

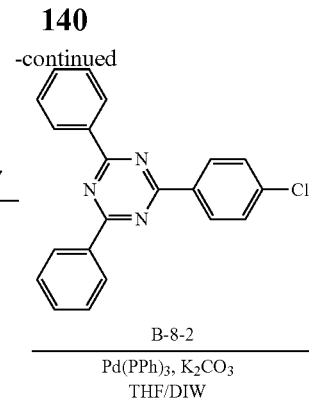

B-12-2

$\xrightarrow{\text{B-8-2}}$
$\text{Pd(PPh}_3\text{)}_3, \text{K}_2\text{CO}_3$
$\text{THF/DIW}$

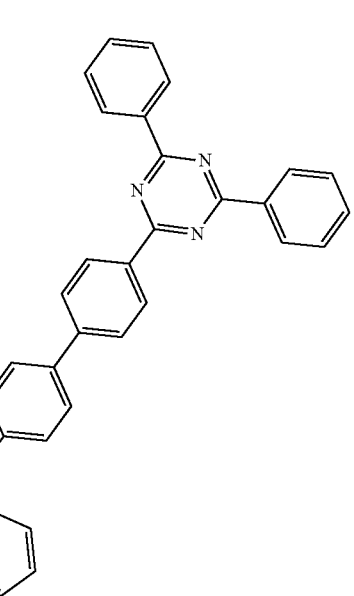

B-12 a) Synthesis of Intermediate B-12-1

Carbazole (35 g, 209.3 mmol), 1-bromo-4-chloro-benzene (60.11 g 313.98 mmol), CuI (3.99 g, 20.9 mmol), K$_2$CO$_3$ (43.39 g, 313.98 mmol), and 1,10-phenanthroline (3.77 g, 20.9 mmol) were put in a round-bottomed flask and dissolved in 700 ml of DMF. The solution was stirred at 180° C. for 18 hours. When a reaction was complete, the reaction solvent was removed therefrom under a reduced pressure, and then, a product therefrom was dissolved in dichloromethane and silica gel-filtered. After dichloromethane concentration, the filtered product was recrystallized with hexane to obtain 40.0 g of Intermediate B-12-1 (68.8%).

b) Synthesis of Intermediate B-12-2

Intermediate B-12-1 (40 g, 144 mmol), bis(pinacolato)diboron (54.86 g, 216 mmol), Pd(dppf)Cl$_2$ (7.1 g, 8.64 mmol), tricyclohexylphosphine (8.08 g, 28.8 mmol), and potassium acetate (42.4 g, 432.04 mmol) were put in a round-bottomed flask and dissolved in 7200 ml of DMF. The mixture was refluxed and stirred at 120° C. for 12 hours. When a reaction was complete, the mixture was poured into an excessive amount of distilled water, and the obtained mixture was stirred for one hour. A solid therein was filtered and dissolved in DCM. MgSO$_4$ was used to remove moisture therefrom, and an organic solvent was filtered by using a silica gel pad and removed under a reduced pressure. A solid was recrystallized with EA and hexane to obtain 31.3 g of Intermediate B-12-2 (58.9%).

c) Synthesis of Compound B-12

Intermediate B-12-2 (31 g, 83.95 mmol) was dissolved in 0.3 L of tetrahydrofuran (THF) in a 1 L round-bottomed flask, Intermediate B-8-2 (28.86 g, 83.95 mmol) and tetrakis(triphenylphosphine)palladium (4.85 g, 4.2 mmol) were added thereto, and the mixture was stirred. Subsequently, potassium carbonate (29.01 g, 209.9 mmol) saturated in water was added thereto, and the obtained mixture was heated and refluxed at 80° C. for 12 hours. When a reaction was complete, water was poured into the reaction solution, the obtained mixture was stirred for 30 minutes and filtered to obtain a solid, the solid was dissolved in monochlorobenzene at 133° C., treated with anhydrous magnesium sulfate to remove moisture therefrom, and filtered by using silica gel, and a filtrate therefrom was cooled down to room temperature and filtered. The obtained solid was repetitively purified by using monochlorobenzene to obtain 31.0 g (67.1%) of Compound B-12.

Synthesis Example 16: Synthesis of Compound B-25

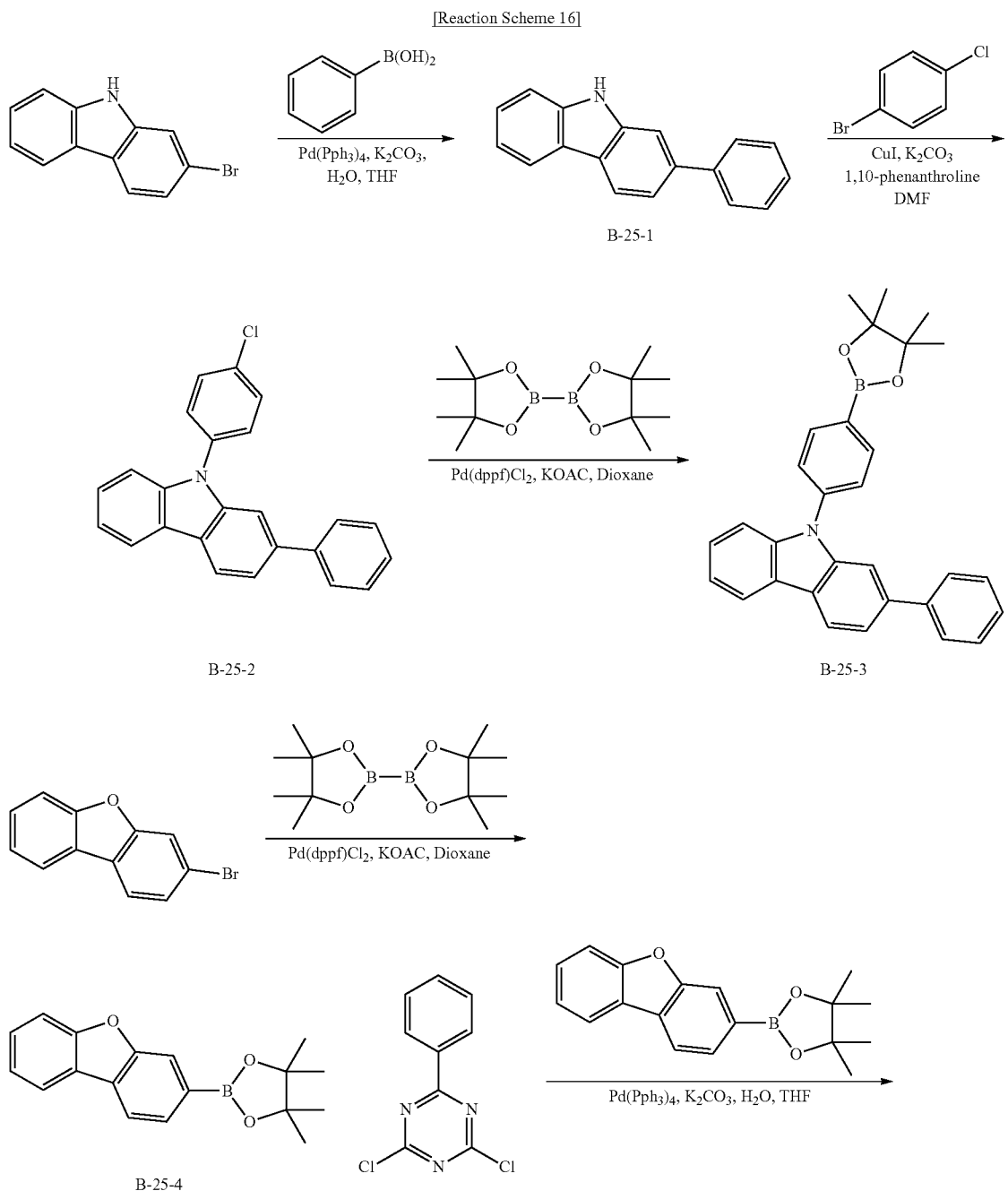

[Reaction Scheme 16]

-continued

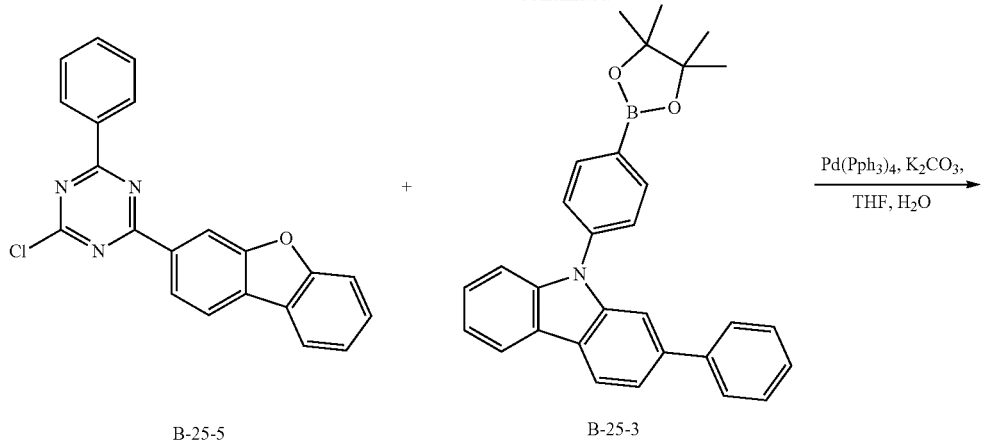

B-25-5      B-25-3

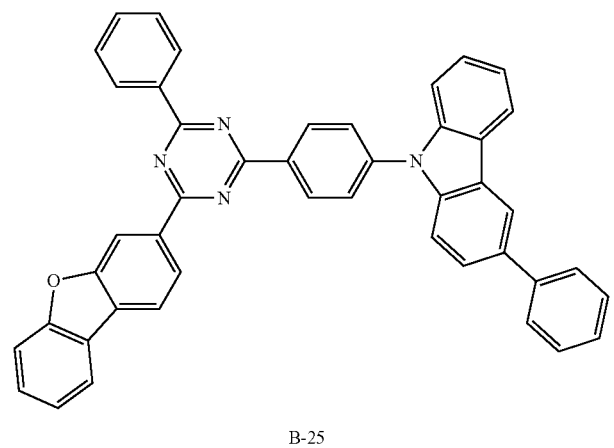

B-25 a) Synthesis of Intermediate B-25-1

22 g (63.6%) of Intermediate B-25-1 was synthesized according to the same method as a) of the method of Synthesis Example 14 by using 2-bromocarbazole (35 g, 142 mmol).

b) Synthesis of Intermediate B-25-2

18 g (56.3%) of Intermediate B-25-2 was synthesized according to the same method as a) of the method of Synthesis Example 15 by using Intermediate B-25-1 (22 g, 90.4 mmol).

c) Synthesis of Intermediate B-25-3

14.8 g (65.3%) of Intermediate B-25-3 was synthesized according to the same method as b) of Synthesis Example 15 by using Intermediate B-25-2 (18 g, 51 mmol).

d) Synthesis of Intermediate B-25-4

31 g (65.1%) of Intermediate B-25-4 was synthesized according to the same method as b) of Synthesis Example 15 by using 3-bromo-dibenzofuran (40 g, 162 mmol).

e) Synthesis of Intermediate B-25-5

15 g (64.8%) of Intermediate B-25-5 was synthesized according to the same method as c) of Synthesis Example 15 by using 2,4-chloro-6-phenyl-1,3,5-triazine (21 g, 93 mmol) and Intermediate B-25-4.

f) Synthesis of Compound B-25

12.7 g (67.5%) of Compound B-25 was synthesized according to the same method as c) of Synthesis Example 15 by using Intermediate B-25-5 (10.5 g 29.3 mmol) and Intermediate B-25-3 (14.38 g, 32.28 mmol).

Synthesis Example 17: Synthesis of Compound B-42

[Reaction Scheme 17]

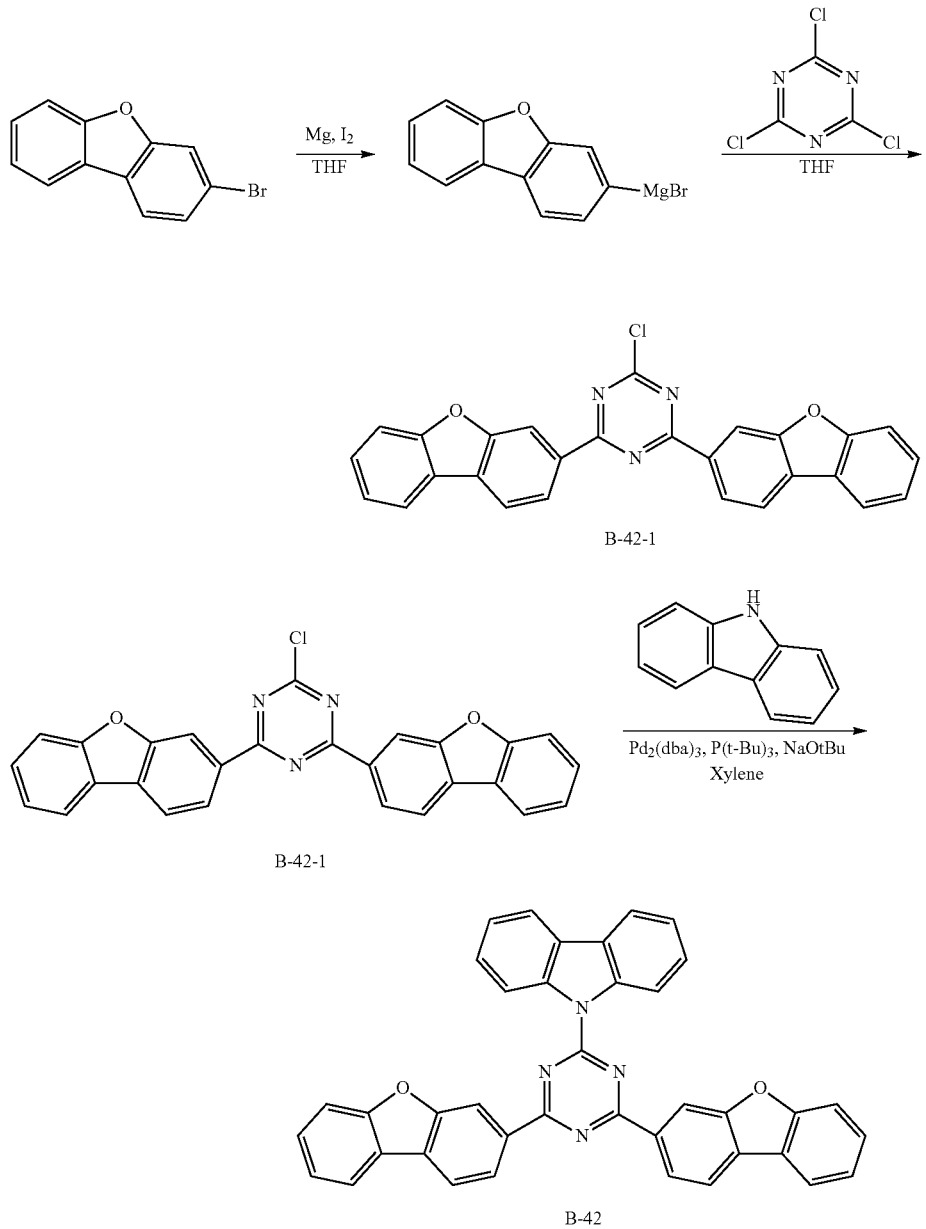

a) Synthesis of Intermediate B-42-1

Mg (3.44 g, 142 mmol) and I2 (0.36 g, 1.41 mmol) were stirred under a nitrogen state. Subsequently, a solution prepared by dissolving 3-bromo-dibenzofuran (35 g, 142 mmol) in 236 ml of anhydrous THF was slowly dropped thereto to obtain 3-Mgbr-dibenzofuran. The mixed solution of 3-Mgbr-dibenzofuran and THF was slowly dropped to another solution prepared by dissolving cyanuric chloride (13.06 g, 70.8 mmol) in 118 ml of anhydrous THF under a nitrogen state while maintained at 0° C., and the obtained mixture was reacted at room temperature for 2 hours. When a reaction was complete, water and ice were added thereto to cool it down, and ethyl acetate was added thereto to extract and separate an aqueous layer and an organic layer. The extracted organic layer was silica filtered, and a solvent obtained therefrom was all evaporated and distilled. Then, a solid therefrom was recrystallized by using n-Hexane and paper-filtered. The solid was dried. Through this method, 21 g (66.2%) of Intermediate B-42-1 was obtained.

b) Synthesis of Compound B-42

18.7 g (68.9%) of Compound B-42 was synthesized according to the same method as c) of Synthesis Example 14 by using Intermediate B-42-1 (21 g, 46.89 mmol) and carbazole (7.84 g, 46.89 mmol).

Synthesis Example 18: Synthesis of Compound B-55

[Reaction Scheme 18]

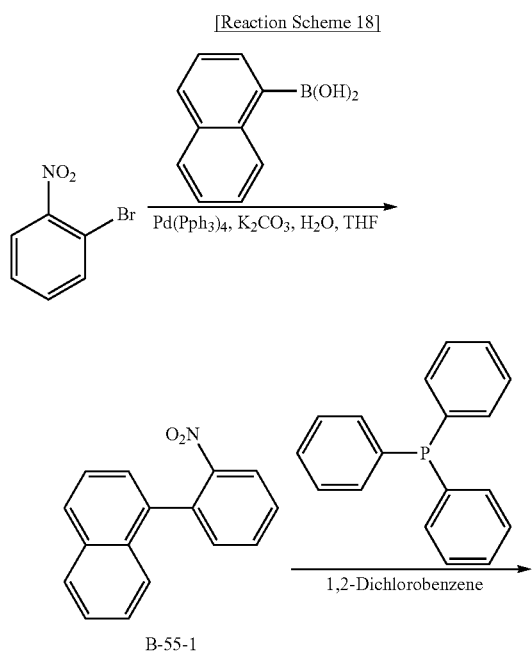

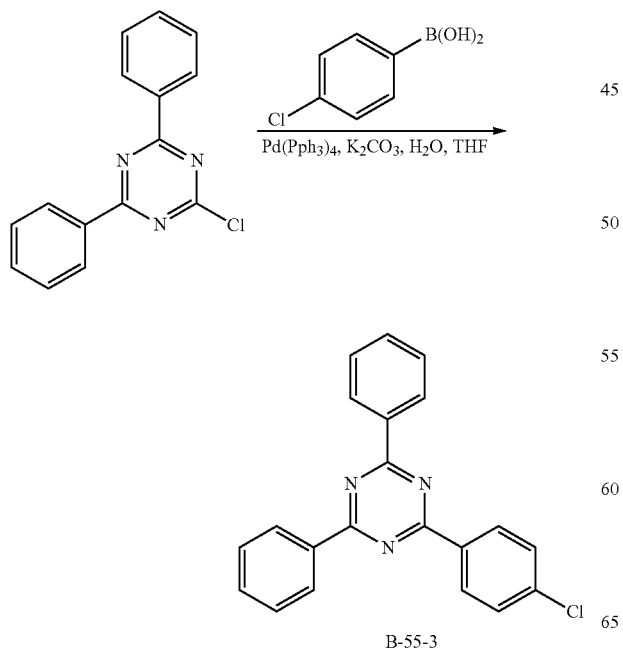

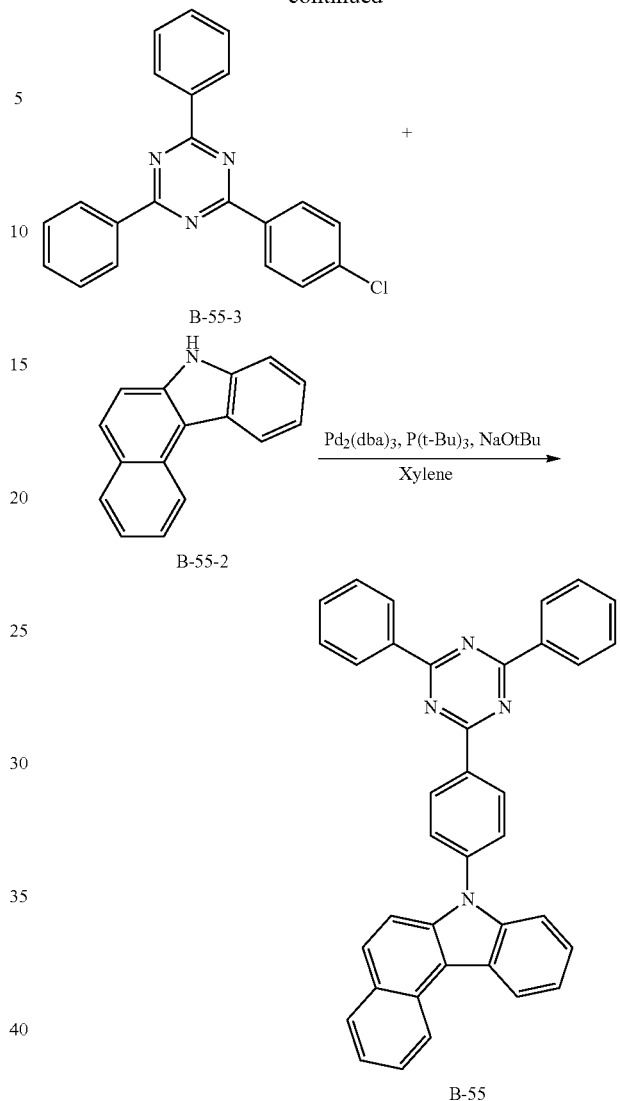

a) Synthesis of Intermediate B-55-1

28 g (64.8%) of Intermediate B-55-1 was synthesized according to the same method as a) of Synthesis Example 14 by using 1-bromo-2-nitro-benzene (35 g, 173.2 mmol) and 1-naphthalene-boronic acid (32.78 g, 190.6 mmol).

b) Synthesis of Intermediate B-55-2

Intermediate B-55-1 (28.0 g, 112 mmol) and triphenylphosphine (88.4 g, 337 mmol) were dissolved in 300 mL of 1,2-dichlorobenzene in a round-bottomed flask and then, stirred at 180° C. for 24 hours. When a reaction was complete, the resultant was treated through column chromatography to remove the solvent and obtain 17.7 g (72.5%) of Intermediate B-55-2.

c) Synthesis of Compound B-55-3

Intermediate B-55-3 was synthesized according to the same method as b) of Synthesis Example 14.

d) Synthesis of Compound B-55

21.0 g (62.6%) of Compound B-55 was synthesized according to the same method as c) of Synthesis Example 14 by using Intermediate B-55-3 (22 g, 63.9 mmol) and Intermediate B-55-2 (13.9 g, 63.9 mmol).

Comparative Synthesis Example 1: Synthesis of Comparative Compound 1

[Reaction Scheme 19]

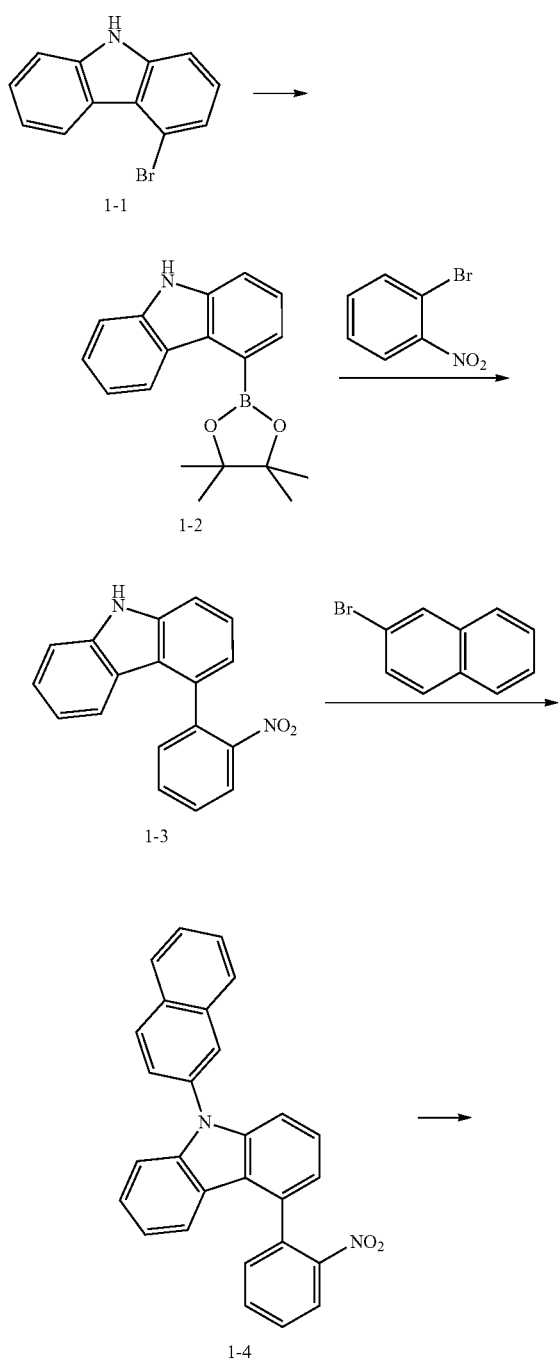

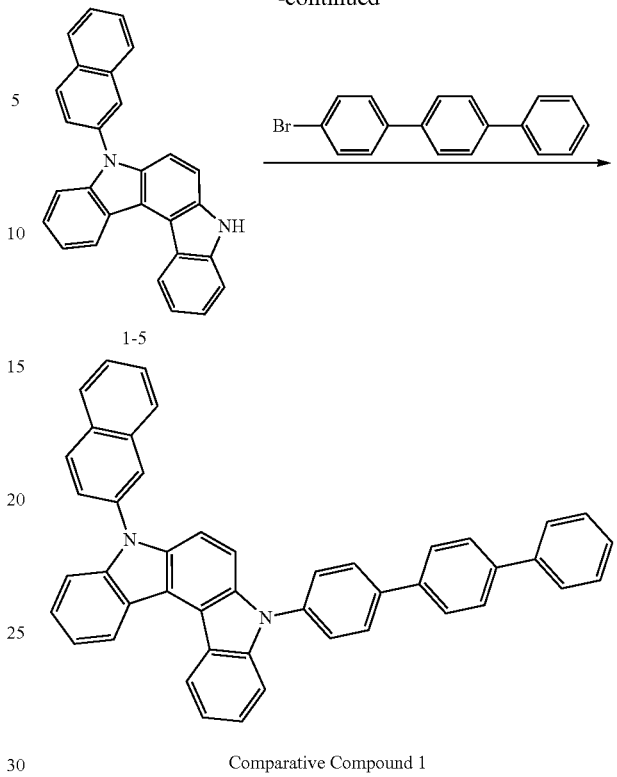

Comparative Compound 1 a) Synthesis of Intermediate 1-2

Intermediate 1-1 (30 g, 121.9 mmol), 1 equivalent of 4,4,4',4',5,5,5',5'-octamethyl-2,2'-bi(1,3,2-dioxaborolane), 2 equivalents of potassium acetate, 0.03 equivalents of 1,1'-bis(diphenylphosphino) ferrocene-palladium(I) dichloride, and 0.2 equivalents of tricyclohexylphosphine were mixed with 300 mL of N,N-dimethylformamide in a 500 mL flask, and the mixture was stirred at 130° C. for 12 hours. When a reaction was complete, an organic layer obtained by extracting a reaction solution with water and EA was concentrated after removing moisture therefrom by using magnesium sulfate and then, purified through column chromatography to obtain Intermediate 1-2 as a white solid (29.66 g, yield: 83%).

b) Synthesis of Intermediate 1-3

29.66 g (0.4 mol) of Intermediate 1-2, 2 equivalents of 1-bromo-2-nitro benzene, 2 equivalents of potassium carbonate, and 0.02 equivalents of tetrakis(triphenylphosphine) palladium (0) were mixed with 200 mL of 1,4-dioxane and 100 mL of water in a 500 mL flask, and the mixture was heated at 90° C. under a nitrogen flow for 16 hours. After removing a reaction solvent therefrom, the obtained resultant was dissolved in dichloromethane, filtered with silica gel/Celite, and then, after removing an appropriate amount of an organic solvent, recrystallized with methanol to obtain Intermediate 1-3 as a solid (16.92 g, yield: 58%).

c) Synthesis of Intermediate 1-4

8.7 g (30.2 mmol) of Intermediate 1-3, 7.5 g (36.2 mmol) of 2-bromonaphthalene, 4.3 g (45.3 mmol) of sodium t-butoxide (NaOtBu), 1.0 g (1.8 mmol) of Pd(dba)$_2$, and 2.2 g of tri t-butylphosphine (P(tBu)$_3$) (50% in toluene) were added to 150 mL of xylene in a 500 mL flask and then, heated and refluxed under a nitrogen flow for 12 hours. After removing the xylene therefrom, 200 mL of methanol was added thereto to crystallize a solid, the solid was filtered, dissolved in dichloromethane, filtered with silica gel/Celite, and then, after removing an appropriate amount of an organic solvent therefrom, recrystallized with acetone to obtain Intermediate 1-4 (9.83 g, yield: 77%).

d) Synthesis of Intermediate 1-5

Intermediate 1-4 (211.37 g, 0.51 mol) and triethyl phosphite (528 ml, 3.08 mol) were put in a 1000 ml flask and then, after substituting nitrogen, stirred at 160° C. for 12 hours. When a reaction was complete, 3 L of MeOH was added thereto, and the obtained mixture was stirred and filtered, and a filtrate therefrom was volatilized. The obtained residue was purified with hexane through column chromatography to obtain Intermediate 1-5 (152.14 g, yield: 78%).

e) Synthesis of Comparative Compound 1

Comparative Compound 1 was synthesized according to c) of Comparative Synthesis Example by using Intermediate 1-5 and Intermediate of 1-(4-bromophenyl)-4-phenylbenzene.

Comparative Synthesis Example 2: Synthesis of Comparative Compound 2

[Reaction Scheme 20]

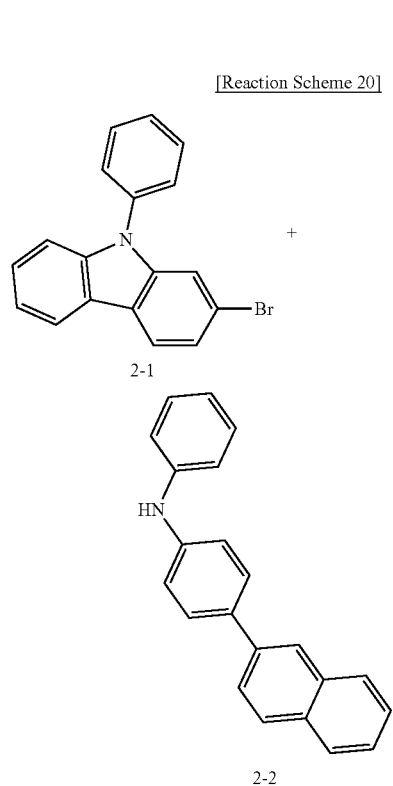

2-1

2-2

-continued

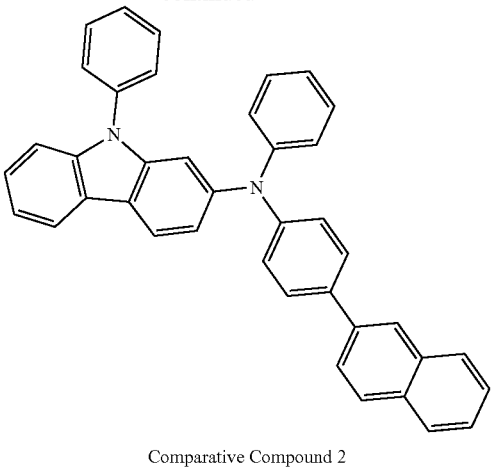

Comparative Compound 2 a) Synthesis of Comparative Compound 2

Comparative Compound 2 was synthesized according to e) of Comparative Synthesis Example 1 by using Intermediate 2-1 and Intermediate 2-2.

Comparative Synthesis Example 3: Synthesis of Comparative Compound 3

[Reaction Scheme 21]

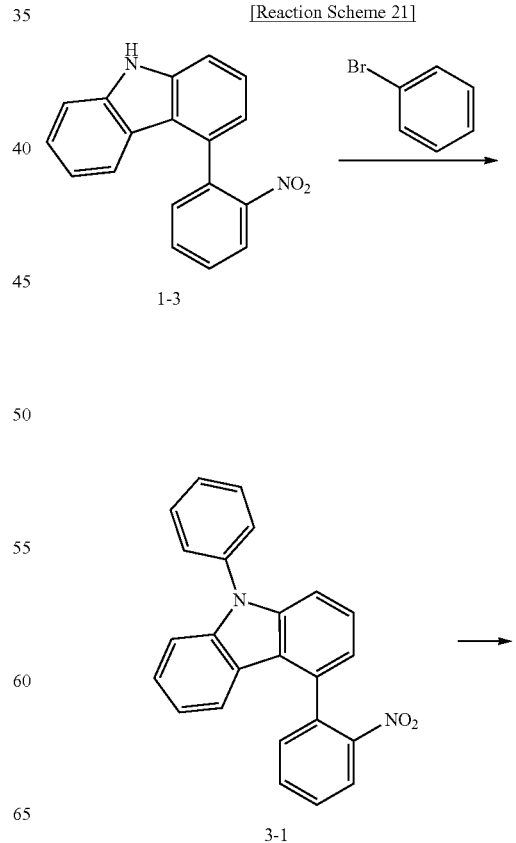

1-3

3-1

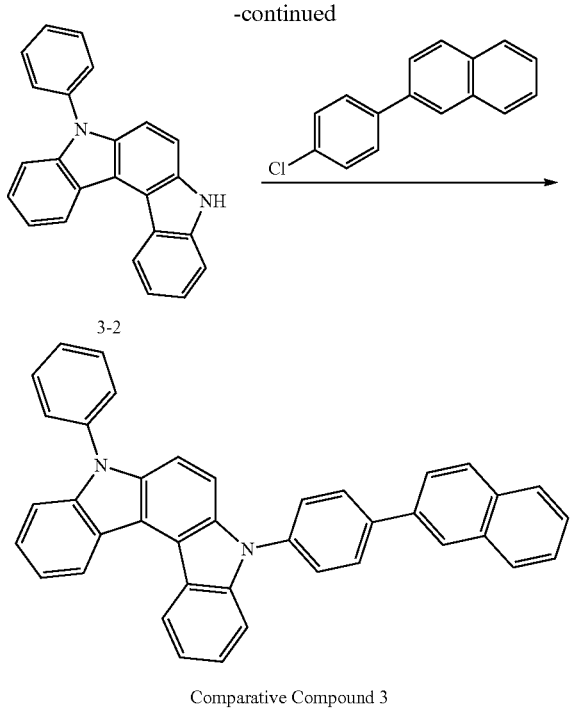

Comparative Compound 3 a) Synthesis of Intermediate 3-1

Intermediate 3-1 was synthesized according to c) of Comparative Synthesis Example 1 by using bromobenzene instead of 2-bromonaphthalene.

b) Synthesis of Intermediate 3-2

Intermediate 3-2 was synthesized according to the same method as d) of Comparative Synthesis Example 1.

c) Synthesis of Comparative Compound 3

Comparative Compound 3 was synthesized according to the same method as e) of Comparative Synthesis Example 1 by using Intermediate 3-2 and 2-(4-chlorophenyl)naphthalene.

Manufacture of Organic Light Emitting Diode

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. On the hole transport layer, a 400 Å-thick hole transport auxiliary layer was formed by depositing Compound C-1. On the hole transport auxiliary layer, a 400 Å-thick light emitting layer was formed by vacuum-depositing Compounds A-2 and B-42 as a host simultaneously and 2 wt % of [Ir(piq)$_2$acac] as a dopant. Herein Compound A-2 and Compound B-42 were used in a weight ratio of 6:4, and their ratio in the following Examples was separately provided. Subsequently, on the light emitting layer, a 300 Å-thick electron transport layer was formed by simultaneously vacuum-depositing the compound D and Liq in a ratio of 1:1, and on the electron transport layer, Liq and Al were sequentially vacuum-deposited to be 15 Å thick and 1200 Å thick, manufacturing an organic light emitting diode.

The organic light emitting diode had a five-layered organic thin layer, and specifically the following structure.

ITO/Compound A (700 Å)/Compound B (50 Å)/Compound C (700 Å)/Compound C-1 (400 Å)/EML[Compound A-2: B-42: [Ir(piq)$_2$acac](2 wt %)](400 Å)/Compound D: Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN)

Compound C: N-(biphenyl-4-yl)-9,9-dimethyl-N-(4-(9-phenyl-9H-carbazol-3-yl)phenyl)-9H-fluoren-2-amine Compound C-1: N,N-di([1,1'-biphenyl]-4-yl)-7,7-dimethyl-7H-fluoreno[4,3-b]benzofuran-10-amine Compound D: 8-(4-(4,6-di(naphthalen-2-yl)-1,3,5-triazin-2-yl)phenyl)quinoline Examples 2 to 6 and Comparative Examples 1 to 5

Each organic light emitting diode was manufactured according to the same method as Example 1 except that compositions are changed as shown in Tables 1 to 5.

Evaluation

Power efficiency of the organic light emitting diodes according to Examples 1 to 6 and Comparative Examples 1 to 5 was evaluated.

Specific measurement methods are as follows, and the results are shown in Tables 1 to 5.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000 Å), while the voltage of the organic light emitting diodes was increased from 0 V to 10 V.

(3) Measurement of Power Efficiency

Power efficiency (cd/A) at the same current density (10 mA/cm$^2$) were calculated by using the luminance, current density, and voltages (V) from the items (1) and (2).

(4) Measurement of Life-Span

The results were obtained by measuring a time when current efficiency (cd/A) was decreased down to 97%, while luminance (cd/m$^2$) was maintained to be 9000 cd/m$^2$.

(5) Calculation of T97 Life-Span Ratio (%)

A relative T97 (h) comparison value of Example (applying a first compound as a first host) and Comparative Example (applying a comparative compound as a first host) applying the same second host is calculated.

T97 life-span ratio (%)={[T97 (h) of Example (applying a first compound as a first host)]/[T97 (h) of Comparative Example (applying a comparative compound as a first host)]}×100

(6) Measurement of Driving Voltage

A driving voltage of each diode was measured using a current-voltage meter (Keithley 2400) at 15 mA/cm$^2$.

(7) Calculation of Driving Voltage Ratio (%)

A relative comparison value of Example (applying a first compound as a first host) and Comparative Example (applying a comparative compound as a first host) applying the same second host is calculated.

Driving voltage ratio (%)={[Driving voltage ($V$) of Example (applying a first compound as a first host)]/[Driving voltage ($V$) of Comparative Example (applying a comparative compound as a first host)]}×100

TABLE 1

|  | First host | Second host | First host: Second host ratio (wt:wt) | Color | Driving voltage (V) | Driving voltage ratio (%) | T97 life-span ratio (%) |
|---|---|---|---|---|---|---|---|
| Example 1 | A-2 | B-42 | 6:4 | red | 3.91 | 95 | 656 |
| Comparative Example 1 | Comparative Compound 2 | B-42 | 6:4 | red | 4.10 | 100 | 100 |

TABLE 2

|  | First host | Second host | First host: Second host ratio (wt:wt) | Color | Driving voltage (V) | Driving voltage ratio (%) | T97 life-span ratio (%) |
|---|---|---|---|---|---|---|---|
| Example 2 | A-2 | B-8 | 6:4 | red | 3.88 | 91 | 379 |
| Example 3 | A-11 | B-8 | 6:4 | red | 3.67 | 86 | 957 |
| Comparative Example 2 | Comparative Compound 1 | B-8 | 6:4 | red | 4.26 | 100 | 100 |

TABLE 3

|  | First host | Second host | First host: Second host ratio (wt:wt) | Color | Driving voltage (V) | Driving voltage ratio (%) | T97 life-span ratio (%) |
|---|---|---|---|---|---|---|---|
| Example 4 | A-2 | B-12 | 6:4 | red | 3.81 | 92 | 208 |
| Comparative Example 3 | Comparative Compound 3 | B-12 | 6:4 | red | 4.13 | 100 | 100 |

TABLE 4

|  | First host | Second host | First host: Second host ratio (wt:wt) | Color | Driving voltage (V) | Driving voltage ratio (%) | T97 life-span ratio (%) |
|---|---|---|---|---|---|---|---|
| Example 5 | A-2 | B-25 | 5:5 | red | 3.79 | 93 | 425 |
| Comparative Example 4 | Comparative Compound 1 | B-25 | 5:5 | red | 4.08 | 100 | 100 |

TABLE 5

|  | First host | Second host | First host: Second host ratio (wt:wt) | Color | Driving voltage (V) | Driving voltage ratio (%) | T97 life-span ratio (%) |
|---|---|---|---|---|---|---|---|
| Example 6 | A-2 | B-55 | 5:5 | red | 3.66 | 87 | 123 |
| Comparative Example 5 | Comparative Compound 1 | B-55 | 5:5 | red | 4.20 | 100 | 100 |

Referring to Tables 1 to 5, organic light emitting diodes according to Examples 1 to 6 exhibited remarkably improved driving voltage, and life-span compared with those of Comparative Examples 1 to 5.

While this invention has been described in connection with what is presently considered to be practical example embodiments, itis to be understood that the invention is not limited to the disclosed embodiments, but, on the contrary, is intended to cover various modifications and equivalent arrangements included within the spirit and scope of the appended claims.

The invention claimed is:
1. A composition, comprising
a first compound represented by a combination of Chemical Formula 1 and Chemical Formula 2, and
a second compound represented by Chemical Formula 3:

[Chemical Formula 1]

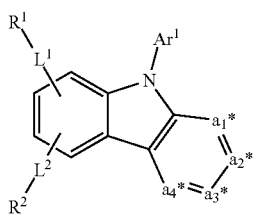

[Chemical Formula 2]

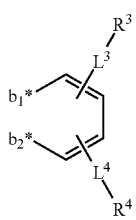

wherein, in Chemical Formula 1 and Chemical Formula 2,
$Ar^1$ is a substituted or unsubstituted C6 to C30 aryl group, a substituted or unsubstituted C2 to C30 heterocyclic group, or a combination thereof,
adjacent two of $a_1^*$ to $a_4^*$ are linked with $b_1^*$ and $b_2^*$, respectively,
remaining two of $a_1^*$ to $a_4^*$ not being linked with $b_1^*$ and $b_2^*$ are independently $C\text{-}L^a\text{-}R^a$,
$L^a$ and $L^1$ to $L^4$ are independently a single bond, a substituted or unsubstituted C6 to C20 arylene group, a substituted or unsubstituted C2 to C20 heterocyclic group, or a combination thereof,
$R^a$ and $R^1$ to $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and
at least one of $R^a$ and $R^1$ to $R^4$ is a group represented by Chemical Formula A,

[Chemical Formula A]

wherein, in Chemical Formula A,
$R^b$ and $R^c$ are independently a substituted or unsubstituted C6 to C30 aryl group, a substituted or unsubstituted C2 to C30 heterocyclic group, or a combination thereof, and
* is a linking point with $L^a$ and $L^1$ to $L^4$;

[Chemical Formula 3]

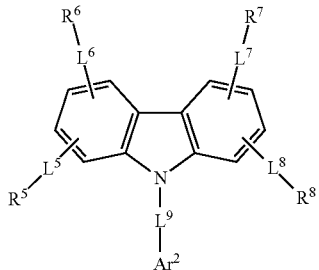

wherein, in Chemical Formula 3,
$L^5$ to $L^9$ are independently a single bond, a substituted or unsubstituted C6 to C20 arylene group, a substituted or unsubstituted C2 to C20 heterocyclic group, or a combination thereof,
$Ar^2$ is a substituted or unsubstituted C6 to C30 aryl group, a substituted or unsubstituted C2 to C30 heterocyclic group, or a combination thereof,
$R^5$ to $R^8$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
$R^5$ to $R^8$ are independently present or adjacent groups thereof are linked with each other to form a substituted or unsubstituted aromatic monocyclic or polycyclic ring, and
at least one of $Ar^2$ and $R^5$ to $R^8$ is a group represented by Chemical Formula B,

[Chemical Formula B]

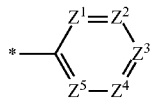

wherein, in Chemical Formula B,
$Z^1$ to $Z^5$ are independently N or $C\text{-}L^b\text{-}R^d$,
at least one of $Z^1$ to $Z^5$ is N,
wherein $L^b$ is independently a single bond, a substituted or unsubstituted C6 to C20 arylene group, a substituted or unsubstituted C2 to C20 heterocyclic group, or a combination thereof,
$R^d$ is independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof,
$R^d$ is independently present or adjacent groups thereof are linked with each other to form a substituted or unsubstituted aromatic monocyclic or polycyclic ring, or a substituted or unsubstituted aromatic monocyclic or polycyclic heteroring, and
* is a linking point with $L^5$ to $L^9$.

2. The composition of claim 1, wherein the first compound is represented by one of Chemical Formula 1A to Chemical Formula 1C:

[Chemical Formula 1A]

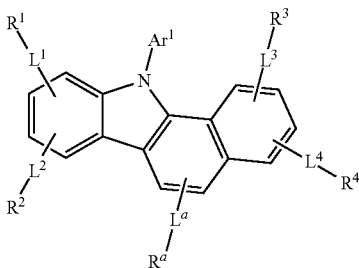

[Chemical Formula 1B]

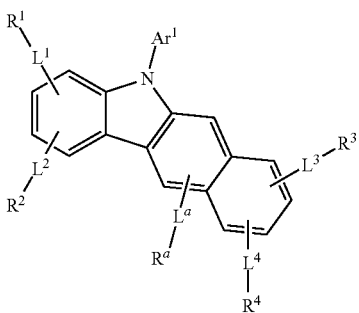

[Chemical Formula 1C]

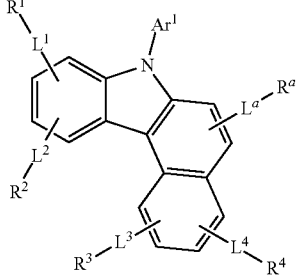

wherein, in Chemical Formula 1A to Chemical Formula 1C, $Ar^1$ is a substituted or unsubstituted C6 to C30 aryl group, a substituted or unsubstituted C2 to C30 heterocyclic group, or a combination thereof, $L^a$ and $L^1$ to $L^4$ are independently a single bond, a substituted or unsubstituted C6 to C20 arylene group, a substituted or unsubstituted C2 to C20 heterocyclic group, or a combination thereof, $R^a$ and $R^1$ to $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and at least one of $R^a$ and $R^1$ to $R^4$ is a group represented by Chemical Formula A,

[Chemical Formula A]

wherein, in Chemical Formula A, $R^b$ and $R^c$ are independently a substituted or unsubstituted C6 to C30 aryl group, a substituted or unsubstituted C2 to C30 heterocyclic group, or a combination thereof, and

* is a linking point with $L^a$ and $L^1$ to $L^4$.

3. The composition of claim 1, wherein the first compound is represented by one of Chemical Formula 1A-1 to Chemical Formula 1A-3, Chemical Formula 1B-1 to Chemical Formula 1B-3 and Chemical Formula 1C-1 to Chemical Formula 1C-3:

[Chemical Formula 1A-1]

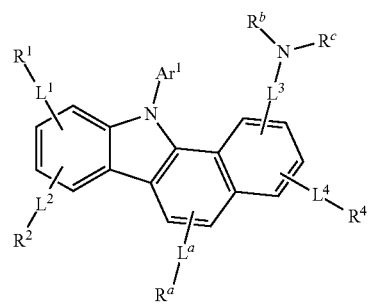

[Chemical Formula 1A-2]

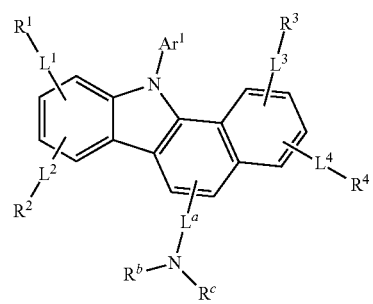

[Chemical Formula 1A-3]

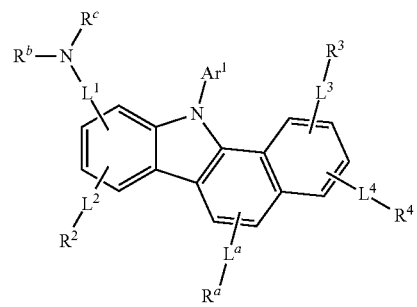

[Chemical Formula 1B-1]

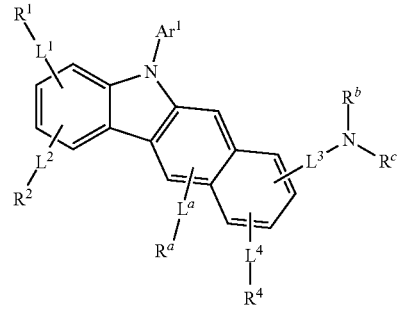

-continued

[Chemical Formula 1B-2]

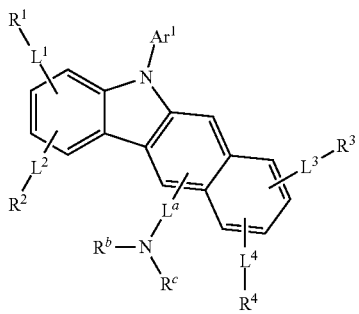

[Chemical Formula 1B-3]

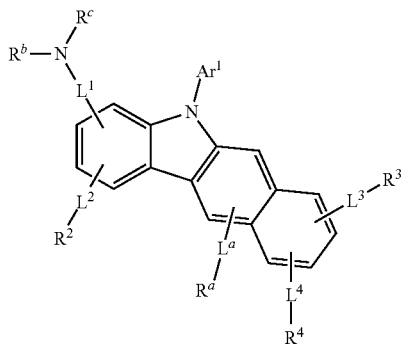

[Chemical Formula 1C-1]

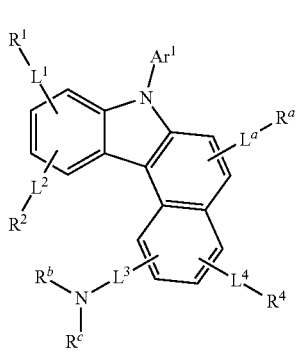

[Chemical Formula 1C-2]

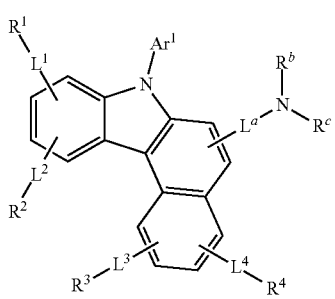

-continued

[Chemical Formula 1C-3]

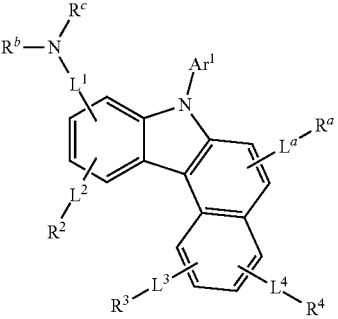

wherein, in Chemical Formula 1A-1 to Chemical Formula 1A-3, Chemical Formula 1B-1 to Chemical Formula 1B-3, and Chemical Formula 1C-1 to Chemical Formula 1C-3, $Ar^1$ is a substituted or unsubstituted C6 to C30 aryl group, a substituted or unsubstituted C2 to C30 heterocyclic group, or a combination thereof, $L^a$ and $L^1$ to $L^4$ are independently a single bond, a substituted or unsubstituted C6 to C20 arylene group, a substituted or unsubstituted C2 to C20 heterocyclic group, or a combination thereof, $R^a$ and $R^1$ to $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and $R^b$ and $R^c$ are independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group or a substituted or unsubstituted dibenzothiophenyl group.

4. The composition of claim 1, wherein the first compound is represented by Chemical Formula 1A-1-b:

[Chemical Formula 1A-1-b]

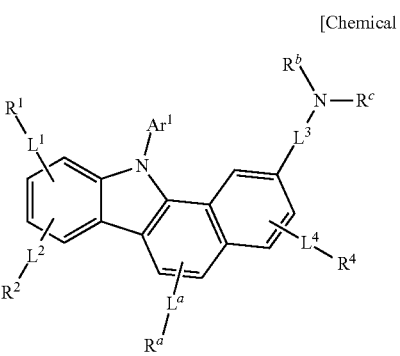

wherein, in Chemical Formula 1A-1-b, $Ar^1$ is a substituted or unsubstituted C6 to C30 aryl group, a substituted or unsubstituted C2 to C30 heterocyclic group, or a combination thereof, $L^a$ and $L^1$ to $L^4$ are independently a single bond, a substituted or unsubstituted C6 to C20 arylene group, a substituted or unsubstituted C2 to C20 heterocyclic group, or a combination thereof, $R^a$ and $R^1$, $R^2$ and $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and $R^b$ and $R^c$ are independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group or a substituted or unsubstituted dibenzothiophenyl group.

5. The composition of claim 1, wherein the second compound is represented by one of Chemical Formula 2A to Chemical Formula 2L:

[Chemical Formula 2A]

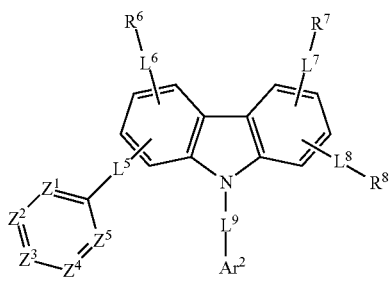

[Chemical Formula 2B]

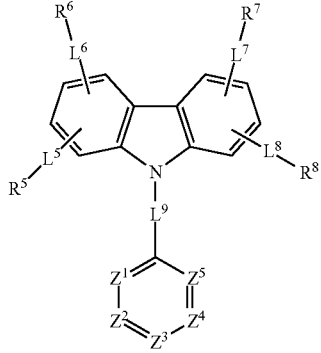

[Chemical Formula 2C]

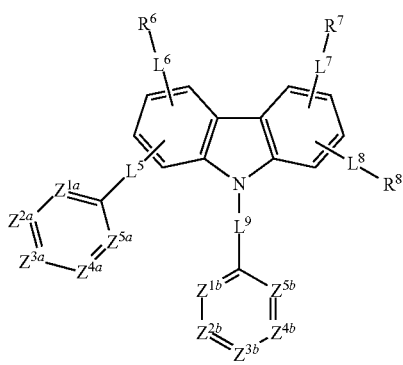

[Chemical Formula 2D]

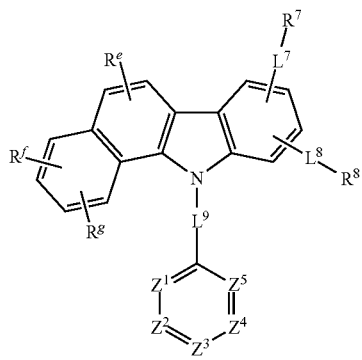

[Chemical Formula 2E]

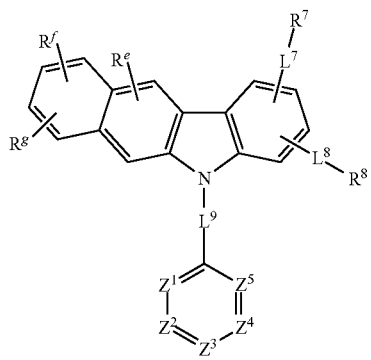

[Chemical Formula 2F]

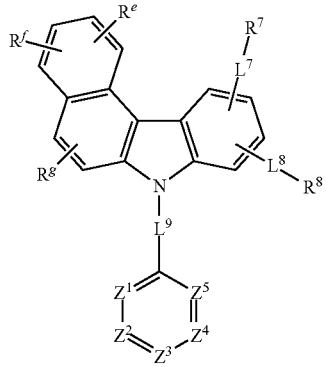

[Chemical Formula 2G]

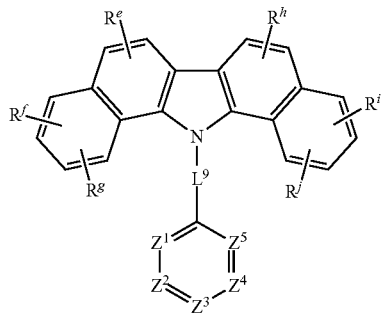

-continued

[Chemical Formula 2H]

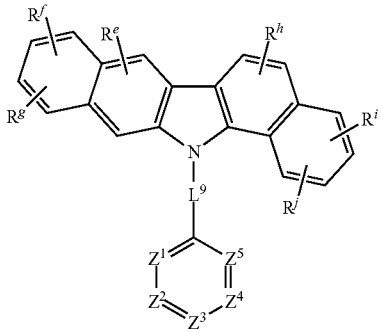

[Chemical Formula 2I]

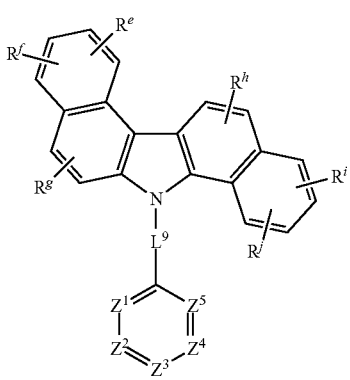

[Chemical Formula 2J]

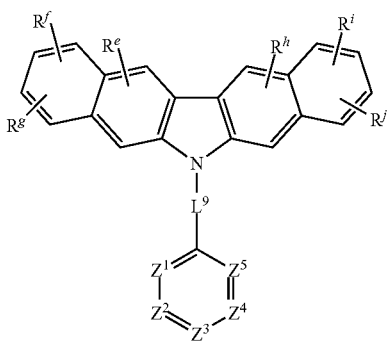

[Chemical Formula 2K]

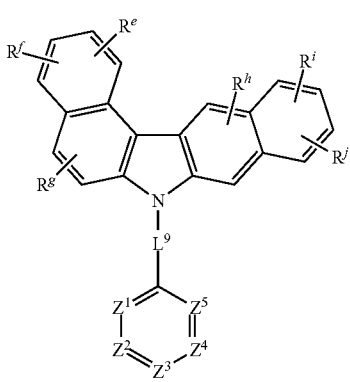

-continued

[Chemical Formula 2L]

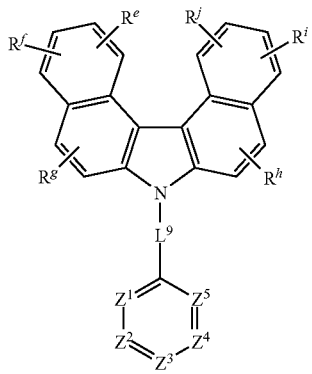

wherein, in Chemical Formulae 2A to 2L,

L$^5$ to L$^9$ are independently a single bond, a substituted or unsubstituted C6 to C20 arylene group, a substituted or unsubstituted C2 to C20 heterocyclic group, or a combination thereof, Ar$^2$ is a substituted or unsubstituted C6 to C30 aryl group, a substituted or unsubstituted C2 to C30 heterocyclic group, or a combination thereof, R$^5$ to R$^8$, R$^e$, R$^f$, R$^g$, R$^h$, R$^i$, and R$^j$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, Z$^1$ to Z$^5$ are independently N or C-L$^b$-R$^d$, at least one of Z$^1$ to Z$^5$ is N, Z$^{1a}$ to Z$^{5a}$ are independently N or C-L$^b$-R$^d$, at least one of Z$^{1a}$ to Z$^{5a}$ is N, Z$^{1b}$ to Z$^{5b}$ are independently N or C-L$^b$-R$^d$, at least one of Z$^{1b}$ to Z$^{5b}$ is N, wherein L$^b$ is independently a single bond, a substituted or unsubstituted C6 to C20 arylene group, a substituted or unsubstituted C2 to C20 heterocyclic group, or a combination thereof, R$^d$ is independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, and R$^d$ is independently present or adjacent groups thereof are linked with each other to form a substituted or unsubstituted monocyclic or polycyclic ring, or a substituted or unsubstituted aromatic monocyclic or polycyclic heteroring.

6. The composition of claim 5, wherein the second compound is represented by one of Chemical Formula 2B, Chemical Formula 2C, Chemical Formula 2D, Chemical Formula 2E, and Chemical Formula 2F.

7. The composition of claim 5, wherein the second compound is represented by one of Chemical Formula 2B or Chemical Formula 2F.

8. The composition of claim 1, wherein the group represented by Chemical Formula B is a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinoxalinyl group, a substituted or unsubstituted quinazolinyl group, or a substituted or unsubstituted naphthyridinyl group.

9. The composition of claim 1, wherein Chemical Formula B is represented by one of Chemical Formula B-1 to Chemical Formula B-7:

[Chemical Formula B-1]
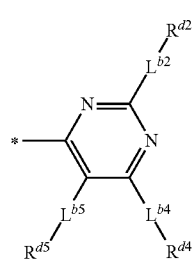

[Chemical Formula B-2]
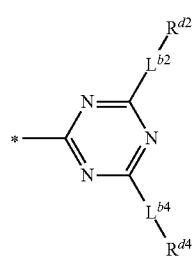

[Chemical Formula B-3]
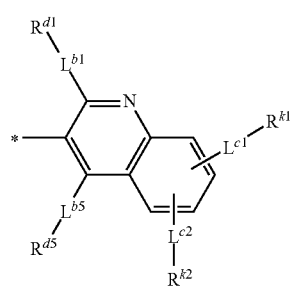

[Chemical Formula B-4]
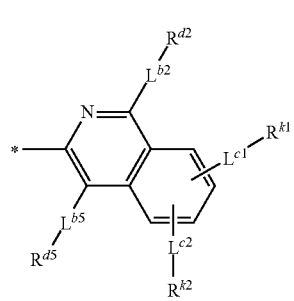

[Chemical Formula B-5]
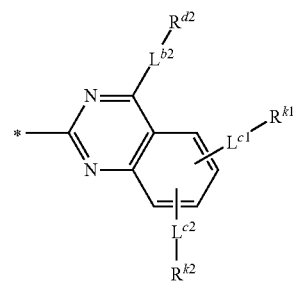

[Chemical Formula B-6]
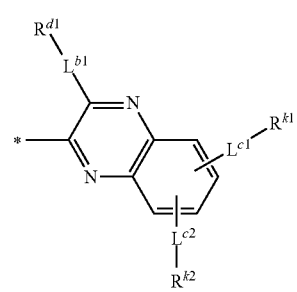

[Chemical Formula B-7]

wherein, in Chemical Formula B-1 to Chemical Formula B-7, $L^{b1}$ to $L^{b5}$, $L^{c1}$, and $L^{c2}$ are independently a single bond, a substituted or unsubstituted C6 to C20 arylene group, a substituted or unsubstituted C2 to C20 heterocyclic group, or a combination thereof, $R^{d1}$ to $R^{d5}$, $R^{k1}$, and $R^{k2}$ are independently hydrogen, deuterium, a cyano group, a substituted or unsubstituted amine group, a substituted or unsubstituted C1 to C10 alkyl group, a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted fluorenyl group, a substituted or unsubstituted triphenylene group, a substituted or unsubstituted dibenzofuranyl group, or a substituted or unsubstituted dibenzothiophenyl group, and

* is a linking point with $L^5$ to $L^9$.

10. The composition of claim 1, wherein Chemical Formula B is one selected from substituents of Group I:

[Group I]
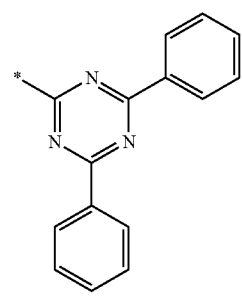

169
-continued
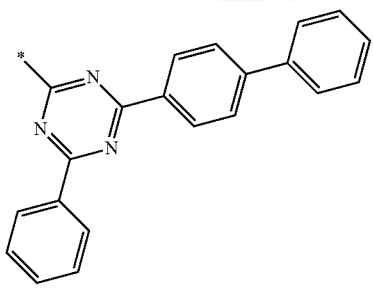
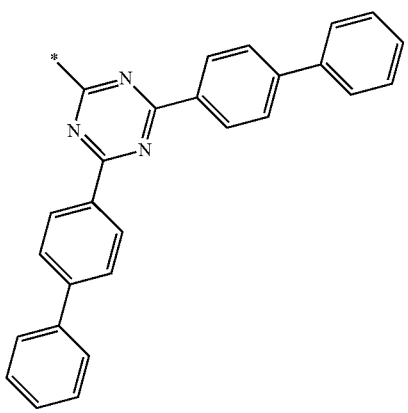
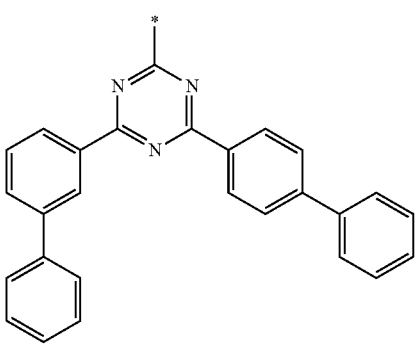
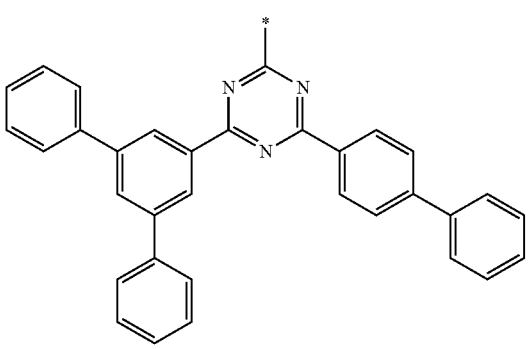
170
-continued
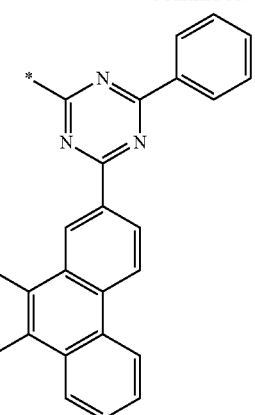
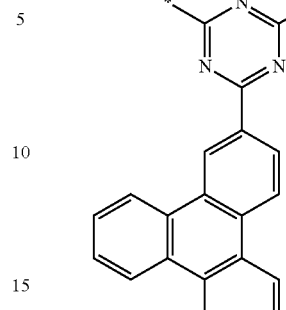
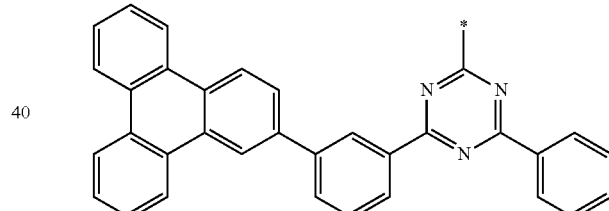
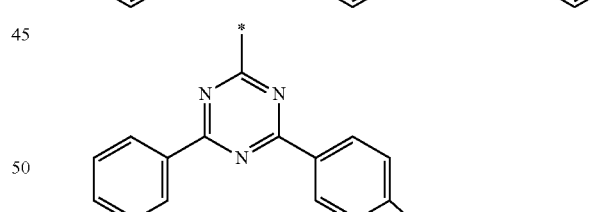
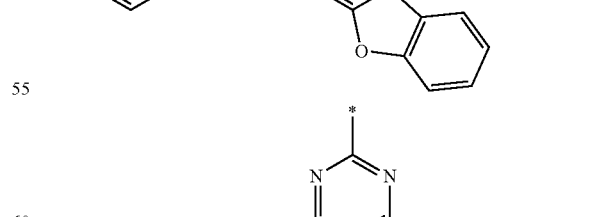
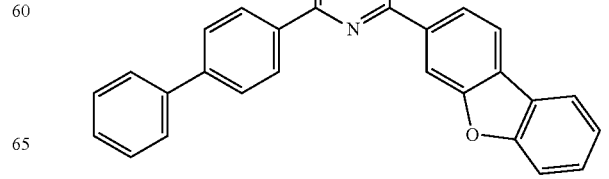

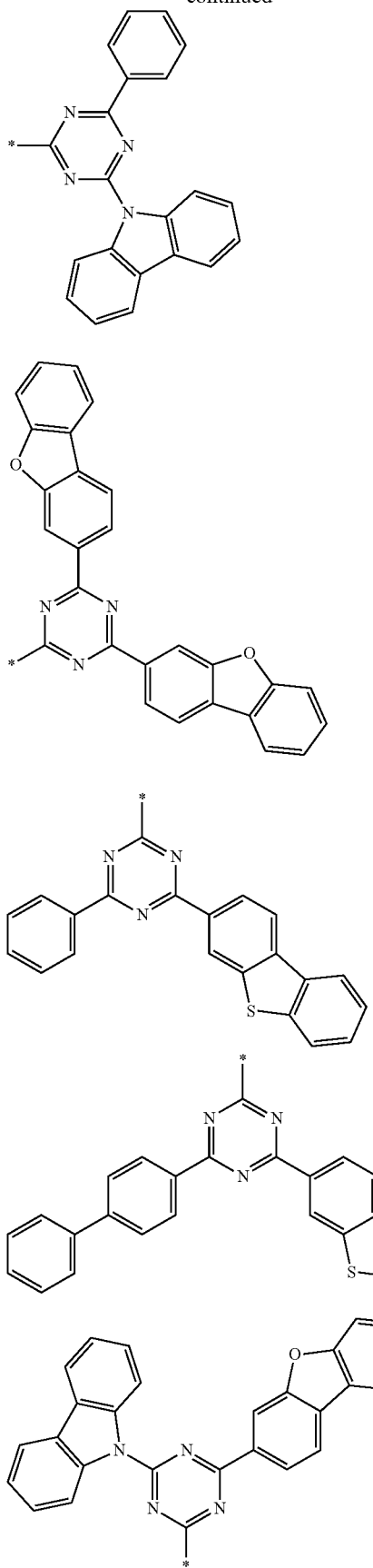

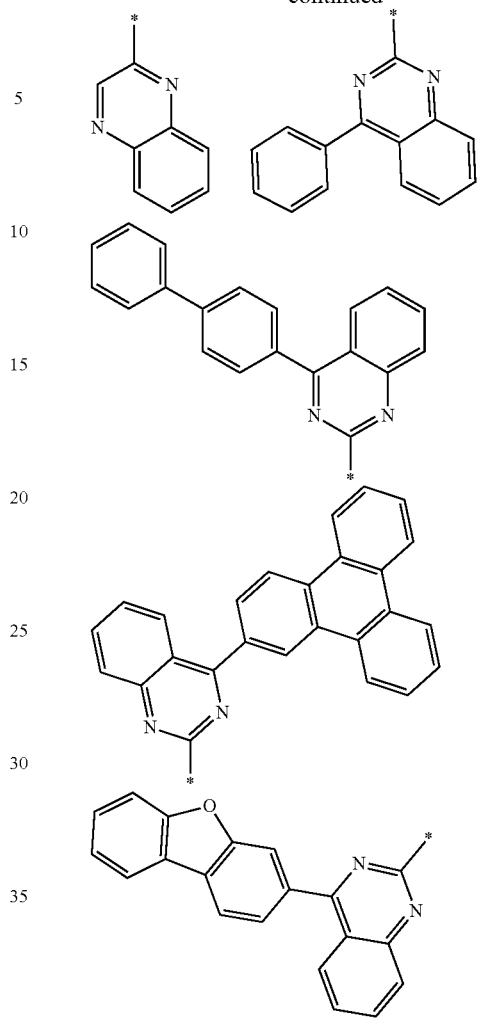

wherein, in Group I, * is a linking point.

11. The composition of claim 1, wherein the first compound is represented by Chemical Formula 1A-1-b, and the second compound is represented by Chemical Formula 2B or Chemical Formula 2F:

[Chemical Formula 1A-1-b]

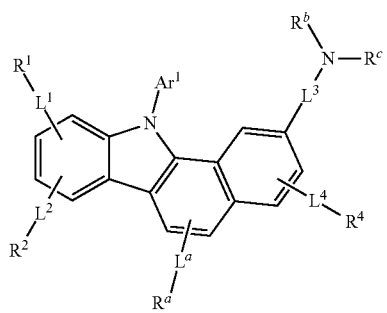

wherein, in Chemical Formula 1A-1-b,

Ar$^1$ is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylene group, a substituted or unsubstituted fluorenyl group, a substituted or unsubstituted dibenzofuranyl group, a substituted or unsubstituted dibenzothiophenyl group, a substituted or unsubstituted carbazolyl group, or a combination thereof, $L^a$ and $L^1$ to $L^4$ are independently a single bond, a substituted or unsubstituted phenylene group, a substituted or unsubstituted biphenylene group, a substituted or unsubstituted terphenylene group, or a substituted or unsubstituted naphthylene group, $R^a$, $R^1$, $R^2$, and $R^4$ are independently hydrogen, deuterium, a cyano group, a substituted or unsubstituted amine group, a substituted or unsubstituted C1 to C30 alkyl group, a substituted or unsubstituted C6 to C30 aryl group, a substituted or unsubstituted C2 to C30 heterocyclic group, or a combination thereof, and $R^b$ and $R^c$ are independently a substituted or unsubstituted phenyl group, a substituted or unsubstituted biphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group;

[Chemical Formula 2B]

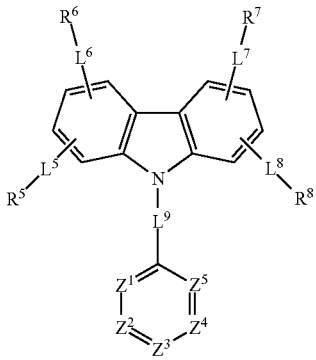

[Chemical Formula 2F]

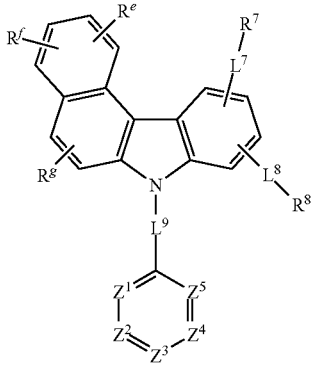

wherein, in Chemical Formula 2B and Chemical Formula 2F, $L^5$ to $L^9$ are independently a single bond, a substituted or unsubstituted phenylene group, a substituted or unsubstituted biphenylene group, a substituted or unsubstituted terphenylene group, or a substituted or unsubstituted naphthylene group, $R^5$ to $R^8$, $R^e$, $R^f$ and $R^g$ are independently hydrogen, deuterium, a substituted or unsubstituted C1 to C30 alkyl group, a substituted or unsubstituted C6 to C30 aryl group, a substituted or unsubstituted C2 to C30 heterocyclic group, a substituted or unsubstituted silyl group, a substituted or unsubstituted amine group, a halogen, a cyano group, or a combination thereof, $Z^1$ to $Z^5$ are independently N or $C\text{-}L^b\text{-}R^d$, at least two of $Z^1$ to $Z^5$ are N, wherein $L^b$ is independently a single bond, or a substituted or unsubstituted C6 to C20 arylene group, and $R^d$ is independently a substituted or unsubstituted phenyl group, a substituted or unsubstituted biphenyl group, a substituted or unsubstituted terphenyl group, a substituted or unsubstituted anthracenyl group, a substituted or unsubstituted naphthyl group, a substituted or unsubstituted phenanthrenyl group, a substituted or unsubstituted triphenylene group, a substituted or unsubstituted fluorenyl group, a substituted or unsubstituted carbazolyl group, a substituted or unsubstituted dibenzofuranyl group, or a substituted or unsubstituted dibenzothiophenyl group.

12. The composition of claim 1, which further comprises a dopant.

13. An organic optoelectronic device, comprising
an anode and a cathode facing each other,
at least one organic layer disposed between the anode and the cathode,
wherein the organic layer comprises the composition of claim 1.

14. The organic optoelectronic device of claim 13, wherein
the organic layer comprises a light emitting layer, and
the light emitting layer comprises the composition.

15. The organic optoelectronic device of claim 14, wherein the first compound and the second compound are included as a phosphorescent host of the light emitting layer, respectively.

16. The organic optoelectronic device of claim 14, wherein the composition is a red light emitting composition.

17. A display device comprising the organic optoelectronic device of claim 13.

* * * * *